US011291641B2

(12) United States Patent
Fiorina et al.

(10) Patent No.: US 11,291,641 B2
(45) Date of Patent: Apr. 5, 2022

(54) PREVENTION AND TREATMENT OF DIABETIC NEPHROPATHY

(71) Applicants: THE CHILDREN'S MEDICAL CENTER CORPORATION, Boston, MA (US); DOMPE FARMACEUTICI S.P.A., Milan (IT)

(72) Inventors: Paolo Fiorina, Boston, MA (US); Roberto Bassi, Boston, MA (US); Andrea Vergani, Brookline, MA (US); Marcello Allegretti, Rome (IT)

(73) Assignees: THE CHILDREN'S MEDICAL CENTER CORPORATION, Boston, MA (US); DOMPE FARMACEUTICI S.P.A., Milan (IT)

(*) Notice: Subject to any disclaimer, the term of this patent is extended or adjusted under 35 U.S.C. 154(b) by 0 days.

(21) Appl. No.: 16/338,834

(22) PCT Filed: Oct. 3, 2017

(86) PCT No.: PCT/US2017/054916
§ 371 (c)(1),
(2) Date: Apr. 2, 2019

(87) PCT Pub. No.: WO2018/067548
PCT Pub. Date: Apr. 12, 2018

(65) Prior Publication Data
US 2019/0224148 A1 Jul. 25, 2019

Related U.S. Application Data

(60) Provisional application No. 62/403,368, filed on Oct. 3, 2016.

(51) Int. Cl.
*A61K 31/18* (2006.01)
*A61K 31/426* (2006.01)
*A61P 3/10* (2006.01)
*A61P 13/12* (2006.01)
*A61K 45/06* (2006.01)
*G01N 33/68* (2006.01)

(52) U.S. Cl.
CPC ............ *A61K 31/18* (2013.01); *A61K 31/426* (2013.01); *A61K 45/06* (2013.01); *A61P 3/10* (2018.01); *A61P 13/12* (2018.01); *G01N 33/68* (2013.01)

(58) Field of Classification Search
CPC ...... A61K 31/18; A61K 31/426; A61K 45/06; A61P 3/10; A61P 13/12; G01N 33/68
See application file for complete search history.

(56) References Cited

U.S. PATENT DOCUMENTS

| | | | |
|---|---|---|---|
| 5,326,707 A | 7/1994 | Franke et al. | |
| 5,385,847 A | 1/1995 | Yip et al. | |
| 5,492,834 A | 2/1996 | Liu et al. | |
| 5,750,405 A | 5/1998 | Albarella et al. | |
| 6,133,426 A | 10/2000 | Gonzalez et al. | |
| 6,468,532 B1 | 10/2002 | Hsei et al. | |
| 8,440,655 B2 | 5/2013 | Seed et al. | |
| 2003/0027216 A1 | 2/2003 | Kiernan et al. | |
| 2003/0232396 A1 | 12/2003 | Mathew et al. | |
| 2004/0087601 A1* | 5/2004 | Erickson | C07D 231/12 514/269 |
| 2004/0229901 A1* | 11/2004 | Otsuki | A61K 31/00 514/303 |
| 2006/0063836 A1* | 3/2006 | Roman | A61K 31/202 514/560 |
| 2006/0240437 A1 | 10/2006 | Krolewski et al. | |
| 2011/0262386 A1* | 10/2011 | Bernhagen | C07K 16/24 424/85.2 |
| 2011/0281758 A1 | 11/2011 | Niewczas et al. | |
| 2012/0202884 A1 | 8/2012 | Piemonti et al. | |
| 2015/0011639 A1 | 1/2015 | Piemonti et al. | |

FOREIGN PATENT DOCUMENTS

| | | | | |
|---|---|---|---|---|
| EP | 0934940 A1 * | 8/1999 | ............ | C07D 495/04 |
| EP | E P-1283217 A2 * | 2/2003 | ......... | C07K 16/2866 |
| WO | WO-9729743 A1 * | 8/1997 | ............ | C07C 275/42 |
| WO | WO-9932121 A1 * | 7/1999 | ............ | C07D 403/04 |
| WO | WO-9942464 A1 * | 8/1999 | ............ | C07D 471/14 |
| WO | 2000024710 A1 | 5/2000 | | |
| WO | WO-0179209 A2 * | 10/2001 | ............ | C07D 513/04 |
| WO | WO-03099011 A1 * | 12/2003 | ......... | A61K 31/7048 |
| WO | WO-2005090295 A2 * | 9/2005 | ............ | C07D 295/13 |
| WO | 2010031835 A2 | 3/2010 | | |
| WO | 2010056753 A1 | 5/2010 | | |
| WO | WO-2011042466 A1 * | 4/2011 | .............. | A61P 43/00 |

OTHER PUBLICATIONS

Abbott et al., "Microalbuminuria in Non—Insulin-Dependent Diabetes Mellitus Implications for Renal Survival" Arch. Internal Med. 154:146-153 (1994).

Adler et al., "Development and progression of nephropathy in type 2 diabetes: The United Kingdom Prospective Diabetes Study (UKPDS 64)", Kidney International, 63: 225-232 (2003).

Allegretti et al., "Allosteric modulation of chemoattractant receptors." Frontiers in Immunology 7(17)1-9 (2016).

Bertini et al., Noncompetitive allosteric inhibitors of the inflammatory chemokine receptors CXCR1 and CXCR2: Prevention of reperfusion injury Proc Nat Acad Sci USA 101: 11791-11796 (2004).

(Continued)

*Primary Examiner* — Sarah Pihonak
(74) *Attorney, Agent, or Firm* — Nixon Peabody LLP; David S. Resnick; Jeanne Jodoin

(57) ABSTRACT

Embodiments herein disclose methods relating to diabetic nephropathy (DN); methods for preventing the onset and also for preventing the progressing of DN, as well as the treatment of DN in diabetic subjects comprising administering reparixin and/or ladarixin which are inhibitors of CXCL8 receptor CXCR1 and CXCR2 activation.

20 Claims, 12 Drawing Sheets

(56) References Cited

OTHER PUBLICATIONS

Citro et al., "CXCR1/2 Inhibition Blocks and Reverses Type 1 Diabetes in Mice", Diabetes 64:1329-1340 (2015).
NIH National Institute of Health, Database of Genotypes and Phenotypes (dbGaP)—Genetic Study on Nephropathy in Type-2 Diabetes. Accession No. phs000302.v1.p1 (2007). Accessible on the world wide web at ncbi.nlm.nih.gov/projects/gap/cgi-bin/study.cgi?study_id=phs000302.v1.p1 retrieved Apr. 15, 2019.
Demetz et al., "Tissue Factor-Factor VIIa complex induces cytokine expression in coronary artery smooth muscle cells" Atherosclerosis 212: 466-471 (2010).
Doria et al., "Can existing drugs approved for other indications retard renal function decline in patients with type 1 diabetes and nephropathy?" Semin Nephrol. 32(5): 437-444 (2012).
Ene et al., "Interleukin-8 and diabetic nephropathy." HVM Bioflux 7(4): 370-374 (2015).
Fincham et al., "Neutrophil chemoattractant and IL-1-like activity in samples from psoriatic skin lesions. Further characterization" J Immunol, 140: 4294-4299 (1988).
Fiorina et al., "Role of Podocyte B7-1 in Diabetic Nephropathy", J. Am. Soc. Nephrol. 25: 1415-1429 (2014).
Griffin et al., "Clinical and Histologic Heterogeneity of Psoriatic Plaques" Arch Dermatol, 124: 216-220 (1988).
Herder et al., "Inflammation and Type 2 Diabetes: Results from KORA Augsburg" Gesundheitswesen 67: 115-121 (2005).
Huber et al., "Expression of functional CCR and CXCR chemokine receptors in podocytes." The Journal of Immunology 168(12): 6244-6252 (2002).
Jeffery "Structural and inflammatory changes in COPD: a comparison with asthma", Thorax, 53:129-136 (1998).
Mauer et al., "Structural-functional relationships in diabetic nephropathy" J Clin Invest, 74: 1143-1155 (1984).
Lefer et al., "Cardioprotective and endothelial protective effects of [Ala-IL8]77 in a rabbit model of myocardial ischaemia and reperfusion", Br J Pharmacol,103:1153-1159 (1991).
Lewis et al., "The Effect of Angiotensin-Converting-Enzyme Inhibition on Diabetic Nephropathy", N Engl J Med 329:1456-1462(1993).
Liu et al., "A major role for neutrophils in experimental bullous pemphigoid", JCI 100:1256-1263 (1997).
USRDS United States Renal Data System "National Institutes of Health, National Institute of Diabetes and Digestive and Kidney Diseases. United States Renal Data System. 2015 USRDS annual data report: Epidemiology of Kidney Disease in the United States" (2015).
Orchard et al., "In the absence of renal disease, 20 year mortality risk in type 1 diabetes is comparable to that of the general population: a report from the Pittsburgh Epidemiology of Diabetes Complications Study", Diabetologia 53: 2312-2319 (2010).
Pesci et al., "Inflammatory cells and mediators in bronchial lavage of patients with chronic obstructive pulmonary disease" Eur Respir J. 12: 380-386 (1998).
Romson et al., "Reduction of the extent of ischemic myocardial injury by neutrophil depletion in the dog", Circulation, 67: 1016-1023 (1983).
Russo et al., "The CXCL8/IL8 chemokine family and its receptors in inflammatory diseases", Expert Rev. Clin. Immunol. 10, 593-619 (2014).
Schumann et al., "The Fas pathway is involved in pancreatic beta cell secretory function", Proc. Natl. Acad. Sci. 104: 2861-2866 (2007).
Sekido et al., "Prevention of lung reperfusion injury in rabbits by a monoclonal antibody against interleukin-8", Nature 365: 654-657 (1993).
Spranger et al., "Inflammatory cytokines and the risk to develop type 2 diabetes: results of the prospective population-based European Prospective Investigation into Cancer and Nutrition (EPIC)-Potsdam Study" Diabetes 52, 812-817 (2003).
Takematsu et al., "Quantification of Chemotactic Peptides (C5a Anaphylatoxin and IL-8) in Psoriatic Lesional Skin", Arch Dermatol 129: 74 (1993).
Tang et al., "Activation of Adenosine A2A Receptor Attenuates Inflammatory Response in a Rat Model of Small-for-Size Liver Transplantation" Transplant. Proc., 42, 1915-1920 (2010).
Tashiro et al., "Urinary levels of monocyte chemoattractant protein—1 (MCP-1) and interleukin—8 (IL-8), and renal injuries in patients with type 2 diabetic nephropathy", J Clin Lab Anal 16: 1-4 (2002).
Tuttle et al., "Diabetic Kidney Disease: A Report From an ADA Consensus Conference", Am. J. Kidney Dis., 64: 510-533 (2014).
Walz et al., "Purification and amino acid sequencing of NAF, a novel neutrophil-activating factor produced by monocytes" Biochem. Biophys. Res. Commun., 149, 755-761 (1987).
Welbourn et al., "Pathophysiology of ischaemia reperfusion injury: Central role of the neutrophil", Br J Surg, 78: 651-655 (1991).
Wolkow et al., "Association of Urinary Inflammatory Markers and Renal Decline in Microalbuminuric Type 1 Diabetics", J. Am. Soc. Nephrol. 19: 789-797 (2008).
Higurashi et al., "Increased urinary levels of CXCL5, CXCL8 and CXCL9 in patients with Type 2 diabetic nephropathy." Journal of diabetes and its complications 23.3 (2009): 178-184.
Krolewski et al., "Early progressive renal decline precedes the onset of microalbuminuria and its progression to macroalbuminuria." Diabetes care 37.1: 226-234 (2014).
Vaidya et al. "Regression of microalbuminuria in type 1 diabetes is associated with lower levels of urinary tubular injury biomarkers, kidney injury molecule-1, and N-acetyl-β-D-glucosaminidase." Kidney international 79.4: 464-470 (2011).
Ene et al. "Interleukin 8 and diabetic nephropathy." Human and Veterinary Medicine 7(4): 370-374 (2015).
Higure et al., "Possibility of the involvement of CXC chemokines in the progression of diabetic nephropathy and its clinical significance." Diabetes (Japan) 47(extra edition): S.93, Abstract No. I-D7-3 (2004).
Khajehdehi et al. "Oral supplementation of turmeric attenuates proteinuria, transforming growth factor-β and interleukin-8 levels in patients with overt type 2 diabetic nephropathy: a randomized, double-blind and placebo-controlled study." Scandinavian journal of urology and nephrology 45(5): 365-370 (2011).
Wada et al., "Regulation of inflammation by anti-IL-8 antibody administration." Japanese Journal of Inflammation 17 (4): 335-343 (1997).

* cited by examiner

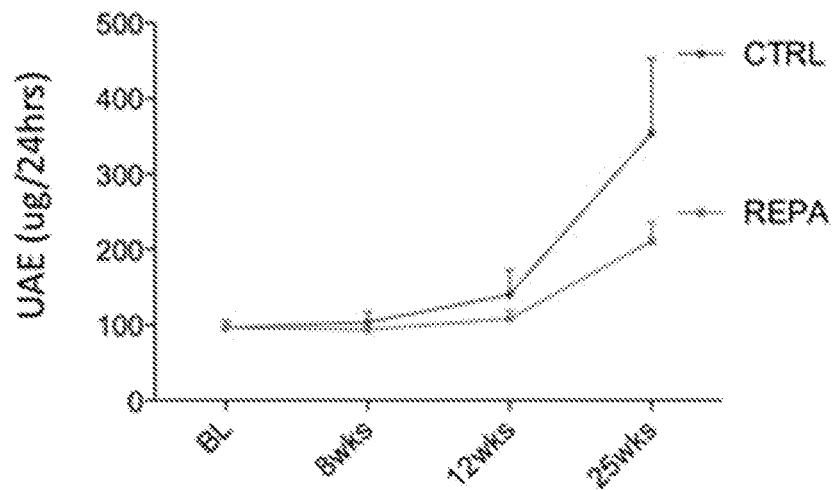
FIG. 1
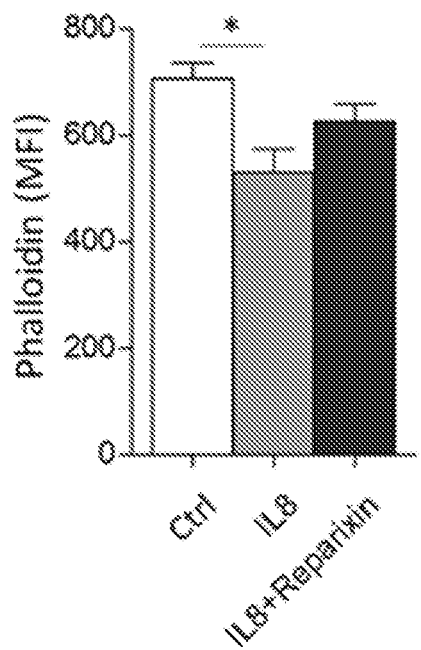 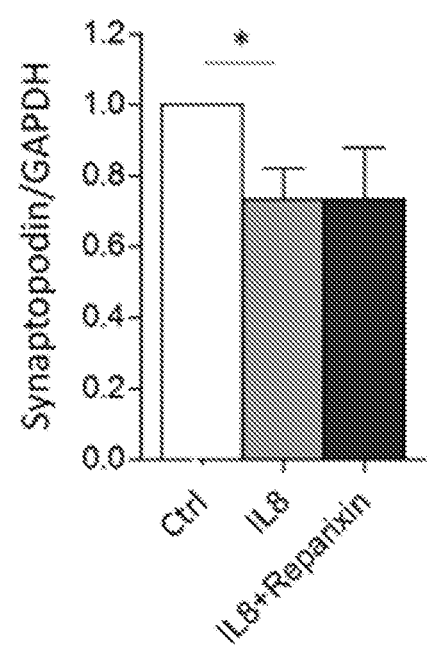
FIG. 2A          FIG. 2B

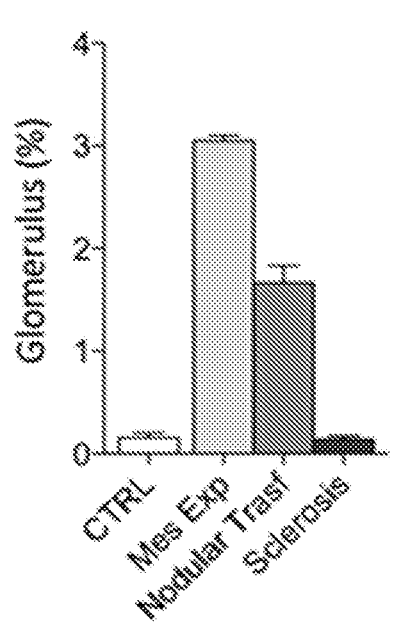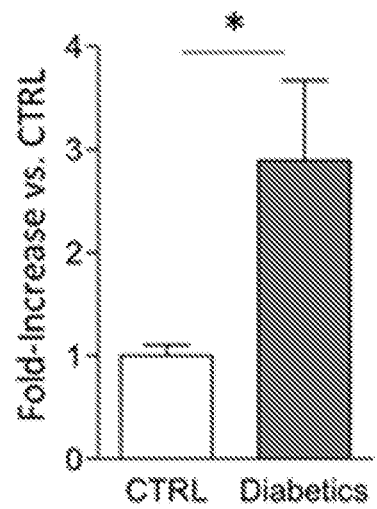
FIG. 3A          FIG. 3B
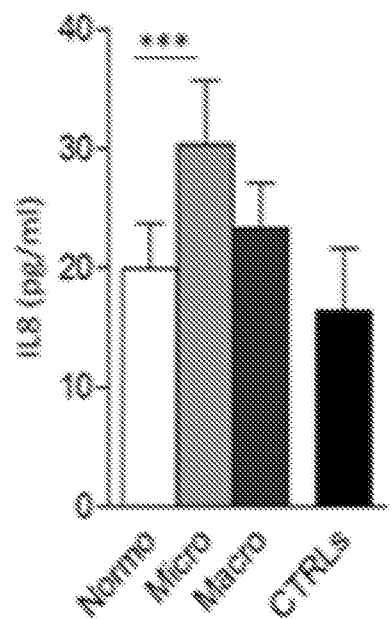
FIG. 4

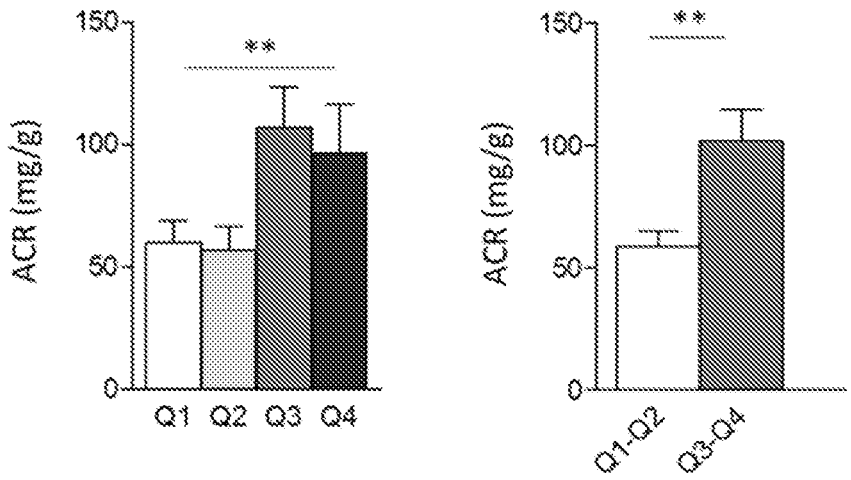
FIG. 5A  FIG. 5B
FIG. 6
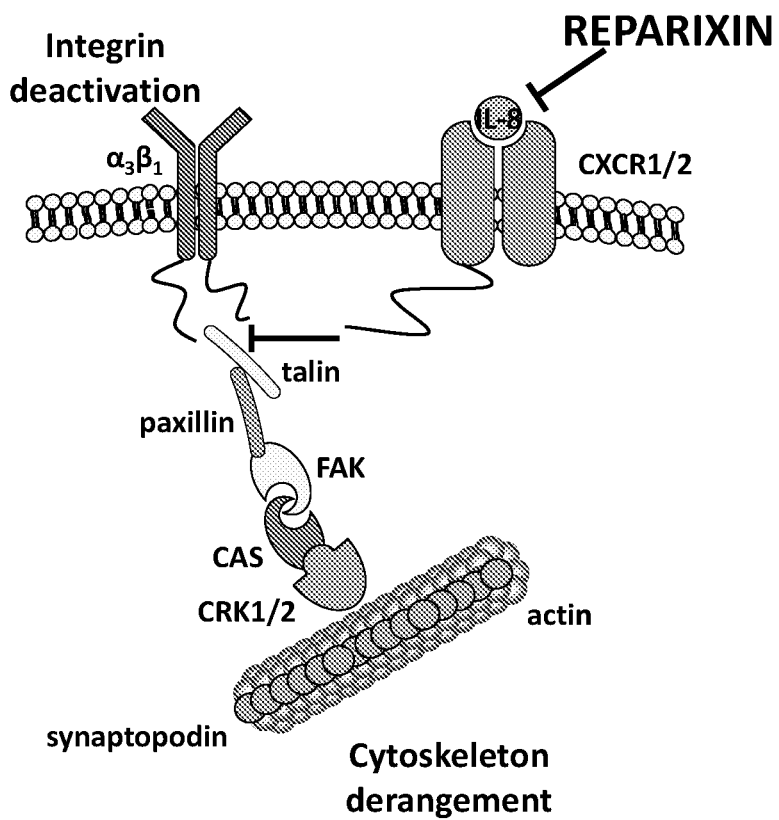

| Histopathological stage | IL-8 expression (score: 0-3) | GFR (ml/min/1.73m²) |
|---|---|---|
| Mesangial expansion | 3.0± 0.0 | 9.43±7.74 |
| Nodular Transformation | 1.5±0.41 | 62.29±6.75 |
| Sclerosis | 0.0±0.0 | 48.25±8.52 |

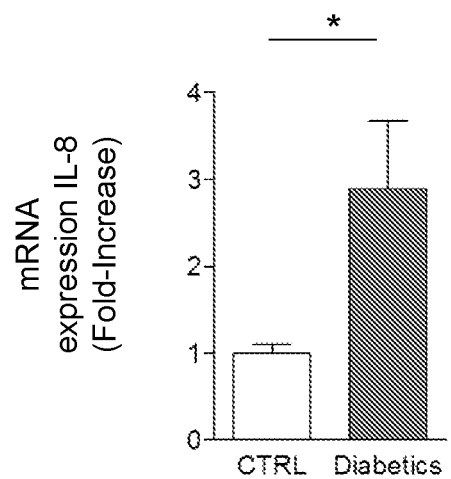
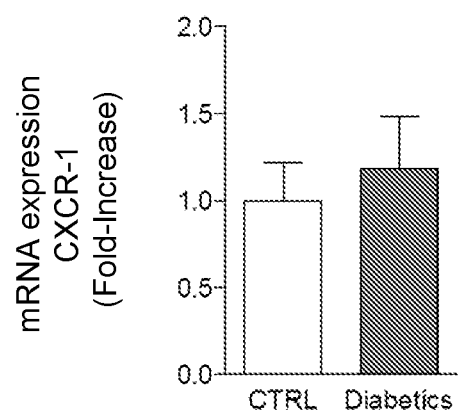
FIG. 7C          FIG. 7D
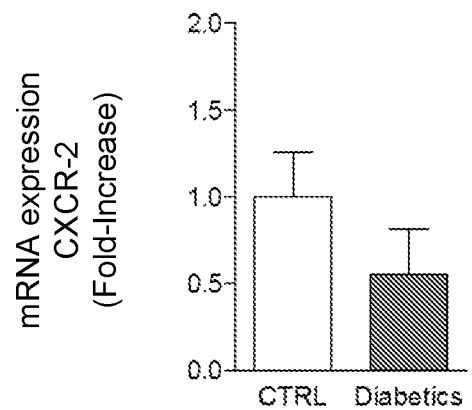
FIG. 7E

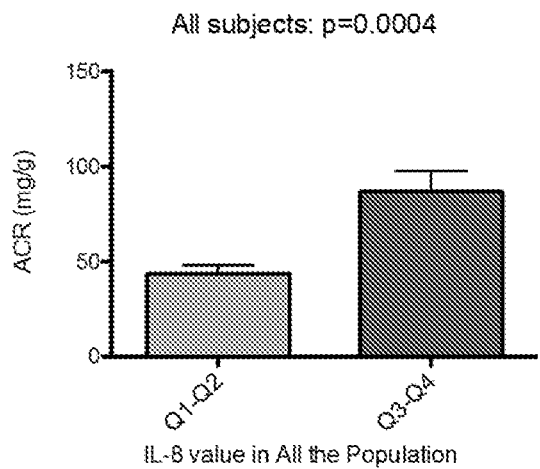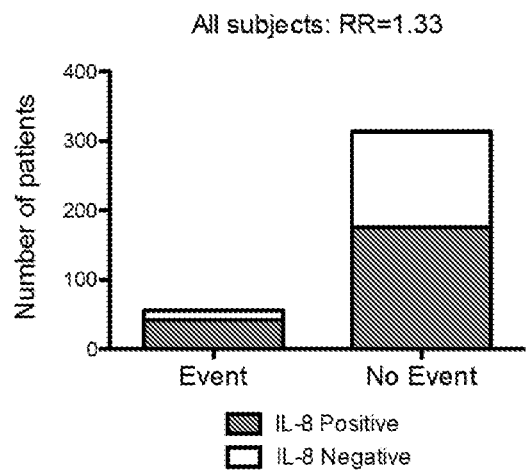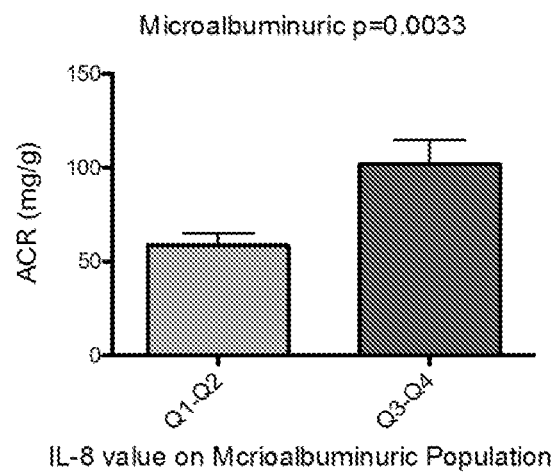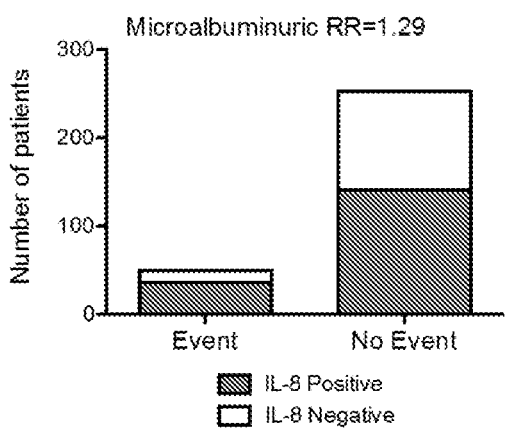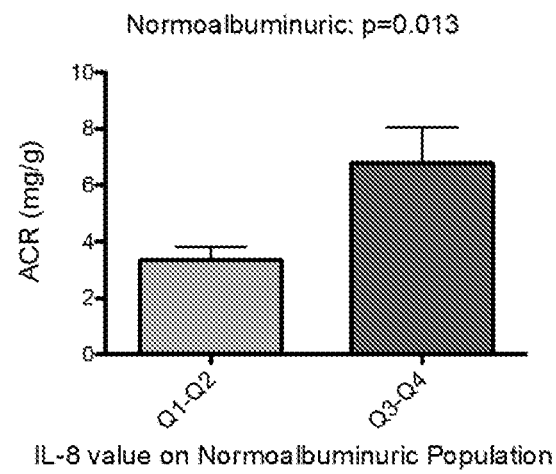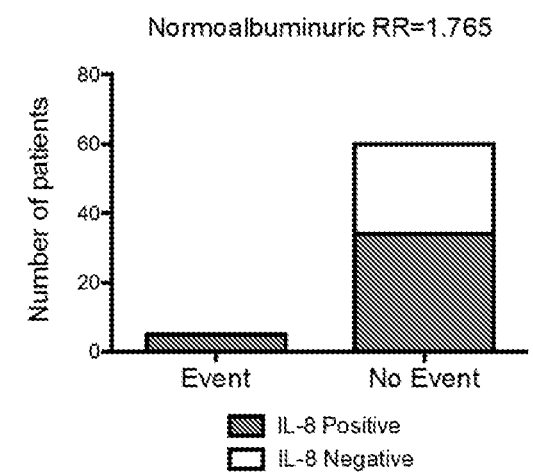
FIG. 8D　　　　　　FIG. 8E

FIG. 8F

|  | IL8 negative | IL8 positive |
|---|---|---|
| Normoalbuminuria | 0 (26) | 5 (39) |
| Microalbuminuria | 14 (126) | 36 (177) |

PREVENTION AND TREATMENT OF DIABETIC NEPHROPATHY

CROSS-REFERENCE TO RELATED APPLICATIONS

This Application is a 35 U.S.C. § 371 National Phase Entry Application of International Application No. PCT/US2017/054916 filed Oct. 3, 2017, which designated the U.S., and which claims benefit under 35 U.S.C. § 119(e) of the U.S. Provisional Application No. 62/403,368 filed Oct. 3, 2016, the contents of which are incorporated herein by reference in their entireties.

FIELD OF THE DISCLOSURE

Embodiments disclosed herein relate to diabetic nephropathy (DN); specifically, the embodiments relate to the methods of prevention and treatment of DN in diabetic subjects.

BACKGROUND

Diabetic nephropathy (DN) is the most common cause of kidney failure and accounts for approximately half of the patients receiving long-term renal dialysis and end-stage renal disease. It is one of the most serious complications faced by diabetic patients, with approximately 40% of prevalence among this patient population. Certain risk factors significantly increase the diabetic patient's likelihood of developing the condition. These include a poor control of blood glucose levels, the length of time having diabetes, the presence of overweight and high blood pressure (over 130/80 mm Hg).

The standard tests for assessing renal function are the measurement of the Glomerular Filtration Rate (GFR), which is the flow rate of filtered fluid through the kidney, and the screening for proteinuria in the urine.

The glomeruli constitute the filtration system of the kidneys, allowing a selective ultrafiltration of the blood plasma into the urine. This barrier is freely permeable to water, small and medium sized solutes, including proteins with a molecular weight lower than albumin, but prevents the passage into urine of bigger molecules and proteins. Any damage to the glomerulari affects the kidneys' ability to control the passage of substances from the blood into the urine.

The filtration apparatus of the glomeruli is structured in three layers: the fenestrated endothelium, the glomerular basement membrane (GBM), and the epithelial podocytes. The function of the glomerular filtration barrier depends on the integrity and functionality of all these three layers.

In normal healthy kidneys less than 0.05% of plasma albumin is found in the urine. This small amount of albumin is filtered at the level of the glomerulus into the urine and is subsequently taken up by proximal tubular cells and degraded. The remaining fragments are reabsorbed into the tubular lumen as albumin fragments.

A number of pathophysiological elements associated to diabetes induce a damage to the glomeruli and, as a consequence, to the filtration system, resulting into the urinary excretion of proteins, in particular albumin, into the urine. A raised level of albumin in the urine is thus the first sign that the kidneys have been damaged by diabetes. The proteins present in the urine then cause damage to the renal tubules and loss of nephrons.

DN is divided into two main stages, depending on how much albumin is lost through the kidneys: microalbuminuria and macroalbuminuria. Microalbuminuria is characterized by an amount of albumin flowing into the urine between 30 and 300 mg per day. It is sometimes called incipient nephropathy. Macroalbuminuria is characterized by an amount of flowing albumin greater than 300 mg per day.

Microalbuminuria is usually the first sign that DN has developed. However, it is not necessarily associated to progression to macroalbuminuria and loss of renal function. In the majority, microalbuminuria may revert to normoalbuminuria but it can also persist at about the same level or progress to macroalbuminuria. On the contrary, once macroalbuminuria has developed, the condition is irreversible and leads to a decline of the glomerular filtration rate (GFR) towards end-stage kidney failure. Once the patient is at this stage of disease, an irreversible damage occurs to the structure of the glomeruli.

The disruption of the glomerular filtration barrier is associated with a number of histopathological changes in the glomeruli. Structural abnormalities of diabetic nephropathy are similar in type 1 and 2 diabetic patients. The earliest morphological change in DN is mesangial expansion, due to an increase in the number of mesangial cells and in mesangial matrix synthesis and a decrease in its degradation. Podocytes and endothelial cells appear to play a role in this process by stimulating mesangial cells to react by increasing mesangial matrix deposition. As the disease progresses, the mesangial matrix and cells continue to accumulate leading to a thickening of the glomerular basement membrane and the development of a number of sclerotic nodules (nodular transformation) that ultimately leads to glomerulosclerosis. By the time these structural lesions lead to a functional impairment, they are quite advanced and current treatments can slow down but cannot arrest progression towards end stage renal disease (ESRD) (Mauer et al, J Clin Invest 1984, 74: 1143; Lewis et al, N Engl J Med 1993, 329: 1456).

It is therefore important to identify therapeutic strategies able to intervene on the early causes of disruption of the glomerular structure and function, before irreversible damage to the glomerular filtration system has occurred and the consequent overt signs or symptoms of renal disease (such as macroalbuminuria and/or decreased GFR) are present.

The current treatments for diabetic nephropathy aim at preventing or delaying the progression of the disease to kidney failure, mainly by reducing factors that are known to significantly increase the diabetic patient's likelihood of developing the pathology, such as cardiovascular diseases, poor control of blood glucose level, and high blood pressure. However, despite the overall improvement of the treatments in the past few years, these have demonstrated a limited effectiveness as evidenced by the increasing number of patients that ultimately develop diabetic nephropathy. Recent studies focused on the development of potential novel therapies that target pathways believed to promote the progression of renal disease such as inhibitors of advanced glycation end-products (AGEs), protein kinase C, vitamin D, or endothelin 1. However, these potentially alternative therapies have not yet been successfully translated into the clinical practice.

Interleukin-8 (IL8; CXCL8) is considered a major mediator of PMN (Polymorphonuclear Neutrophils) recruitment and is involved in several pathologies, including psoriasis, rheumatoid arthritis, chronic obstructive pulmonary disease, and ischemia/reperfusion injury in transplanted organ (Griffin et al, Arch Dermatol 1988, 124: 216; Fincham et al, J Immunol 1988, 140: 4294; Takematsu et al, Arch Dermatol 1993, 129: 74; Liu et al, 1997, 100:1256; Jeffery, Thorax 1998, 53: 129; Pesci et al, Eur Respir J. 1998, 12: 380; Lafer et al, Br J Pharmacol. 1991, 103: 1153; Romson et al, Circulation 1993, 67: 1016; Welbourn et al, Br J Surg. 1991, 78: 651; Sekido et al, Nature 1993, 365, 654). The biological activity of IL8 is mediated by the interaction with two receptors, CXCR1 and CXCR2, belonging to the 7TM-GPCR family, that are expressed on the surface of human PMNs.

A number of studies evidence that urinary levels of IL8 are increased in microalbuminuric patients, thus suggesting a potential use of IL8, in combination with at least another marker such as IP-10, IL-6, MIP-1δ or MCP1, in prognostic methods to identify the population of microalbuminuric patients that could undergo a progressive renal function decline (Tashiro et al, J Clin Lab Anal 16: 1-4, 2002).

Reparixin and Ladarixin are noncompetitive allosteric inhibitors of CXCR1 and CXCR2, cognate receptors of IL8 (CXCL8), able to (Bertini, R., et al. Proc Nat Acad Sci USA 2004, 101: 11791) block a range of activities related to IL8 signaling, including leukocyte recruitment and other inflammatory responses, without affecting the binding between the ligand and the receptor (Bertini, R., et al. Proc Nat Acad Sci USA 2004, 101: 11791).

Reparixin is the INN name of R(−)-2-[(4-isobutylphenyl) propionyl]-methanesulfonamide (previously known as Repertaxin or DF 1681Y) and it was first disclosed in International application WO0024710. Further description of reparixin and its usage in the prevention of diabetes is found in the U.S. Patent Application Publication No: US2015/ 0011639. The use of reparixin in reducing or inhibiting graft rejection in an individual having received a pancreatic islet cell transplant are described in the U.S. Patent Application Publication No: US 2012/0202884. However, preventative and therapeutic effects of reparixin for diabetic nephropathy have not been suggested or explored. Uses of reparixin for cancer treatment are described in WO2010/056753. The contents of each of these patents are incorporated herein by reference in their entirety.

Ladarixin is the INN name of R(−)-2-[(4'-trifluoromethanesulfonyloxy)phenyl]propionyl-methanesulfonamide sodium salt (previously known as Meraxin or DF2156A). It has been demonstrated that CXCR1 and CXCR2 inhibition by Ladarixin is able to block and revert type 1 diabetes in mice. (Citro A. et al., Diabetes 2015, 64:1329).

(2S)-2-(4-{[4-(trifluoromethyl)-1,3-thiazol-2-yl] amino} phenyl) propanoic acid (also known as DF2755Y) and its sodium salt (also known as DF2755A) is a potent and selective dual inhibitor of CXCR1 and CXCR2-triggered PMN activity, which was first disclosed in WO2010/031835 which also discloses its use in the treatment of IL8-dependent pathologies such as transient cerebral ischemia, bullous pemphigoid, rheumatoid arthritis, idiopathic fibrosis, glomerulonephritis and damages caused by ischemia/reperfusion.

The present inventors have now demonstrated the therapeutic efficacy of IL8 inhibitors in preventing proteinuria under diabetic conditions and protecting kidneys against the onset and progression of diabetic nephropathy (DN). They have also demonstrated that IL8 is involved in the early histopathological changes responsible for the onset of renal disease.

SUMMARY

In particular, embodiments of the present disclosure are based on experimental demonstration of the therapeutic efficacy of reparixin in preventing and/or reverting mesangial expansion and podocytes injury under diabetic conditions and protecting against the further development and progression of diabetic nephropathy (DN).

Accordingly, it is a first object of the present disclosure to provide methods for treatment of diabetic nephropathy or for prevention, reduction of the risk or delay of the onset or progression of diabetic nephropathy, comprising administering an IL8 inhibitor, preferably a CXCR1 and/or CXCR2 inhibitor, more preferably a CXCR1 and CXCR2 inhibitor and, even more preferably, a compound selected from R(−)-2-[(4-isobutylphenyl)propionyl]-methanesulfonamide (hereinbelow referred to as reparixin), or a salt thereof, preferably its lysine salt, R(−)-2-[(4'-trifluoromethane sulfonyloxy)phenyl]-N-methanesulfonyl propionamide (hereinbelow referred to as ladarixin) or a salt thereof, preferably its sodium salt and (2S)-2-(4-{[4-(trifluoromethyl)-1,3-thiazol-2-yl] amino} phenyl) propanoic acid (hereinbelow referred to as DF2755Y), or a salt thereof, preferably its sodium salt (hereinbelow referred to as DF2755A) to a subject in need thereof.

A second object of this disclosure is to provide uses of an IL8 inhibitor, preferably a CXCR1 and/or CXCR2 inhibitor, more preferably a CXCR1 and CXCR2 inhibitor and, even more preferably, a compound selected from R(−)-2-[(4-isobutylphenyl)propionyl]-methanesulfonamide (hereinbelow referred to as reparixin), or a salt thereof, preferably its lysine salt, R(−)-2-[(4'-trifluoromethane sulfonyloxy)phenyl]-N-methanesulfonyl propionamide (hereinbelow referred to as ladarixin) or a salt thereof, preferably its sodium salt and (2S)-2-(4-{[4-(trifluoromethyl)-1,3-thiazol-2-yl]amino} phenyl) propanoic acid (hereinbelow referred to as DF2755Y), or a salt thereof, preferably its sodium salt (hereinbelow referred to as DF2755A), to treat diabetic nephropathy or to prevent, reduce the risk or delay the onset or progression of diabetic nephropathy in a subject.

A third object of this disclosure is to provide uses of an IL8 inhibitor, preferably a CXCR1 and/or CXCR2 inhibitor, more preferably a CXCR1 and CXCR2 inhibitor and, even more preferably, a compound selected from R(−)-2-[(4-isobutylphenyl)propionyl]-methanesulfonamide (hereinbelow referred to as reparixin) or a salt thereof, preferably its lysine salt, R(−)-2-[(4'-trifluoromethane sulfonyloxy)phenyl]-N-methanesulfonyl propionamide (hereinbelow referred to as ladarixin) or a salt thereof, preferably its sodium salt and (2S)-2-(4-{[4-(trifluoromethyl)-1,3-thiazol-2-yl]amino} phenyl) propanoic acid (hereinbelow referred to as DF2755Y), or a salt thereof, preferably its sodium salt (hereinbelow referred to as DF2755A), for the manufacture of a medicament to treat diabetic nephropathy or to prevent, reduce the risk or delay the onset or progression of diabetic nephropathy in a subject.

A fourth object of this disclosure is to provide an IL8 inhibitor, preferably a CXCR1 and/or CXCR2 inhibitor, more preferably a CXCR1 and CXCR2 inhibitor and, even more preferably, a compound selected from R(−)-2-[(4-isobutylphenyl)propionyl]-methanesulfonamide (hereinbelow referred to as reparixin) or a salt thereof, preferably its lysine salt, R(−)-2-[(4'-trifluoromethane sulfonyloxy)phenyl]-N-methanesulfonyl propionamide (hereinbelow referred to as ladarixin) or a salt thereof, preferably its sodium salt and (2S)-2-(4-{[4-(trifluoromethyl)-1,3-thiazol-2-yl] amino} phenyl) propanoic acid (hereinbelow referred to as DF2755Y)) or a salt thereof, preferably its sodium salt (hereinbelow referred to as DF2755A), for the use in the treatment of diabetic nephropathy or in the prevention, reduction of the risk or delay of the onset or progression of diabetic nephropathy in a subject.

A fifth object of this disclosure is to provide a method of treatment comprising determining the level of IL8 in a urine same from a subject, and administering to the subject an effective amount of Reparixin and/or Ladarixin when a IL8 levels are at least 3-fold greater than a reference level.

A sixth object of this disclosure is to provide a method of treating hyperglycemia comprising diagnosing a subject with hyperglycemia and administering an effective amount of Reparixin and/or Ladarixin to the subject.

A seventh object of this disclosure is to provide a method of treating hyperglycemia comprising administering to a patient in need thereof an effective amount of Reparixin and/or Ladarixin.

An eighth object of this disclosure is to provide a composition comprising, or consisting, or consisting essentially of Reparixin and/or Ladarixin for treating diabetic nephropathy, or preventing, or reducing the risk, or delaying the onset or progression of diabetic nephropathy in a subject. In one embodiment, a composition comprising, or consisting, or consisting essentially of Reparixin and/or Ladarixin is administered for treating diabetic nephropathy, or preventing, or reducing the risk, or delaying the onset or progression of diabetic nephropathy in a subject, wherein the subject has IL8 levels higher than 2.4 pg/ml. In one embodiment, a composition comprising, or consisting, or consisting essentially of Reparixin and/or Ladarixin is administered for treating diabetic nephropathy, or preventing, or reducing the risk, or delaying the onset or progression of diabetic nephropathy in a subject, wherein the subject has a IL8 level 3-fold greater than a reference level.

A ninth object of this disclosure is to provide a composition comprising, or consisting, or consisting essentially of Reparixin and/or Ladarixin for the manufacture of a medicament for treating diabetic nephropathy, or preventing, or reducing the risk, or delaying the onset or progression of diabetic nephropathy in a subject.

A tenth object of this disclosure is to provide a use of a composition comprising, or consisting, or consisting essentially of Reparixin and/or Ladarixin for treating diabetic nephropathy, or preventing, or reducing the risk, or delaying the onset or progression of diabetic nephropathy in a subject.

An eleventh object of this disclosure is to provide a use of a composition comprising, or consisting, or consisting essentially of Reparixin and/or Ladarixin for the manufacture of a medicament for treating diabetic nephropathy, or preventing, or reducing the risk, or delaying the onset or progression of diabetic nephropathy in a subject.

Accordingly, in one embodiment of each of the above objects of the invention, in said method or use the subject has been diagnosed with diabetes.

Accordingly, in one embodiment of each of the above objects of the invention, in said method or use the subject has been diagnosed with Type 1 diabetes.

Accordingly, in one embodiment of each of the above objects of the invention, in said method or use the subject has been diagnosed with Type 2 diabetes.

According to another embodiment of each of the above objects of the invention, also in combination with any of the previous embodiments, in said method or use the subject has microalbuminuria.

According to another embodiment of each of the above objects of the invention, also in combination with any of the previous embodiments, in said method or use the subject has a urinary level of IL8 higher than an IL8 reference standard. Preferably said reference standard is the urinary IL8 level of healthy individuals not having any nephropathy.

According to another embodiment of each of the above objects of the invention, also in combination with any of the previous embodiments, in said method or use the subject has a urinary level of IL8 higher than 2.41 pg/ml.

According to a further embodiment of each of the above objects of the invention, also in combination with any of the previous embodiments, in said method or use the subject has a value of GFR (glomerular filtration rate) above 60 ml/min/1.73m2, preferably above 90 ml/min/1.73m2.

According to a further embodiment of each of the above objects of the invention, also in combination with any of the previous embodiments, the subject has at least one of the following single nucleotide polymorphisms at the CXCR1 locus: s13006838, rs4674308; rs4674309; rs3755042; rs7601872; and rs664514.

In one embodiment of the first object of the invention, also in combination with any of the previous embodiments, provided herein is a method for treatment of diabetic nephropathy or for prevention, reduction of the risk or delay of the onset or progression of diabetic nephropathy, the method comprising: (a) measuring the level of IL8 in a sample obtained from the subject; (b) comparing the measured IL8 level with an IL8 reference; and (c) administering an IL8 inhibitor, preferably a CXCR1 and/or CXCR2 inhibitor, more preferably a CXCR1 and CXCR2 inhibitor and, even more preferably, a compound selected from R(−)-2-[(4-isobutylphenyl)propionyl]-methanesulfonamide (hereinbelow referred to as reparixin) or a salt thereof, preferably its lysine salt, R(−)-2-[(4'-trifluoromethane sulfonyloxy)phenyl]-N-methanesulfonyl propionamide (hereinbelow referred to as ladarixin) or a salt thereof, preferably its sodium salt, and (2S)-2-(4-{[4-(trifluoromethyl)-1,3-thiazol-2-yl] amino} phenyl) propanoic acid (hereinbelow referred to as DF2755Y), or a salt thereof, preferably its its sodium salt (hereinbelow referred to as DF2755A) to the subject when the measured IL8 level is above an IL8 reference, wherein said IL8 reference is the mean urinary IL8 level of a statistically significant number of non-diabetic individuals not having any nephropathy, and not having an inflammatory disease.

In another embodiment of the first object of the invention, also in combination with any of the previous embodiments, provided herein is a method for treatment of diabetic nephropathy or for prevention, reduction of the risk or delay of the onset or progression of diabetic nephropathy in a subject, the method comprising: (a) measuring the level of IL8 in a sample obtained from the subject; and (b) administering an IL8 inhibitor, preferably a CXCR1 and/or CXCR2 inhibitor, more preferably a CXCR1 and CXCR2 inhibitor and, even more preferably, a compound selected from R(−)-2-[(4-isobutylphenyl)propionyl]-methanesulfonamide (hereinbelow referred to as reparixin) or a salt thereof, preferably its lysine salt, R(−)-2-[(4'-trifluoromethane sulfonyloxy)phenyl]-N-methanesulfonyl propionamide (hereinbelow referred to as ladarixin) or a salt thereof, preferably its sodium salt and (2S)-2-(4-{[4-(trifluoromethyl)-1,3-thiazol-2-yl] amino} phenyl) propanoic acid (hereinbelow referred to as DF2755Y) or a salt thereof, preferably its sodium salt (herein below referred to as DF2755A) to the subject when the measured IL8 level is above 2.41 pg/ml.

In another embodiment of the first object of the invention, also in combination with any of the previous embodiments, is a method for treatment of diabetic nephropathy or for prevention, reduction of the risk or delay of the onset or progression of diabetic nephropathy in a subject, the method comprising: (a) determining whether the subject has at least one of the following single nucleotide polymorphisms (SNPs) at the CXCR1 locus: s13006838, rs4674308; rs4674309; rs3755042; rs7601872; and rs664514; and (b) administering an IL8 inhibitor, preferably a CXCR1 and/or CXCR2 inhibitor, more preferably a CXCR1 and CXCR2 inhibitor and, even more preferably, a compound selected from R(−)-2-[(4-isobutylphenyl)propionyl]-methanesulfonamide (hereinbelow referred to as reparixin) or a salt thereof, preferably its lysine salt R(−)-2-[(4'-trifluoromethane sulfonyloxy)phenyl]-N-methanesulfonyl propionamide (hereinbelow referred to as ladarixin) or a salt thereof, preferably its sodium salt and (2S)-2-(4-{[4-(trifluoromethyl)-1,3-thiazol-2-yl] amino} phenyl) propanoic acid (hereinbelow referred to as DF2755Y) or a salt thereof, preferably its sodium salt (hereinbelow referred to as DF2755A), to the subject when the subject has at least one of the said SNPs.

In one embodiment of the first object of the invention, also in combination with any of the previous embodiments, the method further comprises measuring the protein level in a sample of urine from the subject.

In one embodiment of the first object of the invention, also in combination with any of the previous embodiments, the method further comprises selecting subject having microalbuminuria.

In one embodiment of the first object of the invention, also in combination with any of the previous embodiments, the method further comprises obtaining a sample of urine from the subject for urine protein level analysis.

In one embodiment of the first object of the invention, also in combination with any of the previous embodiments, the method further comprises comparing the measured level of protein level with a urine protein reference.

In one embodiment of the first object of the invention, also in combination with any of the previous embodiments, the first reference is the level of protein in urine samples obtained in normal healthy subjects that do not have any nephropathy.

In one embodiment of any method or use described above, the subject has normal proteinuria or increased proteinuria.

In one embodiment of the first object of the invention, also in combination with any of the previous embodiments, the method further comprises measuring the IL8 level in a sample obtained from the subject.

In one embodiment of any method or use described above, the sample is a urine, blood, serum or plasma sample.

In one embodiment of the first object of the invention, also in combination with any of the previous embodiments, the method further comprises comparing the measured IL8 level with an IL8 reference level.

In one embodiment of any method or use described above, the IL8 reference level is the IL8 level in the respective samples obtained in normal healthy subjects that do not have any nephropathy.

In one embodiment of any method or use described above, the IL8 reference level is the IL8 level in the respective samples obtained in normal healthy subjects that do not have any nephropathy or any inflammation conditions.

In one embodiment of the first object of the invention, also in combination with any of the previous embodiments, the method further comprises selecting subjects wherein the measured IL8 level in the urine is higher than 2.41 pg/ml.

In one embodiment of the first object of the invention, also in combination with any of the previous embodiments, the method further comprises determining whether the subject has at least one of the following single nucleotide polymorphisms at the CXCR1 locus: s13006838, rs4674308; rs4674309; rs3755042; rs7601872; and rs664514.

BRIEF DESCRIPTION OF THE DRAWINGS

FIG. 1 presents experimental data showing urinary albumin excretion levels, measured as pg in 24 hours, in control mice (CTRL) and mice treated with reparixin (REPA) as described in Example 2.

FIG. 2A presents experimental data showing the quantification of actin expression as measured by phalloidin staining in control (CTRL), IL8-treated (IL8) and IL8- and reparixin-treated podocytes cells (IL-.reparixin).

FIG. 2B presents experimental data showing synaptopodin mRNA expression controlled for GAPDH mRNA expression as measured in in control (CTRL), IL8 treated (IL8) and IL8 and reparixin treated podocytes cells (IL8 reparixin).

FIG. 3A presents experimental data quantifying the expression of IL8, expressed as percentage of glomerular area, in patients with mesangial expansion (Mes Exp), nodular transformation (Nodular Transf) or glomerulosclerosis (Sclerosis).

FIG. 3B presents experimental data showing the level of expression of IL8 measured by quantitative PCR on glomeruli of control individuals and patients with type 2 diabetes and DN, represented as fold increase vs control.

FIG. 4 presents experimental data showing mean urinary IL8 levels measured in T2D normoalbuminuric (Normo), microalbuminuric (Micro), macroalbuminuric (Macro) or in control (CTRLs) patients.

FIG. 5A presents experimental data showing mean ACR values in patients wherein the expression of IL8 corresponds to either the first (Q1), second (Q2), third (Q3) or fourth (Q4) quartile;

FIG. 5B presents experimental data showing ACR values in patients having a IL8 expression below (Q1-Q2) or above (Q3-Q4) the median value.

FIG. 6 presents a model showing the mechanism by which Reparixin is functioning to prevent cytoskeletal remodeling.

FIG. 7C presents experimental data showing the fold increase of IL8 mRNA expression in diabetic samples compared to control. mRNA levels were analyzed by RT-PCR.

FIG. 7D presents experimental data showing the fold increase of CXCR-1 mRNA expression in diabetic samples compared to control. mRNA levels were analyzed by RT-PCR.

FIG. 7E presents experimental data showing the fold increase of CXCR-2 mRNA expression in diabetic samples compared to control. mRNA levels were analyzed by RT-PCR.

FIG. 8D presents experimental data showing of all the 389 patients and its subsets of normoalbuminuric and microalbuminuric, those patients who were above the median distribution of IL8 in the normo and microalbuminuric cohort, showed an ACR significantly higher than those from below the median.

FIG. 8E presents experimental data showing the event risk of all the 389 patients and its subsets of normoalbuminuric and microalbuminuric.

FIG. 8F presents a chart showing IL8 expression in normoalbuminuric and microalbuminuric subsets.

DETAILED DESCRIPTION

Figures 7A, 7B:
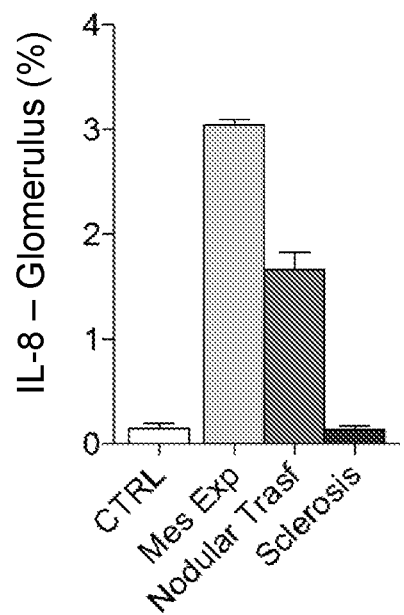
FIGS. 7A and 7B present experimental data showing IL8 expression has a peak in early injury phases and progressively decreases following the loss of cellularity of the kidney parenchyma and the onset of fibrosis.

Unless otherwise explained, all technical and scientific terms used herein have the same meaning as commonly understood by one of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims.

Definitions of common terms in molecular biology can be found in The Merck Manual of Diagnosis and Therapy, 19th Edition, published by Merck Sharp & Dohme Corp., 2011 (ISBN 978-0-911910-19-3) or the 2015 digital online edition at merckmanuals.com; Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties. Further, unless otherwise required by context, singular terms shall include pluralities and plural terms shall include the singular.

Unless otherwise stated, the present invention was performed using standard procedures known to one skilled in the art, for example, in Michael R. Green and Joseph Sambrook, Molecular Cloning: A Laboratory Manual, Cold Spring Harbor Laboratory Press, Cold Spring Harbor, N.Y., USA (2012); Davis et al., Basic Methods in Molecular Biology, Elsevier Science Publishing, Inc., New York, USA (1986); Current Protocols in Molecular Biology (CPMB) (Fred M. Ausubel, et al. ed., John Wiley and Sons, Inc.), Current Protocols in Immunology (CPI) (John E. Coligan, et. al., ed. John Wiley and Sons, Inc.), Current Protocols in Cell Biology (CPCB) (Juan S. Bonifacino et. al. ed., John Wiley and Sons, Inc.), Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998), Methods in Molecular biology, Vol. 180, Transgenesis Techniques by Alan R. Clark editor, second edition, 2002, Humana Press, and Methods in Molecular Biology, Vo. 203, 2003, Transgenic Mouse, edited by Marten H. Hofker and Jan van Deursen, which are all herein incorporated by reference in their entireties.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used in connection with percentages will mean±1%.

All patents and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

As used herein, the term "subject", "individual", "patient", and "person" are used interchangeably to mean a mammal, such as a dog, a cat, a cow, and a horse, and preferably a human.

In one embodiment, the term "pharmaceutically acceptable" means approved by a regulatory agency of the Federal or a state government or listed in the U.S. Pharmacopeia or other generally recognized pharmacopeia for use in animals, and more particularly in humans. Specifically, it refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations, and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences, 18th Ed., Gennaro, ed. (Mack Publishing Co., 1990). The formulation should suit the mode of administration.

As used herein, the term "comprising" or "comprises" is used in reference to methods, and respective component(s) thereof, that are essential to the invention, yet open to the inclusion of unspecified elements, whether essential or not. The use of "comprising" indicates inclusion rather than limitation.

As used herein the term "consisting essentially of" refers to those elements required for a given embodiment. The term permits the presence of elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

The terms "diabetic kidney disease", "DKD", "diabetic nephropathy" and "DN" are used interchangeably herein, refer to any loss of kidney structural integrity and function that results in certain nutrients leaking into the urine instead of being reabsorbed back into the blood, e.g., proteins leaking into the urine.

The terms "disease", or "condition" are used interchangeably herein, refer to any alternation in state of the body or of some of the organs, interrupting or disturbing the performance of the functions and/or causing symptoms such as discomfort, dysfunction, distress, or even death to the person afflicted or those in contact with a person. A disease or disorder can also be related to a distemper, ailing, ailment, malady, disorder, sickness, illness, complaint, or affectation.

The term "in need thereof" when used in the context of a therapeutic or prophylactic treatment, means having a disease, being diagnosed with a disease, or being in need of preventing a disease, e.g., for one at risk of developing the disease. Thus, a subject in need thereof can be a subject in need of treating or preventing a disease.

As used herein, in one embodiment, the phrase "preventing the onset of diabetic nephropathy" means stopping, hindering, and/or slowing down the initial occurrence of more than 30 mg of albumin in the urine of a diabetic subject or a subject having a diabetic condition.

In another embodiment, as used herein, the term "prevent" or "prevention" in the context of the onset of DN and the progression of DN in a diabetic subject or a subject having a diabetic condition refers to stopping, hindering, and/or slowing down the onset of developing adverse effects and symptoms associated with medical conditions that are associated with DN, such as loss of kidney structural integrity and function that results in certain nutrients leaking into the urine instead of being reabsorbed back into the blood, e.g., proteins leaking into the urine.

As used herein, the phrase "preventing the progression of diabetic nephropathy" means stopping, hindering, and/or slowing down the continued occurrence/recurrence of more than 30 mg of albumin per day in the urine of a diabetic subject or a subject having a diabetic condition.

As used herein, in one embodiment, the terms "treat," "treatment," "treating," or "amelioration" refer to therapeutic treatments, wherein the object is to reverse, alleviate, ameliorate, inhibit, slow down or stop the progression or severity of DN and kidney failure. Treatment is generally "effective" if one or more symptoms or clinical markers are reduced. For example, in DN, "effective treatment" refers to a treatment that reduces protein excreted into the urine to the normal protein/albumin range and maintains it within the normal range for at least one week. In one embodiment, treatments described herein can reduce proteinuria and maintain normal ranges of protein/albumin for at least two weeks, at least 3 weeks, at least 4 weeks, at least 5 weeks, at least 6 weeks, at least 7 weeks, at least 8 weeks, at least 9 weeks, at least 10 weeks, at least 11 weeks, at least 12 weeks, at least 13 weeks, at least 14 weeks, at least 15 weeks, at least 16 weeks, at least 17 weeks, at least 18 weeks, or more, e.g, at least 20 weeks (or 5 months), 6 months or more. In another embodiment, treatment is "effective" if the progression of a disease is reduced or halted. That is, "treatment" includes not just the improvement of symptoms or markers, e.g. IL8 or other markers disclosed in U.S. Patent Application Publication No: US 2006/0240437, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality. For example, treatment is considered effective if the condition is stabilized, or the urine protein/albumin levels are normalized. The term "treatment" of a disease also includes providing relief from the symptoms or side-effects of the disease (including palliative treatment).

As used herein, the term "inhibitor" in "an IL8 inhibitor" or "CXCR1 and/or CXCR2 inhibitor" refers to any synthetic/natural organic or organic/inorganic molecule that opposes the naturally occurring signaling events elicited by IL8 chemokine binding to its receptors or CXCR1 and/or CXCR2 activation.

As used herein, the term "administering," refers to the placement of IL8 inhibitors, as disclosed herein into a subject by a method or route that results in at least partial delivery of the agent/drug at a desired site. Pharmaceutical compositions comprising the compounds disclosed herein can be administered by any appropriate route which results in an effective treatment in the subject. "Administering" means oral ("po") administration, administration as a suppository, topical contact, intravenous ("iv"), intraperitoneal ("ip"), intramuscular ("im"), intralesional, intranasal or subcutaneous ("sc") administration, or the implantation of a slow-release device e.g., a mini-osmotic pump, to a subject. Administration is by any route including parenteral and transmucosal (e.g., oral, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

The terms "systemic administration" and "systemically administered" refer to a method of administering a compound or composition to a mammal so that the compound or composition is delivered to sites in the body, including the targeted site of pharmaceutical action, via the circulatory system. Systemic administration includes, but is not limited to, oral, intranasal, rectal and parenteral (i.e., other than through the alimentary tract, such as intramuscular, intravenous, intra-arterial, transdermal and subcutaneous) administration, with the proviso that, as used herein, systemic administration does not include direct administration to the brain region by means other than via the circulatory system, such as intrathecal injection and intracranial administration.

As used herein, in one embodiment, the term "increased proteinuria" means at least 10% increased protein level in a urine sample compared to a urine protein reference level. In another embodiment, "increased proteinuria" means excreting greater than 30 mg of albumin in the urine/24 hr day.

The terms "increased", "increase", or "elevated" are all used herein to generally mean an increase by a statically significant amount; for the avoidance of doubt, the terms "increased", "increase", or "enhance", mean an increase of at least 10% as compared to a reference level, for example an increase of at least about 10%, at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The terms, "decrease", "reduce", "reduction", "lower" or "lowering," or "inhibit" are all used herein generally to mean a decrease by a statistically significant amount. For example, "decrease", "reduce", "reduction", or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g., absent level or non-detectable level as compared to a reference level), or any decrease between 10-100% as compared to a reference level. In the context of a marker or symptom, by these terms is meant a statistically significant decrease in such level. The decrease can be, for example, at least 10%, at least 20%, at least 30%, at least 40% or more, and is preferably down to a level accepted as within the range of normal for an individual without a given disease.

The term "statistically significant" or "significantly" refers to statistical significance and generally means a difference of two standard deviations (2SD) or more.

The term "normalizing" refers to a change in urine protein/albumin levels to within the normal range from an elevated urine protein/albumin level. "Normalizing" refers not only to the activity of promoting a decrease in an abnormally high urine protein/albumin level, but also maintaining such levels for a prolonged period of time, e.g., at least one week for a single unit dose pharmaceutical composition administration as described herein.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like. A pharmaceutically acceptable carrier will not promote the raising of an immune response to an agent with which it is admixed, unless so desired. The preparation of a pharmacological composition that contains active ingredients dissolved or dispersed therein is well understood in the art and need not be limited based on formulation. Typically such compositions are prepared as injectable either as liquid solutions or suspensions, however, solid forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Suitable excipients include, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used in the methods described herein that will be effective in the treatment of a particular disorder or condition will depend on the nature of the disorder or condition, and can be determined by standard clinical techniques. Suitable pharmaceutical carriers are described in Remington's Pharmaceutical Sciences, A. Osol, a standard reference text in this field of art. For example, a parenteral composition suitable for administration by injection is prepared by dissolving 1.5% by weight of active ingredient in 0.9% sodium chloride solution.

In one embodiment, the "pharmaceutically acceptable" carrier does not include in vitro cell culture media.

The terms "sustained release" and "extended release" are used in their conventional sense to refer to a drug formulation that provides for gradual release of a drug over an extended period of time, for example, 12 hours or more, and that preferably, although not necessarily, results in substantially steady-state blood levels of a drug over an extended time period.

As used herein, the term "delayed release" refers to a pharmaceutical preparation that passes through the stomach intact and dissolves in the small intestine.

The terms "controlled release," "sustained release," "extended release," and "timed release" are intended to refer interchangeably to any drug-containing formulation in which release of the drug is not immediate, i.e., with a "controlled release" formulation, oral administration does not result in immediate release of the drug into an absorption pool. The terms are used interchangeably with "nonimmediate release" as defined in Remington: The Science and Practice of Pharmacy, 21st Ed., Lippencott Williams & Wilkins (2006).

As used herein, the term "subtherapeutic dose" refers to a dose of a pharmacologically active agent(s), either as an administered dose of pharmacologically active agent, or actual level of pharmacologically active agent in a subject that functionally is insufficient to elicit the intended pharmacological effect in itself (e.g., to obtain analgesic, anti-convulsant, anti-depressant, anti-inflammatory, anti-hypertensive, cardioprotective, or organ protective effects), or that quantitatively is less than the established therapeutic dose for that particular pharmacological agent (e.g., as published in a reference consulted by a person of skill, for example, doses for a pharmacological agent published in the Physicians' Desk Reference, 62nd Ed., 2008, Thomson Healthcare or Brunton, et al., Goodman & Gilman's The Pharmacological Basis of Therapeutics, 11th edition, 2006, McGraw-Hill Professional). A "subtherapeutic dose" can be defined in relative terms (i.e., as a percentage amount (less than 100%) of the amount of pharmacologically active agent conventionally administered). For example, a subtherapeutic dose amount can be about 1% to about 75% of the amount of pharmacologically active agent conventionally administered. In some embodiments, a subtherapeutic dose can be about 75%, 50%, 30%, 25%, 20%, 10% or less, than the amount of pharmacologically active agent conventionally administered.

As used herein, in the context of IL8 inhibitor, the term "therapeutically amount effective," means the amount, or dose, of IL8 inhibitor that, when administered to a diabetic individual exhibiting diabetic nephropathy, or an individual having the diabetic condition, is sufficient for therapeutic efficacy, sufficient to decrease the development of one or more of the symptoms of the disease, condition or disorder being treated. (e.g., an amount sufficient to reduce the level of protein in urine in a diabetic individual exhibiting DN).

As used herein in the context of administration of the IL8 inhibitor, the term "prophylactically amount effective," means the amount, or dose, of IL8 inhibitor that, when administered to a diabetic individual has no diabetic nephropathy, or an individual having the diabetic condition, refer to that amount of drug that is sufficient to prevent or reduce the risk of occurrence of onset of symptoms of DN (e.g., an amount sufficient to prevent the rise in the protein level in the urine in a diabetic individual), ie., the biological or medical event that is sought to be prevented. In many instances, the prophylactically effective amount is the same as the therapeutically effective amount.

As used herein, the term "nephropathy" means kidney disease, also known as renal disease, where there is damage to or disease of a kidney.

As used herein, the term "diabetic condition" refers to a condition characterized by impaired glucose production and/or utilization and includes diabetes (e.g., type 1 diabetes, type 2 diabetes, and gestational diabetes), pre-diabetes, metabolic syndrome, hyperglycemia, impaired glucose tolerance, and impaired fasting glucose.

As used herein, the term "diabetes" refers to a disease or condition that is generally characterized by metabolic defects in production and utilization of glucose which result in the failure to maintain appropriate blood sugar levels in the body. A subject is identified as having diabetes if the subject has a fasting blood glucose level greater than 125 mg/dl, a 2 hour post-load glucose reading of greater than 200 mg/dl, or a HbA1c level greater than or equal to 6.5%.

As used herein, the term "pre-diabetes" refers to a disease or condition that is generally characterized by impaired glucose tolerance and which frequently precedes the onset of diabetes in a subject.

A subject is identified as having pre-diabetes if the subject has a fasting blood glucose level greater than 100 mg/dl but less than or equal to 125 mg/dl, a 2 hour post-load glucose reading of greater than 140 mg/dl but less than 200 mg/dl, or a HbA1c level greater than or equal to 6.0% but less than 6.5%.

As used herein, the term "hyperglycemia" refers to elevated blood glucose levels in the body, which results from metabolic defects in production and utilization of glucose. A subject is identified as hyperglycemic if the subject has a fasting blood glucose level that consistently exceeds 126 mg/dl.

As used herein, the term "overweight" refers to an individual who has a body mass index of 25 kg/m2 or more, but less than 30 kg/m2.

As used herein, the term "body mass index" or "BMI" refers to a weight to height ratio measurement that estimates whether an individual's weight is appropriate for their height. As used herein, an individual's body mass index is calculated as follows: BMI=(pounds×700)/(height in inches)2 or BMI=(kilograms)/(height in meters)2

As used herein, the term "baseline body weight" refers to the body weight presented by the individual at the initiation of treatment.

As used herein, the term "obese" or "obesity" refers to an individual who has a body mass index (BMI) of 30 kg/m2 or more due to excess adipose tissue. Obesity also can be defined on the basis of body fat content: greater than 25% body fat content for a male or more than 30% body fat content for a female. A "morbidly obese" individual has a body mass index greater than 35 kg/m2

Embodiments of the present disclosure are based on experimental demonstrations of the therapeutic efficacy of Reparixin and/or ladarixin in preventing the onset and the development and progression of diabetic nephropathy (DN).

In details, the present inventors have found a specific and reproducible pattern of expression of IL8 in the kidney in terms of both localization and time of expression, in both animal models of diabetes and diabetic patients. In fact, as will be evident from the experimental section, IL8 was found to be expressed specifically in endothelial cells and podocytes and at significant levels only during mesangial expansion. On the contrary, a consistent reduction in the levels of expression of IL8 was observed during subsequent progression of glomeruli injury to nodular transformation and glomerulosclerosis. In animal models of diabetes, the present inventors demonstrated that KC/CXCR2 axis blockade with Reparixin prevents urinary increase in albumin excretion as well as mesangial expansion. Furthermore, IL8 was shown to induce a direct injury to podocytes that can be inhibited by administration of a CXCR1/2 inhibitor, as exemplified by reparixin. The experimental section demonstrates that IL8 plays an important role in the onset and development of diabetic nephropathy in the very first steps of the pathology, stimulating mesangial expansion and podocytes damage. After this stage, its expression and pathogenic role progressively declines. The inventors have also identified the level of urinary IL8 that correspond to patients most responsive to anti-IL8 therapy, preferably microalbuminuric patients.

Accordingly, a first object of the present invention is a method for the treatment of diabetic nephropathy or for the prevention, reduction of the risk or delay of the onset or progression of diabetic nephropathy, comprising administering to a subject in need.

A second object of this disclosure is to provide use of an IL8 inhibitor, preferably a CXCR1 and/or CXCR2 inhibitor, more preferably a CXCR1 and CXCR2 inhibitor and, even more preferably, a compound selected from R(−)-2-[(4-isobutylphenyl)propionyl]-methanesulfonamide (hereinbelow referred to as reparixin) or a salt thereof, preferably its lysine salt, R(−)-2-[(4'-trifluoromethane sulfonyloxy)phenyl]-N-methanesulfonyl propionamide (hereinbelow referred to as ladarixin) or a salt thereof, preferably its sodium salt, and (2S)-2-(4-{[4-(trifluoromethyl)-1,3-thiazol-2-yl]amino} phenyl) propanoic acid (hereinbelow referred to as DF2755Y), or a salt thereof, preferably its sodium salt (hereinbelow referred to as DF2755A), to treat diabetic nephropathy or to prevent, reduce the risk or delay the onset or progression of diabetic nephropathy in a subject.

A third object of this disclosure is to provide use of an IL8 inhibitor, preferably a CXCR1 and/or CXCR2 inhibitor, more preferably a CXCR1 and CXCR2 inhibitor and, even more preferably, a compound selected from R(−)-2-[(4-isobutylphenyl)propionyl]-methanesulfonamide (hereinbelow referred to as reparixin) or a salt thereof, preferably its lysine salt, R(−)-2-[(4'-trifluoromethane sulfonyloxy)phenyl]-N-methanesulfonyl propionamide (hereinbelow referred to as ladarixin) or a salt thereof, preferably its sodium salt, and (2S)-2-(4-{[4-(trifluoromethyl)-1,3-thiazol-2-yl]amino} phenyl) propanoic acid (hereinbelow referred to as DF2755Y) or a salt thereof, preferably its sodium salt (hereinbelow referred to as DF2755A), for the manufacture of a medicament to treat diabetic nephropathy or to prevent, reduce the risk or delay the onset or progression of diabetic nephropathy in a subject.

A fourth object of this disclosure is to provide an IL8 inhibitor, preferably a CXCR1 and/or CXCR2 inhibitor, more preferably a CXCR1 and CXCR2 inhibitor and, even more preferably, a compound selected from R(−)-2-[(4-isobutylphenyl)propionyl]-methanesulfonamide (hereinbelow referred to as reparixin) or a salt thereof, preferably its lysine salt, R(−)-2-[(4'-trifluoromethane sulfonyloxy)phenyl]-N-methanesulfonyl propionamide (hereinbelow referred to as ladarixin) or a salt thereof, preferably its sodium salt, and (2S)-2-(4-{[4-(trifluoromethyl)-1,3-thiazol-2-yl] amino} phenyl) propanoic acid (hereinbelow referred to as DF2755Y) or a salt thereof, preferably its sodium salt (hereinbelow referred to as DF2755A), for the use in the treatment of diabetic nephropathy or in the prevention, reduction of the risk or delay of the onset or progression of diabetic nephropathy in a subject.

In one embodiment of each of the above objects of the invention, in said method or use the subject has been diagnosed with diabetes.

In one embodiment of each of the above objects of the invention, in said method or use the subject has been diagnosed with Type 1 diabetes.

In one embodiment of each of the above objects of the invention, in said method or use the subject has been diagnosed with Type 2 diabetes.

Therefore, for example, in real life practice, it is contemplated that when an individual is diagnosed with diabetes, either Type 1 or Type 2, an IL8 inhibitor, preferably a CXCR1 and/or CXCR2 inhibitor, more preferably a CXCR1 and CXCR2 inhibitor and, even more preferably, a compound selected from R(−)-2-[(4-isobutylphenyl)propionyl]-methanesulfonamide (hereinbelow referred to as reparixin) or a salt thereof, preferably its lysine salt, R(−)-2-[(4'-trifluoromethane sulfonyloxy)phenyl]-N-methanesulfonyl propionamide (hereinbelow referred to as ladarixin) or a salt thereof, preferably its sodium salt, and (2S)-2-(4-{[4-(trifluoromethyl)-1,3-thiazol-2-yl] amino} phenyl) propanoic acid (hereinbelow referred to as DF2755Y), or a salt thereof, preferably its its sodium salt (hereinbelow referred to as DF2755A), is immediately administered prophylactically to prevent the onset of diabetic nephropathy which can develop as the diabetic condition continues and managed/treated.

In one embodiments of each of the above objects of the invention, also in combination with any of the previous embodiments, the subject has normal proteinuria. In one embodiments of each of the above objects of the invention, also in combination with any of the previous embodiments, the subject has increased proteinuria. In one embodiment, increased proteinuria is at least 300 mg albumin excreted in a 24 hr. period. In one embodiment, the protein measured is albumin.

In one embodiment of each of the above objects of the invention, also in combination with any of the previous embodiments, the subject has microalbuminuria.

In one embodiment, the term "microalbuminuria" refers to any disease, disorder, ailment or state of health where urinary albumin is excreted in the urine at a rate of about 20-200 μg/minute or about 30-300 mg/24 hours, (see, for example, Abbott, K. C., et al, Arch. Internal Med. 754:146-153 (1994), the teachings of which are incorporated herein by reference in their entirety). In another embodiment, the term "microalbuminuria" refers to any disease, disorder, ailment or state of health where albumin is excreted in the urine at between 30 and 300 mg per day.

Methods to detect and diagnosis microalbuminuria are well known to one of skill in the art and include radioimmunoassays, immunoassays with latex bodies, fluoroimmunoassays, enzyme immunoassays, agglutination inhibition, immunoturbidimetry, immunonephelometry and radial immunodiffusion assays. For examples, U.S. Pat. Nos. 5,326,707; 5,492,834; 5,385,847; 5,750,405, US20030027216; US20030232396, the contents of each are incorporated herein by reference in their entirety.

Therefore, for example, when the diabetic individual has been diagnosed with early diabetic nephropathy, evidenced by the onset of microalbuminuria, an IL8 inhibitor, preferably a CXCR1 and/or CXCR2 inhibitor, more preferably a CXCR1 and CXCR2 inhibitor and, even more preferably, a compound selected from R(−)-2-[(4-isobutylphenyl)propionyl]-methanesulfonamide (hereinbelow referred to as reparixin) or a salt thereof, preferably its lysine salt, R(−)-2-[(4'-trifluoromethane sulfonyloxy)phenyl]-N-methanesulfonyl propionamide (hereinbelow referred to as ladarixin) or a salt thereof, preferably its lysine salt, and (2S)-2-(4-{[4-(trifluoromethyl)-1,3-thiazol-2-yl] amino} phenyl) propanoic acid (hereinbelow referred to as DF2755Y) or a salt thereof, preferably its sodium salt (hereinbelow referred to as DF2755A), is immediately administered prophylactically to treat, prevent and/or delay the progression of diabetic nephropathy in that diabetic individual.

In another embodiment of each of the above objects of the invention, also in combination with any of the previous embodiments, in said method or use the subject has a level of IL8 in a biological sample higher than a IL8 reference standard, wherein said reference standard is the mean IL8 level in the corresponding biological sample of a statistically significant number of non-diabetic individuals not having any nephropathy and inflammatory disease.

Various methods of determining IL8 levels in a biological sample can be used. For example, measuring the mRNA level of IL8 via quantitative RT-PCR or by immune-based analysis such as ELISA and Western blotting. For example, monoclonal antibodies reagents in an enzyme-linked immunoabsorbent assay (ELISA) for IL8 are described in the U.S. Pat. Nos. 6,133,426 and 6,468,532. The contents of each of these are incorporated herein by reference in their entirety.

In another embodiment of each of the above objects of the invention, also in combination with any of the previous embodiments, in said method or use the subject has a urinary level of IL8 higher than a IL8 reference standard, wherein said reference standard is the mean IL8 urinary level of a statistically significant number of non-diabetic individuals not having any nephropathy and inflammatory disease. In one embodiment of any method or use described, an elevated IL8 level means at least an increase of at least 10% as compared to a reference IL8 level. In other embodiment of any method described, an elevated IL8 level means at least an increase of at least about 10%, at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference IL8 level.

In another embodiment of each of the above objects of the invention, also in combination with any of the previous embodiments, in said method or use the subject has a level of IL8 expression in a kidney biopsy higher than a IL8 reference standard, wherein said reference standard is the mean level of expression of IL8 in kidney biopsies from non-diabetic individuals not having any nephropathy and inflammatory disease. In another embodiment of each of the above objects of the invention, also in combination with any of the previous embodiments, in said method or use, the reference level of urine IL8 is the mean level of urine IL8 from non-diabetic individuals not having any nephropathy and inflammatory disease. For example, the mean level is obtained from a population of 10-25 non-diabetic individuals not having any nephropathy and inflammatory disease. In another embodiment of each of the above objects of the invention, also in combination with any of the previous embodiments, in said method or use, the reference level of protein in the urine is the mean level of urine protein from non-diabetic individuals not having any nephropathy and inflammatory disease. For example, the mean level is obtained from a population of 10-25 non-diabetic individuals not having any nephropathy and inflammatory disease.

For example, in real life practice, it is contemplated that when an individual is diagnosed with diabetes but has not yet developed diabetic nephropathy, e.g., as in having normal proteinuria, the same individual is further tested for the IL8 level. When this diabetic individual has been demonstrated to have increased or elevated IL8 level, then an IL8 inhibitor, preferably a CXCR1 and/or CXCR2 inhibitor, more preferably a CXCR1 and CXCR2 inhibitor and, even more preferably, a compound selected from R(−)-2-[(4-isobutylphenyl)propionyl]-methanesulfonamide (hereinbelow referred to as reparixin) or a salt thereof, preferably its lysine salt, R(−)-2-[(4'-trifluoromethane sulfonyloxy)phenyl]-N-methanesulfonyl propionamide (hereinbelow referred to as ladarixin) or a salt thereof, preferably its sodium salt, and (2S)-2-(4-{[4-(trifluoromethyl)-1,3-thiazol-2-yl] amino} phenyl) propanoic acid (hereinbelow referred to as DF2755Y) or a salt thereof, preferably its sodium salt (hereinbelow referred to as DF2755A), is immediately administered prophylactically to prevent the onset of diabetic nephropathy. Moreover, when a diabetic individual has developed early diabetic nephropathy, the same individual is also tested for the IL8 levels. When such individual has been demonstrated to have also increased or elevated IL8 level, then an IL8 inhibitor, preferably a CXCR1 and/or CXCR2 inhibitor, more preferably Reparixin and/or Ladarixin, is immediately administered prophylactically to treat, prevent and/or delay the progression of diabetic nephropathy in that individual.

In another embodiment of each of the above objects of the invention, also in combination with any of the previous embodiments, in said method or use the subject has a urinary level of IL8 at least higher than 2.41 pg/ml.

In another embodiment of each of the above objects of the invention, also in combination with any of the previous embodiments, in said method or use the subject has a urinary level of IL8 higher than 2.41 pg/ml and has microalbuminuria.

As demonstrated in the experimental section below, this urinary level of IL8 identifies patients that are in the phase of the pathology wherein IL8 plays a pivotal role and therefore are responsive to a therapeutic treatment with IL8 inhibitors.

According to a further embodiment of each of the above objects of the invention, also in combination with any of the previous embodiments, in said method or use the subject has a value of GFR (glomerular filtration rate) above 60 ml/min/1.73m2, preferably above 90 ml/min/1.73m2.

As demonstrated in the experimental section, IL8 has a pathogenic role in the very early phase of the pathology, when damage to the structure of the glomeruli is not yet overt and GFR decline has not yet started. The above values of GRF thus identify patients that are in the phase of the pathology wherein IL8 has a pivotal role and therefore are responsive to a therapeutic treatment with IL8 inhibitors.

As will be discussed in the experimental section, the present inventors have also identified a number of single nucleotide polymorphisms in the CXCR1 receptor gene that are associated with the development of diabetic kidney disease.

Accordingly, in a further embodiment of each of the above objects of the invention, also in combination with any of the previous embodiments, in said method or use the subject has at least one of the following single nucleotide polymorphisms at the CXCR1 locus: s13006838, rs4674308; rs4674309; rs3755042; rs7601872; and rs664514.

In a further embodiment of each of the above objects of the invention, also in combination with any of the previous embodiments, in said method or use the subject has high HbA1C.

In a further embodiment of each of the above objects of the invention, also in combination with any of the previous embodiments, in said method or use the subject is not overweight or obese.

In a further embodiment of each of the above objects of the invention, also in combination with any of the previous embodiments, in said method or use the subject is overweight or obese.

In a further embodiment of each of the above objects of the invention, also in combination with any of the previous embodiments, in said method or use the subject is a human.

In one embodiment of the first object of the invention, also in combination with any of the previous embodiments, provided herein is a method for treatment of diabetic nephropathy or for prevention, reduction of the risk or delay of the onset or progression of diabetic nephropathy, the method comprising: (a) measuring the level of expression of IL8 in a kidney biopsy from the subject; (b) comparing the measured IL8 level of expression with a reference standard; and (c) administering an IL8 inhibitor, preferably a CXCR1 and/or CXCR2 inhibitor, more preferably a CXCR1 and CXCR2 inhibitor and, even more preferably, a compound selected from R(−)-2-[(4-isobutylphenyl)propionyl]-methanesulfonamide (hereinbelow referred to as reparixin) or a salt thereof, preferably its lysine salt, R(−)-2-[(4'-trifluoromethane sulfonyloxy)phenyl]-N-methanesulfonyl propionamide (hereinbelow referred to as ladarixin) or a salt thereof, preferably its sodium salt, and (2S)-2-(4-{[4-(trifluoromethyl)-1,3-thiazol-2-yl] amino} phenyl) propanoic acid (hereinbelow referred to as DF2755Y), or a salt thereof, preferably its, its sodium salt (hereinbelow referred to as DF2755A) to the subject when the measured IL8 level is above an IL8 reference standard, wherein said reference standard is the mean level of expression of IL8 in kidney biopsies from non-diabetic individuals not having any nephropathy or inflammatory disease.

In one embodiment of the first object of the invention, also in combination with any of the previous embodiments, provided herein is a method of treatment of diabetic nephropathy or of prevention, reduction of the risk or delay of the onset or progression of diabetic nephropathy, the method comprising: (a) measuring the urinary level of IL8 in the subject; (b) comparing the measured IL8 level with a reference standard; and (c) administering an IL8 inhibitor, preferably a CXCR1 and/or CXCR2 inhibitor, more preferably a CXCR1 and CXCR2 inhibitor and, even more preferably, a compound selected from R(−)-2-[(4-isobutylphenyl)propionyl]-methanesulfonamide (hereinbelow referred to as reparixin) or a salt thereof, preferably its lysine salt, R(−)-2-[(4'-trifluoromethane sulfonyloxy)phenyl]-N-methanesulfonyl propionamide (hereinbelow referred to as ladarixin) or a salt thereof, preferably its sodium salt, and (2S)-2-(4-{[4-(trifluoromethyl)-1,3-thiazol-2-yl] amino} phenyl) propanoic acid (hereinbelow referred to as DF2755Y) or a salt thereof, preferably its its sodium salt (hereinbelow referred to as DF2755A), to the subject when the measured IL8 level is above an IL8 reference standard, wherein said reference standard is the mean urinary IL8 level of a statistically significant number of non-diabetic individuals not having any nephropathy or inflammatory disease.

For example, in real life practice, it is contemplated that when a subject has been diagnosed with diabetes but has not developed diabetic nephropathy, the same individual is further tested for the IL8 level and this measured IL8 level is compared to a IL8 reference standard. When this diabetic subject has been demonstrated to have increased or elevated IL8 levels compared to the IL8 reference standard, an IL8 inhibitor, preferably a CXCR1 and/or CXCR2 inhibitor, more preferably a CXCR1 and CXCR2 inhibitor and, even more preferably, a compound selected from R(−)-2-[(4-isobutylphenyl)propionyl]-methanesulfonamide (hereinbelow referred to as reparixin) or a salt thereof, preferably its lysine salt, R(−)-2-[(4'-trifluoromethane sulfonyloxy)phenyl]-N-methanesulfonyl propionamide (hereinbelow referred to as ladarixin) or a salt thereof, preferably its sodium salt, and (2S)-2-(4-{[4-(trifluoromethyl)-1,3-thiazol-2-yl] amino} phenyl) propanoic acid (hereinbelow referred to as DF2755Y), or a salt thereof, preferably its, its sodium salt (hereinbelow referred to as DF2755A) is/are immediately administered prophylactically to prevent or delay the onset of diabetic nephropathy. Moreover, when a diabetic subject has developed early diabetic nephropathy, the same subject is further tested for the IL8 level and this measured IL8 level is compared to an IL8 reference standard. When this diabetic individual has been demonstrated to have increased or elevated IL8 level over the reference IL8 level, then an IL8 inhibitor, preferably a CXCR1 and/or CXCR2 inhibitor, more preferably a CXCR1 and CXCR2 inhibitor and, even more preferably, a compound selected from R(−)-2-[(4-isobutylphenyl)propionyl]-methanesulfonamide (hereinbelow referred to as reparixin) or a salt thereof, preferably its lysine salt, R(−)-2-[(4'-trifluoromethane sulfonyloxy)phenyl]-N-methanesulfonyl propionamide (hereinbelow referred to as ladarixin) or a salt thereof, preferably its sodium salt, and (2S)-2-(4-{[4-(trifluoromethyl)-1,3-thiazol-2-yl] amino} phenyl) propanoic acid (hereinbelow referred to as DF2755Y), or a salt thereof, preferably its sodium salt (hereinbelow referred to as DF2755A) is/are immediately administered prophylactically to treat, prevent and/or delay the progression of diabetic in that diabetic subject.

In another embodiment of the first object of the invention, also in combination with any of the previous embodiments, provided herein is a method of treatment of diabetic nephropathy or prevention, reduction of the risk or delay of the onset or progression of diabetic nephropathy in a subject, the method comprising: (a) measuring the level of urinary IL8 in a subject; and (b) administering an IL8 inhibitor, preferably a CXCR1 and/or CXCR2 inhibitor, more preferably a CXCR1 and CXCR2 inhibitor and, even more preferably, a compound selected from R(−)-2-[(4-isobutylphenyl)propionyl]-methanesulfonamide (hereinbelow referred to as reparixin) or a salt thereof, preferably its lysine salt, R(−)-2-[(4'-trifluoromethane sulfonyloxy)phenyl]-N-methanesulfonyl propionamide (hereinbelow referred to as ladarixin) or a salt thereof, preferably its sodium salt, and (2S)-2-(4-{[4-(trifluoromethyl)-1,3-thiazol-2-yl] amino} phenyl) propanoic acid (hereinbelow referred to as DF2755Y), or a salt thereof, preferably its, its sodium salt (hereinbelow referred to as DF2755A), to the subject when the measured urinary IL8 level is above 2.41 pg/ml.

In another embodiment of the first object of the invention, also in combination with any of the previous embodiments, provided herein is a method of treatment of diabetic nephropathy or prevention, reduction of the risk or delay of the onset or progression of diabetic nephropathy in a subject, the method comprising: (a) measuring the level of protein in a urine sample obtained from the subject; (b) comparing the measured urine protein level with a urine protein reference standard; and (c) an IL8 inhibitor, preferably a CXCR1 and/or CXCR2 inhibitor, more preferably a CXCR1 and CXCR2 inhibitor and, even more preferably, a compound selected from R(−)-2-[(4-isobutylphenyl)propionyl]-methanesulfonamide (hereinbelow referred to as reparixin) or a salt thereof, preferably its lysine salt, R(−)-2-[(4'-trifluoromethane sulfonyloxy)phenyl]-N-methanesulfonyl propionamide (hereinbelow referred to as ladarixin) or a salt thereof, preferably its lysine salt, and (2S)-2-(4-{[4-(trifluoromethyl)-1,3-thiazol-2-yl]amino} phenyl) propanoic acid (hereinbelow referred to as DF2755Y), or a salt thereof, preferably its, its sodium salt (hereinbelow referred to as DF2755A), to the subject when the measured urine protein level is above the urine protein reference wherein said reference is the mean urinary protein level of a statistically significant number of non-diabetic individuals not having any nephropathy. In another embodiment of each of the above objects of the invention, also in combination with any of the previous embodiments, in said method or use, the reference level of protein in the urine is the mean level of urine protein from non-diabetic individuals not having any nephropathy and inflammatory disease. For example, the mean level is obtained from a population of 10-25 non-diabetic individuals not having any nephropathy and inflammatory disease.

In practice, for example, it is contemplated that when a subject has been diagnosed with diabetes but has not developed diabetic nephropathy, the same individual is further tested for the level of urine protein and this measured level of urine protein is compared to a reference level of urine protein. When this diabetic subject has been demonstrated to have increased or elevated the level of urine protein compared to the reference, then an IL8 inhibitor, preferably a CXCR1 and/or CXCR2 inhibitor, more preferably a CXCR1 and CXCR2 inhibitor and, even more preferably, a compound selected from R(−)-2-[(4-isobutylphenyl)propionyl]-methanesulfonamide (hereinbelow referred to as reparixin), or a salt thereof, preferably its lysine salt, R(−)-2-[(4'-trifluoromethane sulfonyloxy)phenyl]-N-methanesulfonyl propionamide (hereinbelow referred to as ladarixin) or a salt thereof, preferably its sodium salt, and (2S)-2-(4-{[4-(trifluoromethyl)-1,3-thiazol-2-yl] amino} phenyl) propanoic acid (hereinbelow referred to as DF2755Y), or a salt thereof, preferably its lysine salt, its sodium salt (hereinbelow referred to as DF2755A), is immediately administered prophylactically to prevent or delay the onset of diabetic nephropathy. Moreover, when a diabetic subject has developed early DN, the same subject is further tested for the level of urine protein and this measured level of urine protein is compared to a reference level of urine protein. When this diabetic individual has been demonstrated to have increased or elevated level of urine protein over the reference level urine protein, then an IL8 inhibitor, preferably a CXCR1 and/or CXCR2 inhibitor, more preferably a CXCR1 and CXCR2 inhibitor and, even more preferably, a compound selected from R(−)-2-[(4-isobutylphenyl)propionyl]-methanesulfonamide (hereinbelow referred to as reparixin) or a salt thereof, preferably its lysine salt, R(−)-2-[(4'-trifluoromethane sulfonyloxy)phenyl]-N-methanesulfonyl propionamide (hereinbelow referred to as ladarixin) or a salt thereof, preferably its sodium salt, and (2S)-2-(4-{[4-(trifluoromethyl)-1,3-thiazol-2-yl] amino} phenyl) propanoic acid (hereinbelow referred to as DF2755Y) or a salt thereof, preferably its sodium salt (hereinbelow referred to as DF2755A), is immediately administered to treat, prevent and/or delay the progression of diabetic nephropathy in that diabetic subject.

In another embodiment of the first object of the invention, also in combination with any of the previous embodiments, provided herein is a method of treatment of diabetic nephropathy or prevention, reduction of the risk or delay of the onset or progression of diabetic nephropathy in a subject, the method comprising: (a) measuring the rate of excretion of albumin in the urine from the subject; and (b) administering an IL8 inhibitor, preferably a CXCR1 and/or CXCR2 inhibitor, more preferably a CXCR1 and CXCR2 inhibitor and, even more preferably, a compound selected from R(−)-2-[(4-isobutylphenyl)propionyl]-methanesulfonamide (hereinbelow referred to as reparixin) or a salt thereof, preferably its lysine salt, R(−)-2-[(4'-trifluoromethane sulfonyloxy)phenyl]-N-methanesulfonyl propionamide (hereinbelow referred to as ladarixin) or a salt thereof, preferably its sodium salt, and (2S)-2-(4-{[4-(trifluoromethyl)-1,3-thiazol-2-yl] amino} phenyl) propanoic acid (hereinbelow referred to as DF2755Y), or a salt thereof, preferably its its sodium salt (hereinbelow referred to as DF2755A), to the subject when the measured rate of excretion of albumin is between 30 and 300 mg per day.

In another embodiment of the first object of the invention, also in combination with any of the previous embodiments, it is provided herein is a method of method treatment of diabetic nephropathy or of prevention, reduction of the risk or delay of the onset or progression of diabetic nephropathy, the method comprising: (a) determining whether the subject has at least one of the following single nucleotide polymorphisms (SNPs) at the CXCR1 locus: s13006838, rs4674308; rs4674309; rs3755042; rs7601872; and rs664514; and (b) administering an IL8 inhibitor, preferably a CXCR1 and/or CXCR2 inhibitor, more preferably a CXCR1 and CXCR2 inhibitor and, even more preferably, a compound selected from R(−)-2-[(4-isobutylphenyl)propionyl]-methanesulfonamide (hereinbelow referred to as reparixin) or a salt thereof, preferably its lysine salt, R(−)-2-[(4'-trifluoromethane sulfonyloxy)phenyl]-N-methanesulfonyl propionamide (hereinbelow referred to as ladarixin) or a salt thereof, preferably its sodium salt, and (2S)-2-(4-{[4-(trifluoromethyl)-1,3-thiazol-2-yl]amino} phenyl) propanoic acid (hereinbelow referred to as DF2755Y), or a salt thereof, preferably its its sodium salt (hereinbelow referred to as DF2755A), to the subject when the subject has at least one of the SNPs.

In real life practice, for example, it is contemplated that when a subject has been diagnosed with diabetes but has not developed diabetic nephropathy, the genome of the same individual is further tested for the described SNPs. When this diabetic subject has been demonstrated to have at least one of the described SNPs, then an IL8 inhibitor, preferably a CXCR1 and/or CXCR2 inhibitor, more preferably a CXCR1 and CXCR2 inhibitor and, even more preferably, a compound selected from R(−)-2-[(4-isobutylphenyl)propionyl]-methanesulfonamide (hereinbelow referred to as reparixin) or a salt thereof, preferably its lysine salt, R(−)-2-[(4'-trifluoromethane sulfonyloxy)phenyl]-N-methanesulfonyl propionamide (hereinbelow referred to as ladarixin) or a salt thereof, preferably its sodium salt, and (2S)-2-(4-{[4-(trifluoromethyl)-1,3-thiazol-2-yl] amino} phenyl) propanoic acid (hereinbelow referred to as DF2755Y), or a salt thereof, preferably its salt, its sodium salt (hereinbelow referred to as DF2755A), is immediately administered prophylactically to prevent or delay the onset of DN. Moreover, when a diabetic subject has developed early diabetic nephropathy, the genome of the same individual is further tested for the described SNPs. When this diabetic subject has been demonstrated to have at least one of the described SNPs, then an IL8 inhibitor, preferably a CXCR1 and/or CXCR2 inhibitor, more preferably a CXCR1 and CXCR2 inhibitor and, even more preferably, a compound selected from R(−)-2-[(4-isobutylphenyl)propionyl]-methanesulfonamide (hereinbelow referred to as reparixin), R(−)-2-[(4'-trifluoromethane sulfonyloxy)phenyl]-N-methanesulfonyl propionamide (hereinbelow referred to as ladarixin) and (2S)-2-(4-{[4-(trifluoromethyl)-1,3-thiazol-2-yl] amino} phenyl) propanoic acid (hereinbelow referred to as DF2755Y), or its sodium salt (hereinbelow referred to as DF2755A), is immediately administered to prevent and/or treat and or delay the onset or progression of diabetic nephropathy in that subject.

In one embodiment of the first object of the invention, also in combination with any of the previous embodiments, provided herein is a method of treatment of diabetic nephropathy or prevention, reduction of the risk or delay of the onset or progression of diabetic nephropathy in a subject, the method comprising: (a) determining whether the subject has at least one of the following single nucleotide polymorphisms (SNPs) at the CXCR1 locus: s13006838, rs4674308; rs4674309; rs3755042; rs7601872; and rs664514; (b) measuring the urinary level of IL8 in the subject; (c) comparing the measured IL8 level with a reference; and (d) administering an IL8 inhibitor, preferably a CXCR1 and/or CXCR2 inhibitor, more preferably a CXCR1 and CXCR2 inhibitor and, even more preferably, a compound selected from R(−)-2-[(4-isobutylphenyl)propionyl]-methanesulfonamide (hereinbelow referred to as reparixin), or a salt thereof, preferably its lysine salt, R(−)-2-[(4'-trifluoromethane sulfonyloxy)phenyl]-N-methanesulfonyl propionamide (hereinbelow referred to as ladarixin) or a salt thereof, preferably its sodium salt, and (2S)-2-(4-{[4-(trifluoromethyl)-1,3-thiazol-2-yl] amino} phenyl) propanoic acid (hereinbelow referred to as DF2755Y), or a salt thereof, preferably its, its sodium salt (hereinbelow referred to as DF2755A) to the subject when the subject has at least one of the SNPs, and has increased IL8 with respect to the reference, wherein said reference is the mean urinary level of IL8 of a statistically significant number of non-diabetic individuals not having any nephropathy or inflammatory disease.

In an alternative embodiment of the first object of the invention, also in combination with any of the previous embodiments, provided herein is a method of treatment of diabetic nephropathy or prevention, reduction of the risk or delay of the onset or progression of diabetic nephropathy in a subject, the method comprising: (a) determining whether the subject has at least one of the following single nucleotide polymorphisms (SNPs) at the CXCR1 locus: s13006838, rs4674308; rs4674309; rs3755042; rs7601872; and rs664514; (b) measuring the level of expression of IL8 in a kidney biopsy from the subject; (c) comparing the measured expression of IL8 with a reference; and (d) administering an IL8 inhibitor, preferably a CXCR1 and/or CXCR2 inhibitor, more preferably a CXCR1 and CXCR2 inhibitor and, even more preferably, a compound selected from R(−)-2-[(4-isobutylphenyl)propionyl]-methanesulfonamide (hereinbelow referred to as reparixin) or a salt thereof, preferably its lysine salt, R(−)-2[(4'-trifluoromethane sulfonyloxy)phenyl]-N-methanesulfonyl propionamide (hereinbelow referred to as ladarixin) or a salt thereof, preferably its sodium salt, and (2S)-2-(4-{[4-(trifluoromethyl)-1,3-thiazol-2-yl] amino} phenyl) propanoic acid (hereinbelow referred to as DF2755Y), or a salt thereof, preferably, its sodium salt (hereinbelow referred to as DF2755A), to the subject when the subject has at least one of the SNPs, and has increased IL8 expression with respect to the reference, wherein said reference is the mean level of expression of IL8 in the kidney of non-diabetic individuals not having any nephropathy or inflammatory disease.

In practice, for example, it is contemplated that when a subject has been diagnosed with diabetes or having the diabetic condition but has not developed DN, the genome of the same individual is further tested for the described SNPs, and the same individual is further tested for the IL8 level and this measured IL8 level is compared to a reference IL8. When this diabetic subject has been demonstrated to have at least one of the described SNPs, and demonstrated to have increased or elevated IL8 level compared to the reference IL8, then an IL8 inhibitor, preferably a CXCR1 and/or CXCR2 inhibitor, more preferably a CXCR1 and CXCR2 inhibitor and, even more preferably, a compound selected from R(−)-2-[(4-isobutylphenyl)propionyl]-methanesulfonamide (hereinbelow referred to as reparixin) or a salt thereof, preferably its lysine salt, R(−)-2-[(4'-trifluoromethane sulfonyloxy)phenyl]-N-methanesulfonyl propionamide (hereinbelow referred to as ladarixin) or a salt thereof, preferably its sodium salt, and (2S)-2-(4-{[4-(trifluoromethyl)-1,3-thiazol-2-yl] amino} phenyl) propanoic acid (hereinbelow referred to as DF2755Y), or a salt thereof, preferably its sodium salt (hereinbelow referred to as DF2755A), is immediately administered prophylactically to prevent or delay the onset of diabetic nephropathy. Moreover, when a diabetic subject has developed early diabetic nephropathy, the genome of the same individual is further tested for the described SNPs, and the same individual is further tested for the IL8 level and this measured IL8 level is compared to a reference IL8. When this diabetic subject has been demonstrated to have at least one of the described SNPs, and demonstrated to have increased or elevated IL8 level over the reference IL8 level, then an IL8 inhibitor, preferably a CXCR1 and/or CXCR2 inhibitor, more preferably a CXCR1 and CXCR2 inhibitor and, even more preferably, a compound selected from R(−)-2-[(4-isobutylphenyl)propionyl]-methanesulfonamide (hereinbelow referred to as reparixin) or a salt thereof, preferably its lysine salt, R(−)-2-[(4'-trifluoromethane sulfonyloxy)phenyl]-N-methanesulfonyl propionamide (hereinbelow referred to as ladarixin) or a salt thereof, preferably its sodium salt, and (2S)-2-(4-{[4-(trifluoromethyl)-1,3-thiazol-2-yl] amino} phenyl) propanoic acid (hereinbelow referred to as DF2755Y) or a salt thereof, preferably its its sodium salt (hereinbelow referred to as DF2755A), is immediately administered prophylactically to treat, prevent and/or delay the progression of diabetic nephropathy in that diabetic subject.

In one embodiment of the first object of the invention, also in combination with any of the previous embodiments, provided herein is a method of treatment of diabetic nephropathy or prevention, reduction of the risk or delay of the onset or progression of diabetic nephropathy in a subject, the method comprising: (a) determining whether the subject has at least one of the following single nucleotide polymorphisms (SNPs) at the CXCR1 locus: s13006838, rs4674308; rs4674309; rs3755042; rs7601872; and rs664514; (b) measuring the urine protein level in the subject; (c) comparing the measured protein level with a protein reference; and (d) administering an IL8 inhibitor, preferably a CXCR1 and/or CXCR2 inhibitor, more preferably a CXCR1 and CXCR2 inhibitor and, even more preferably, a compound selected from R(−)-2-[(4-isobutylphenyl)propionyl]-methanesulfonamide (hereinbelow referred to as reparixin) or a salt thereof, preferably its lysine salt, R(−)-2-[(4'-trifluoromethane sulfonyloxy)phenyl]-N-methanesulfonyl propionamide (hereinbelow referred to as ladarixin) or a salt thereof, preferably its sodium salt, and (2S)-2-(4-{[4-(trifluoromethyl)-1,3-thiazol-2-yl]amino} phenyl) propanoic acid (hereinbelow referred to as DF2755Y), or a salt thereof, preferably its sodium salt (hereinbelow referred to as DF2755A) to the subject when the subject has at least one of the SNPs, and has increased protein in the urine. In one embodiment, the method further comprises obtaining a sample of urine from the subject for protein level analysis. In practice, it is contemplated that when a subject has been diagnosed with diabetes but has not developed DN, the genome of the same individual is further tested for the described SNPs, and the same individual is further tested for the level of urine protein and this measured level of urine protein is compared to a reference level of urine protein. When this diabetic subject has been demonstrated to have at least one of the described SNPs, and demonstrated to have increased or elevated level of urine protein over the reference level urine protein, then an IL8 inhibitor, preferably a CXCR1 and/or CXCR2 inhibitor, more preferably a CXCR1 and CXCR2 inhibitor and, even more preferably, a compound selected from R(−)-2-[(4-isobutylphenyl)propionyl]-methanesulfonamide (hereinbelow referred to as reparixin) or a salt thereof, preferably its lysine salt, R(−)-2-[(4'-trifluoromethane sulfonyloxy)phenyl]-N-methanesulfonyl propionamide (hereinbelow referred to as ladarixin) or a salt thereof, preferably its sodium salt, and (2S)-2-(4-{[4-(trifluoromethyl)-1,3-thiazol-2-yl] amino} phenyl) propanoic acid (hereinbelow referred to as DF2755Y), or a salt thereof, preferably its sodium salt (hereinbelow referred to as DF2755A), is immediately administered prophylactically to prevent or delay the onset of DN. Moreover, when a diabetic subject has developed early diabetic nephropathy, the genome of the same individual is further tested for the described SNPs, and the same individual is further tested for the level of urine protein and this measured level of urine protein is compared to a reference level of urine protein. When this diabetic subject has been demonstrated to have at least one of the described SNPs, and demonstrated to have increased or elevated level of urine protein over the reference level urine protein, then an IL8 inhibitor, preferably a CXCR1 and/or CXCR2 inhibitor, more preferably a CXCR1 and CXCR2 inhibitor and, even more preferably, a compound selected from R(−)-2-[(4-isobutylphenyl)propionyl]-methanesulfonamide (hereinbelow referred to as reparixin) or a salt thereof, preferably its lysine salt, R(−)-2-[(4'-trifluoromethane sulfonyloxy)phenyl]-N-methanesulfonyl propionamide (hereinbelow referred to as ladarixin) or a salt thereof, preferably its sodium salt, and (2S)-2-(4-{[4-(trifluoromethyl)-1,3-thiazol-2-yl]amino} phenyl) propanoic acid (hereinbelow referred to as DF2755Y), or a salt thereof, preferably its sodium salt (hereinbelow referred to as DF2755A), is immediately administered prophylactically to treat, prevent and/or delay the progression of diabetic nephropathy in that diabetic subject.

In one embodiment of the first object of the invention, also in combination with any of the previous embodiments, provided herein is a method of treatment of diabetic nephropathy or prevention, reduction of the risk or delay of the onset or progression of diabetic nephropathy in a subject, the method comprising: (a) measuring the level of IL8 in a sample obtained from the subject; (b) comparing the measured IL8 level with a reference; (c) measuring the protein level in a sample obtained from the subject; (d) comparing the measured protein level with a protein reference and (e) administering Reparixin and/or Ladarixin to the subject when the subject has increased IL8 and protein in the urine. In one embodiment, the sample for protein level analysis is a urine sample. In one embodiment, the method further comprises obtaining a sample of urine from the subject for protein level analysis. In one embodiment, the sample for IL8 level analysis is a urine, a serum, blood or plasma sample. In one embodiment, the method further comprises obtaining a sample of from the subject for IL8 analysis. In practice, when a subject has been diagnosed with diabetes but has not developed DN, the same individual is further tested for the IL8 level and this measured IL8 level is compared to a reference IL8, and further tested for the level of urine protein and this measured level of urine protein is compared to a reference level of urine protein. When this diabetic subject has been demonstrated to have increased or elevated IL8 level compared to the reference IL8, and also demonstrated to have increased or elevated level of urine protein over the reference level urine protein, then an IL8 inhibitor, preferably a CXCR1 and/or CXCR2 inhibitor, more preferably a CXCR1 and CXCR2 inhibitor and, even more preferably, a compound selected from R(−)-2-[(4-isobutylphenyl)propionyl]-methanesulfonamide (hereinbelow referred to as reparixin) or a salt thereof, preferably its lysine salt, R(−)-2-[(4'-trifluoromethane sulfonyloxy)phenyl]-N-methanesulfonyl propionamide (hereinbelow referred to as ladarixin) or a salt thereof, preferably its sodium salt, and (2S)-2-(4-{[4-(trifluoromethyl)-1,3-thiazol-2-yl] amino} phenyl) propanoic acid (hereinbelow referred to as DF2755Y), or a salt thereof, preferably its sodium salt (hereinbelow referred to as DF2755A) is immediately administered prophylactically to prevent or delay the onset of DN. Moreover, when a diabetic subject has developed early DN, the same subject is further tested for the IL8 level and this measured IL8 level is compared to a IL8 reference, and further tested for the level of urine protein and this measured level of urine protein is compared to a reference level of urine protein. When this diabetic subject has been demonstrated to have increased or elevated IL8 level compared to the reference IL8, and also demonstrated to have increased or elevated level of urine protein over the reference level urine protein, then an IL8 inhibitor, preferably a CXCR1 and/or CXCR2 inhibitor, more preferably a CXCR1 and CXCR2 inhibitor and, even more preferably, a compound selected from R(−)-2-[(4-isobutylphenyl)propionyl]-methanesulfonamide (hereinbelow referred to as reparixin) or a salt thereof, preferably its lysine salt, R(−)-2-[(4'-trifluoromethane sulfonyloxy)phenyl]-N-methanesulfonyl propionamide (hereinbelow referred to as ladarixin) or a salt thereof, preferably its sodium salt, and (2S)-2-(4-{[4-(trifluoromethyl)-1,3-thiazol-2-yl] amino} phenyl) propanoic acid (hereinbelow referred to as DF2755Y), or a salt thereof, preferably its sodium salt (hereinbelow referred to as DF2755A) is immediately administered prophylactically to treat, prevent and/or delay the progression of DN in that diabetic subject.

In one embodiment of the first object of the invention, also in combination with any of the previous embodiments, provided herein is a method of treatment of diabetic nephropathy or prevention, reduction of the risk or delay of the onset or progression of diabetic nephropathy in a subject, the method comprising: (a) determining whether the subject has at least one of the following single nucleotide polymorphisms (SNPs) at the CXCR1 locus: s13006838, rs4674308; rs4674309; rs3755042; rs7601872; and rs664514; (b) measuring the level of IL8 in a sample obtained from the subject; (c) comparing the measured IL8 level with a reference; (d) measuring the protein level in a sample obtained from the subject; (e) comparing the measured protein level with a protein reference and (f) administering an IL8 inhibitor, preferably a CXCR1 and/or CXCR2 inhibitor, more preferably a CXCR1 and CXCR2 inhibitor and, even more preferably, a compound selected from R(−)-2-[(4-isobutylphenyl)propionyl]-methanesulfonamide (hereinbelow referred to as reparixin) or a salt thereof, preferably its lysine salt, R(−)-2-[(4'-trifluoromethane sulfonyloxy)phenyl]-N-methanesulfonyl propionamide (hereinbelow referred to as ladarixin) or a salt thereof, preferably its sodium salt, and (2S)-2-(4-{[4-(trifluoromethyl)-1,3-thiazol-2-yl]amino} phenyl) propanoic acid (hereinbelow referred to as DF2755Y), or a salt thereof, preferably its sodium salt (hereinbelow referred to as DF2755A) to the subject when the subject has at least one of the SNPs, has increased protein in the urine and has increased IL8. In one embodiment, the sample for protein level analysis is a urine sample. In one embodiment, the method further comprises obtaining a sample of urine from the subject for protein level analysis. In one embodiment, the sample for IL8 level analysis is a urine, a serum, blood or plasma sample. In one embodiment, the method further comprises obtaining a sample of from the subject for IL8 analysis. In real life practice, when a subject has been diagnosed with diabetes but has not developed diabetic nephropathy, the genome of the same individual is further tested for the described SNPs, and the same individual is further tested for the IL8 level and tested for the level of urine protein. The measured IL8 level is compared to a reference IL8 and the measured level of urine protein is compared to a reference level of urine protein. When this diabetic subject has been demonstrated to have at least one of the described SNPs, and demonstrated to have an increased or elevated IL8 level compared to the reference IL8, and an increased or elevated level of urine protein over the reference level urine protein, then Reparixin and/or Ladarixin is/are immediately administered prophylactically to prevent the onset of diabetic nephropathy. Moreover, when a diabetic subject has developed early diabetic nephropathy, the genome of the same individual is further tested for the described SNPs, and the same individual is further tested for the IL8 level and tested for the level of urine protein. The measured IL8 level is compared to a reference IL8 and the measured level of urine protein is compared to a reference level of urine protein. When this diabetic subject has been demonstrated to have at least one of the described SNPs, and demonstrated to have an increased or elevated IL8 level compared to the reference IL8, and an increased or elevated level of urine protein over the reference level urine protein, then an IL8 inhibitor, preferably a CXCR1 and/or CXCR2 inhibitor, more preferably a CXCR1 and CXCR2 inhibitor and, even more preferably, a compound selected from R(−)-2-[(4-isobutylphenyl)propionyl]-methanesulfonamide (hereinbelow referred to as reparixin) or a salt thereof, preferably its lysine salt, R(−)-2-[(4'-trifluoromethane sulfonyloxy)phenyl]-N-methanesulfonyl propionamide (hereinbelow referred to as ladarixin) or a salt thereof, preferably its sodium salt, and (2S)-2-(4-{[4-(trifluoromethyl)-1,3-thiazol-2-yl]amino} phenyl) propanoic acid (hereinbelow referred to as DF2755Y), or a salt thereof, preferably, its sodium salt (hereinbelow referred to as DF2755A) is immediately administered prophylactically to prevent and/or delay the progression of diabetic nephropathy in that diabetic subject. It is contemplated that early application of an IL8 inhibitor, preferably a CXCR1 and/or CXCR2 inhibitor, more preferably a CXCR1 and CXCR2 inhibitor and, even more preferably, a compound selected from R(−)-2-[(4-isobutylphenyl)propionyl]-methanesulfonamide (hereinbelow referred to as reparixin) or a salt thereof, preferably its lysine salt, R(−)-2-[(4'-trifluoromethane sulfonyloxy)phenyl]-N-methanesulfonyl propionamide (hereinbelow referred to as ladarixin) or a salt thereof, preferably its sodium salt, and (2S)-2-(4-{[4-(trifluoromethyl)-1,3-thiazol-2-yl]amino} phenyl) propanoic acid (hereinbelow referred to as DF2755Y), or a salt thereof, preferably its sodium salt (hereinbelow referred to as DF2755A), would prolong the duration towards end-stage renal disease or chronic renal failure in these individual.

In one embodiment of each of the above objects of the invention, also in combination with any of the previous embodiments, in said method or use an effective amount of an IL8 inhibitor, preferably a CXCR1 and/or CXCR2 inhibitor, more preferably a CXCR1 and CXCR2 inhibitor and, even more preferably, a compound selected from R(−)-2-[(4-isobutylphenyl)propionyl]-methanesulfonamide (hereinbelow referred to as reparixin) or a salt thereof, preferably its lysine salt, R(−)-2-[(4'-trifluoromethane sulfonyloxy) phenyl]-N-methanesulfonyl propionamide (hereinbelow referred to as ladarixin) or a salt thereof, preferably its sodium salt, and (2S)-2-(4-{[4-(trifluoromethyl)-1,3-thiazol-2-yl]amino} phenyl) propanoic acid (hereinbelow referred to as DF2755Y), or a salt thereof, preferably its sodium salt (hereinbelow referred to as DF2755A), is administered to the subject.

In another embodiment of each of the above objects of the invention, also in combination with any of the previous embodiments, in said method or use an effective amount of an IL8 inhibitor, preferably a CXCR1 and/or CXCR2 inhibitor, more preferably a CXCR1 and CXCR2 inhibitor and, even more preferably, a compound selected from R(−)-2-[(4-isobutylphenyl)propionyl]-methanesulfonamide (hereinbelow referred to as reparixin) or a salt thereof, preferably its lysine salt, R(−)-2-[(4'-trifluoromethane sulfonyloxy) phenyl]-N-methanesulfonyl propionamide (hereinbelow referred to as ladarixin) or a salt thereof, preferably its sodium salt, and (2S)-2-(4-{[4-(trifluoromethyl)-1,3-thiazol-2-yl]amino} phenyl) propanoic acid (hereinbelow referred to as DF2755Y), or a salt thereof, preferably its sodium salt (hereinbelow referred to as DF2755A), in admixture with a pharmaceutically acceptable carrier is administered to the subject.

In another embodiment of each of the above objects of the invention, also in combination with any of the previous embodiments, in said method or use a composition comprising an effective amount of an IL8 inhibitor, preferably a CXCR1 and/or CXCR2 inhibitor, more preferably a CXCR1 and CXCR2 inhibitor and, even more preferably, a compound selected from R(−)-2-[(4-isobutylphenyl)propionyl]-methanesulfonamide (hereinbelow referred to as reparixin) or a salt thereof, preferably its lysine salt, R(−)-2-[(4'- trifluoromethane sulfonyloxy)phenyl]-N-methanesulfonyl propionamide (hereinbelow referred to as ladarixin) or a salt thereof, preferably its sodium salt, and (2S)-2-(4-{[4-(trifluoromethyl)-1,3-thiazol-2-yl] amino} phenyl) propanoic acid (hereinbelow referred to as DF2755Y), or a salt thereof, preferably its sodium salt (hereinbelow referred to as DF2755A) is administered to the subject. Preferably, said composition comprises a pharmaceutically acceptable carrier. Preferably, the compositions further comprises at least one other active molecule for diabetes, and/or metabolic syndrome, and/or a cardiovascular disease, and/or high blood pressure.

For example, diabetes is generally treated using one or a combination of medications including sulfonylureas, meglitinides, biguanides, thiazolidinediones, alpha-glucosidase inhibitors, and DPP-4 inhibitors. In one embodiment of any method described, the IL8 inhibitor, preferably a CXCR1 and/or CXCR2 inhibitor, more preferably a CXCR1 and CXCR2 inhibitor and, even more preferably, a compound selected from R(−)-2-[(4-isobutylphenyl)propionyl]-methanesulfonamide (hereinbelow referred to as reparixin) or a salt thereof, preferably its lysine salt, R(−)-2-[(4'-trifluoromethane sulfonyloxy)phenyl]-N-methanesulfonyl propionamide (hereinbelow referred to as ladarixin) or a salt thereof, preferably its sodium salt, and (2S)-2-(4-{[4-(trifluoromethyl)-1,3-thiazol-2-yl] amino} phenyl) propanoic acid (hereinbelow referred to as DF2755Y) or a salt thereof, preferably its its sodium salt (hereinbelow referred to as DF2755A), is administered with at least one active molecule used to treat diabetes, preferably selected from sulfonylureas, meglitinides, biguanides, thiazolidinediones, alpha-glucosidase inhibitors, and DPP-4 inhibitors.

For example, the described at least one other active molecule is insulin, an angiotensin-converting enzyme (ACE) inhibitor, an angiotensin-II receptor antagonists (AII-RAs), a drug or agent that lowers the blood HbA1c (e.g. telenzepine and sertraline described in U.S. Pat. No. 8,440,655, the contents of which are incorporated herein by reference in their entirety). In one embodiment of any method described, the IL8 inhibitor, preferably a CXCR1 and/or CXCR2 inhibitor, more preferably a CXCR1 and CXCR2 inhibitor and, even more preferably, a compound selected from R(−)-2-[(4-isobutylphenyl)propionyl]-methanesulfonamide (hereinbelow referred to as reparixin) or a salt thereof, preferably its lysine salt, R(−)-2-[(4'-trifluoromethane sulfonyloxy)phenyl]-N-methanesulfonyl propionamide (hereinbelow referred to as ladarixin) or a salt thereof, preferably its sodium salt, and (25)-2-(4-{[4-(trifluoromethyl)-1,3-thiazol-2-yl] amino} phenyl) propanoic acid (hereinbelow referred to as DF2755Y) or a salt thereof, preferably its sodium salt (hereinbelow referred to as DF2755A), is administered with at least one active principle including an ACE inhibitor, an AIIRA, telenzepine and sertraline.

In another embodiment of each of the above objects of the invention, also in combination with any of the previous embodiments, in said method or use the IL8 inhibitor, preferably a CXCR1 and/or CXCR2 inhibitor, more preferably a CXCR1 and CXCR2 inhibitor and, even more preferably, a compound selected from R(−)-2-[(4-isobutylphenyl)propionyl]-methanesulfonamide (hereinbelow referred to as reparixin) or a salt thereof, preferably its lysine salt, R(−)-2-[(4'-trifluoromethane sulfonyloxy)phenyl]-N-methanesulfonyl propionamide (hereinbelow referred to as ladarixin) or a salt thereof, preferably its sodium salt, and (2S)-2-(4-{[4-(trifluoromethyl)-1,3-thiazol-2-yl] amino} phenyl) propanoic acid (hereinbelow referred to as DF2755Y) or a salt thereof, preferably its sodium salt (hereinbelow referred to as DF2755A) is administered in association with one or more anti-diabetic agents.

In another embodiment of each of the above objects of the invention, also in combination with any of the previous embodiments, in said method or use the IL8 inhibitor, preferably a CXCR1 and/or CXCR2 inhibitor, more preferably a CXCR1 and CXCR2 inhibitor and, even more preferably, a compound selected from R(−)-2-[(4-isobutylphenyl)propionyl]-methanesulfonamide (hereinbelow referred to as reparixin) or a salt thereof, preferably its lysine salt, R(−)-2-[(4'-trifluoromethane sulfonyloxy)phenyl]-N-methanesulfonyl propionamide (hereinbelow referred to as ladarixin) or a salt thereof, preferably its sodium salt, and (2S)-2-(4-{[4-(trifluoromethyl)-1,3-thiazol-2-yl] amino} phenyl) propanoic acid (hereinbelow referred to as DF2755Y) or a salt thereof, preferably its sodium salt (hereinbelow referred to as DF2755A) is administered with at least one other active molecule for diabetes, and/or metabolic syndrome, and/or cardiovascular disease, and/or high blood pressure.

In one embodiment of each of the above objects of the invention, also in combination with any of the previous embodiments, in said method or use the IL8 inhibitor, preferably a CXCR1 and/or CXCR2 inhibitor, more preferably a CXCR1 and CXCR2 inhibitor and, even more preferably, a compound selected from R(−)-2-[(4-isobutylphenyl)propionyl]-methanesulfonamide (hereinbelow referred to as reparixin) or a salt thereof, preferably its lysine salt, R(−)-2-[(4'-trifluoromethane sulfonyloxy)phenyl]-N-methanesulfonyl propionamide (hereinbelow referred to as ladarixin) or a salt thereof, preferably its sodium salt, and (2S)-2-(4-{[4-(trifluoromethyl)-1,3-thiazol-2-yl] amino} phenyl) propanoic acid (hereinbelow referred to as DF2755Y) or a salt thereof, preferably its sodium salt (hereinbelow referred to as DF2755A), is systemically administered.

In one embodiment of each of the above objects of the invention, also in combination with any of the previous embodiments, in said method or use the IL8 inhibitor, preferably a CXCR1 and/or CXCR2 inhibitor, more preferably a CXCR1 and CXCR2 inhibitor and, even more preferably, a compound selected from R(−)-2-[(4-isobutylphenyl)propionyl]-methanesulfonamide (hereinbelow referred to as reparixin) or a salt thereof, preferably its lysine salt, R(−)-2-[(4'-trifluoromethane sulfonyloxy)phenyl]-N-methanesulfonyl propionamide (hereinbelow referred to as ladarixin) or a salt thereof, preferably its sodium salt, and (2S)-2-(4-{[4-(trifluoromethyl)-1,3-thiazol-2-yl] amino} phenyl) propanoic acid (hereinbelow referred to as DF2755Y) or a salt thereof, preferably its sodium salt (hereinbelow referred to as DF2755A), is administered in a sustained release formulation.

In one embodiment of each of the above objects of the invention, also in combination with any of the previous embodiments, in said method or use the IL8 inhibitor, preferably a CXCR1 and/or CXCR2 inhibitor, more preferably a CXCR1 and CXCR2 inhibitor and, even more preferably, a compound selected from R(−)-2-[(4-isobutylphenyl)propionyl]-methanesulfonamide (hereinbelow referred to as reparixin) or a salt thereof, preferably its lysine salt, R(−)-2-[(4'-trifluoromethane sulfonyloxy)phenyl]-N-methanesulfonyl propionamide (hereinbelow referred to as ladarixin) or a salt thereof, preferably its sodium salt, and (2S)-2-(4-{[4-(trifluoromethyl)-1,3-thiazol-2-yl] amino} phenyl) propanoic acid (hereinbelow referred to as DF2755Y) or a salt thereof, preferably its sodium salt (hereinbelow referred to as DF2755A) is administered in a sub-therapeutic amount.

In one embodiment of each of the above objects of the invention, also in combination with any of the previous embodiments, in said method or use the IL8 inhibitor, preferably a CXCR1 and/or CXCR2 inhibitor, more preferably a CXCR1 and CXCR2 inhibitor and, even more preferably, a compound selected from R(−)-2-[(4-isobutylphenyl)propionyl]-methanesulfonamide (hereinbelow referred to as reparixin) or a salt thereof, preferably its lysine salt, R(−)-2-[(4'-trifluoromethane sulfonyloxy)phenyl]-N-methanesulfonyl propionamide (hereinbelow referred to as ladarixin) or a salt thereof, preferably its sodium salt, and (2S)-2-(4-{[4-(trifluoromethyl)-1,3-thiazol-2-yl] amino} phenyl) propanoic acid (hereinbelow referred to as DF2755Y) or a salt thereof, preferably its sodium salt (hereinbelow referred to as DF2755A), is administered in a therapeutically effective amount.

In one embodiment of each of the above objects of the invention, also in combination with any of the previous embodiments, in said method or use the IL8 inhibitor, preferably a CXCR1 and/or CXCR2 inhibitor, more preferably a CXCR1 and CXCR2 inhibitor and, even more preferably, a compound selected from R(−)-2-[(4-isobutylphenyl)propionyl]-methanesulfonamide (hereinbelow referred to as reparixin) or a salt thereof, preferably its lysine salt, R(−)-2-[(4'-trifluoromethane sulfonyloxy)phenyl]-N-methanesulfonyl propionamide (hereinbelow referred to as ladarixin) or a salt thereof, preferably its sodium salt, and (2S)-2-(4-{[4-(trifluoromethyl)-1,3-thiazol-2-yl] amino} phenyl) propanoic acid (hereinbelow referred to as DF2755Y) or a salt thereof, preferably its sodium salt (hereinbelow referred to as DF2755A) is administered in a prophylactically effective amount.

In one embodiment, the IL8 inhibitor, preferably a CXCR1 and/or CXCR2 inhibitor, more preferably a CXCR1 and CXCR2 inhibitor and, even more preferably, a compound selected from R(−)-2-[(4-isobutylphenyl)propionyl]-methanesulfonamide (hereinbelow referred to as reparixin) or a salt thereof, preferably its lysine salt, R(−)-2-[(4'-trifluoromethane sulfonyloxy)phenyl]-N-methanesulfonyl propionamide (hereinbelow referred to as ladarixin) or a salt thereof, preferably its sodium salt, and (2S)-2-(4-{[4-(trifluoromethyl)-1,3-thiazol-2-yl] amino} phenyl) propanoic acid (hereinbelow referred to as DF2755Y) or a salt thereof, preferably its sodium salt (hereinbelow referred to as DF2755A) or pharmaceutical compositions thereof is formulated for systemic delivery. In one alternative embodiment, the IL8 inhibitor, preferably a CXCR1 and/or CXCR2 inhibitor, more preferably a CXCR1 and CXCR2 inhibitor and, even more preferably, a compound selected from R(−)-2-[(4-isobutylphenyl)propionyl]-methanesulfonamide (hereinbelow referred to as reparixin) or a salt thereof, preferably its lysine salt, R(−)-2-[(4'-trifluoromethane sulfonyloxy)phenyl]-N-methanesulfonyl propionamide (hereinbelow referred to as ladarixin) or a salt thereof, preferably its sodium salt, and (2S)-2-(4-{[4-(trifluoromethyl)-1,3-thiazol-2-yl] amino} phenyl) propanoic acid (hereinbelow referred to as DF2755Y) or a salt thereof, preferably its sodium salt (hereinbelow referred to as DF2755A), and pharmaceutical compositions thereof may be formulated for delivery to specific organs, for example but not limited to the kidney. In an alternative embodiments, the IL8 inhibitor, preferably a CXCR1 and/or CXCR2 inhibitor, more preferably a CXCR1 and CXCR2 inhibitor and, even more preferably, a compound selected from R(−)-2-[(4-isobutylphenyl)propionyl]-methanesulfonamide (hereinbelow referred to as reparixin) or a salt thereof, preferably its lysine salt, R(−)-2-[(4'-trifluoromethane sulfonyloxy)phenyl]-N-methanesulfonyl propionamide (hereinbelow referred to as ladarixin) or a salt thereof, preferably its sodium salt, and (2S)-2-(4-{[4-(trifluoromethyl)-1,3-thiazol-2-yl] amino} phenyl) propanoic acid (hereinbelow referred to as DF2755Y) or a salt thereof, preferably its sodium salt (hereinbelow referred to as DF2755A), or pharmaceutical compositions thereof may be formulated for aerosol application by inhalation the lung. Alternatively, the IL8 inhibitor, preferably a CXCR1 and/or CXCR2 inhibitor, more preferably a CXCR1 and CXCR2 inhibitor and, even more preferably, a compound selected from R(−)-2-[(4-isobutylphenyl)propionyl]-methanesulfonamide (hereinbelow referred to as reparixin) or a salt thereof, preferably its lysine salt, R(−)-2-[(4'-trifluoromethane sulfonyloxy)phenyl]-N-methanesulfonyl propionamide (hereinbelow referred to as ladarixin) or a salt thereof, preferably its sodium salt, and (2S)-2-(4-{[4-(trifluoromethyl)-1,3-thiazol-2-yl] amino} phenyl) propanoic acid (hereinbelow referred to as DF2755Y) or a salt thereof, preferably its sodium salt (hereinbelow referred to as DF2755A), or pharmaceutical compositions thereof may be formulated for a transdermal delivery, e.g. a skin patch. In some embodiments, the IL8 inhibitor, preferably a CXCR1 and/or CXCR2 inhibitor, more preferably a CXCR1 and CXCR2 inhibitor and, even more preferably, a compound selected from R(−)-2-[(4-isobutylphenyl)propionyl]-methanesulfonamide (hereinbelow referred to as reparixin) or a salt thereof, preferably its lysine salt, R(−)-2-[(4'-trifluoromethane sulfonyloxy)phenyl]-N-methanesulfonyl propionamide (hereinbelow referred to as ladarixin) or a salt thereof, preferably its sodium salt, and (2S)-2-(4-{[4-(trifluoromethyl)-1,3-thiazol-2-yl] amino} phenyl) propanoic acid (hereinbelow referred to as DF2755Y) or a salt thereof, preferably its sodium salt (hereinbelow referred to as DF2755A), or pharmaceutical compositions thereof may be enteric coated and formulated for oral delivery. In some embodiments, the IL8 inhibitor, preferably a CXCR1 and/or CXCR2 inhibitor, more preferably a CXCR1 and CXCR2 inhibitor and, even more preferably, a compound selected from R(−)-2-[(4-isobutylphenyl)propionyl]-methanesulfonamide (hereinbelow referred to as reparixin) or a salt thereof, preferably its lysine salt, R(−)-2-[(4'-trifluoromethane sulfonyloxy)phenyl]-N-methanesulfonyl propionamide (hereinbelow referred to as ladarixin) or a salt thereof, preferably its sodium salt, and (2S)-2-(4-{[4-(trifluoromethyl)-1,3-thiazol-2-yl] amino} phenyl) propanoic acid (hereinbelow referred to as DF2755Y) or a salt thereof, preferably its its sodium salt (hereinbelow referred to as DF2755A), or pharmaceutical compositions thereof may be encapsulated in liposomes or nanoparticles and formulated for slow sustained delivery in vivo. Sustained release formulations comprising, the IL8 inhibitors, preferably a CXCR1 and/or CXCR2 inhibitor, more preferably a CXCR1 and CXCR2 inhibitor and, even more preferably, a compound selected from R(−)-2-[(4-isobutylphenyl)propionyl]-methanesulfonamide (hereinbelow referred to as reparixin) or a salt thereof, preferably its lysine salt, R(−)-2-[(4'-trifluoromethane sulfonyloxy)phenyl]-N-methanesulfonyl propionamide (hereinbelow referred to as ladarixin) or a salt thereof, preferably its sodium salt, and (2S)-2-(4-{[4-(trifluoromethyl)-1,3-thiazol-2-yl] amino} phenyl) propanoic acid (hereinbelow referred to as DF2755Y) or a salt thereof, preferably its sodium salt (hereinbelow referred to as DF2755A), or pharmaceutical compositions thereof are also contemplated. For example, a sustained release formulation for a once a week administration. Alternatively, the IL8 inhibitor, preferably a CXCR1 and/or CXCR2 inhibitor, more preferably a CXCR1 and CXCR2 inhibitor and, even more preferably, a compound selected from R(−)-2-[(4-isobutylphenyl)propionyl]-methanesulfonamide (hereinbelow referred to as reparixin) or a salt thereof, preferably its lysine salt, R(−)-2-[(4'-trifluoromethane sulfonyloxy)phenyl]-N-methanesulfonyl propionamide (hereinbelow referred to as ladarixin) or a salt thereof, preferably its sodium salt, and (2S)-2-(4-{[4-(trifluoromethyl)-1,3-thiazol-2-yl] amino} phenyl) propanoic acid (hereinbelow referred to as DF2755Y) or a salt thereof, preferably its sodium salt (hereinbelow referred to as DF2755A), or pharmaceutical compositions thereof may be formulated for targeted delivery, e.g., encapsulated in liposomes or nanoparticles that are designed and feature targeting moiety to on the liposomes or nanoparticles.

The IL8 inhibitor, or pharmaceutical compositions thereof may be formulated, and administered by any known route. By way of example, the IL8 inhibitor and compositions thereof can be administered by a mucosal, pulmonary, topical, or other localized or systemic route (e.g., enteral and parenteral). The IL8 inhibitor, preferably a CXCR1 and/or CXCR2 inhibitor, more preferably a CXCR1 and CXCR2 inhibitor and, even more preferably, a compound selected from R(−)-2-[(4-isobutylphenyl)propionyl]-methanesulfonamide (hereinbelow referred to as reparixin) or a salt thereof, preferably its lysine salt, R(−)-2-[(4'-trifluoromethane sulfonyloxy)phenyl]-N-methanesulfonyl propionamide (hereinbelow referred to as ladarixin) or a salt thereof, preferably its sodium salt and (2S)-2-(4-{[4-(trifluoromethyl)-1,3-thiazol-2-yl] amino} phenyl) propanoic acid (hereinbelow referred to as DF2755Y) or a salt thereof, preferably its sodium salt (hereinbelow referred to as DF2755A) may be administered by any convenient route, for example by infusion or bolus injection, by absorption through epithelial or mucocutaneous linings (e.g., oral mucosa, rectal and intestinal mucosa, etc.) and may be administered together with other biologically active agents.

Routes of administration include, but are not limited to aerosol, direct injection, intradermal, transdermal (e.g., in slow release polymers), intravitreal, intramuscular, intraperitoneal, intravenous, subcutaneous, intranasal, epidural, topical, oral, transmucosal, buccal, rectal, vaginal, transdermal, intranasal and parenteral routes. "Parenteral" refers to a route of administration that is generally associated with injection, including but not limited to intraorbital, infusion, intraarterial, intracapsular, intracardiac, intradermal, intrahepatic, intrarogan, intramuscular, intraperitoneal, intrapulmonary, intraspinal, intrasternal, intrathecal, intrauterine, intravenous, subarachnoid, subcapsular, subcutaneous, transmucosal, or transtracheal. Any other therapeutically efficacious route of administration can be used, for example, infusion or bolus injection, absorption through epithelial or mucocutaneous linings, In various embodiments, administration can be inhaled in to the lung via aerosol administration, e.g. with nebulization. Administration also can be systemic or local.

For example, the IL8 inhibitor, or pharmaceutical compositions thereof may be administered as a formulation adapted for systemic delivery. In some embodiments, the IL8 inhibitor, preferably a CXCR1 and/or CXCR2 inhibitor, more preferably a CXCR1 and CXCR2 inhibitor and, even more preferably, a compound selected from R(−)-2-[(4-isobutylphenyl)propionyl]-methanesulfonamide (hereinbelow referred to as reparixin) or a salt thereof, preferably its lysine salt, R(−)-2-[(4'-trifluoromethane sulfonyloxy)phenyl]-N-methanesulfonyl propionamide (hereinbelow referred to as ladarixin) or a salt thereof, preferably its sodium salt and (2S)-2-(4-{[4-(trifluoromethyl)-1,3-thiazol-2-yl]amino} phenyl) propanoic acid (hereinbelow referred to as DF2755Y) or a salt thereof, preferably its sodium salt (hereinbelow referred to as DF2755A) or pharmaceutical compositions thereof may be administered as a formulation adapted for delivery to specific organs, for example but not limited to the kidney.

In addition, the IL8 inhibitor, or pharmaceutical compositions thereof may be administered together with other components of biologically active agents, such as pharmaceutically acceptable surfactants (e.g., glycerides), excipients (e.g., lactose), carriers, diluents and vehicles.

The IL8 inhibitor, or pharmaceutical compositions thereof may be administered therapeutically to a subject prior to, simultaneously with (in the same or different compositions) or sequentially with the administration of at least one other therapy for diabetes, metabolic syndrome, cardiovascular disease, and high blood pressure.

For parenteral (e.g., intravenous, subcutaneous, intramuscular) administration, the IL8 inhibitor, or pharmaceutical compositions thereof can be formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and non-aqueous vehicles such as fixed oils can also be used. The vehicle or lyophilized powder can contain additives that maintain isotonicity (e.g., sodium chloride, mannitol) and chemical stability (e.g., buffers and preservatives). The formulation is sterilized by commonly used techniques.

The dosage administered to a subject will vary depending upon a variety of factors, including the pharmacodynamic characteristics of the particular inhibitors, and its mode and route of administration; size, age, sex, health, body weight and diet of the recipient; nature and extent of symptoms of the disease being treated, kind of concurrent treatment, frequency of treatment, and the effect desired.

Usually, a daily dosage of IL8 inhibitor may be about 1 to 100 milligrams per kilogram of body weight, preferably, 5 to 80 milligrams per kilogram per day. Preferably, dosages given in divided doses 1 to 5 times a day by oral administration or given by continuous infusion for 1 or more cycles of 5 to 10 days are effective to obtain desired results. Second or subsequent administrations can be at a dosage which is the same, less than or greater than the initial or previous dose administered to the individual.

A second or subsequent administration is preferably during or immediately prior to relapse or a flare-up of the disease or symptoms of the disease. For example, second and subsequent administrations can be given between about one day to 30 weeks from the previous administration. Two, three, four or more total administrations can be delivered to the individual, as needed.

The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

Efficacy testing can be performed during the course of treatment using the methods described herein. Measurements of the degree of severity of a number of symptoms associated with a particular ailment are noted prior to the start of a treatment and then at later specific time period after the start of the treatment.

The precise dose to be employed in the formulation of the agent will also depend on the route of administration, and the seriousness of the disease or disorder, and should be decided according to the judgment of the practitioner and each patient's circumstances. Effective doses may be extrapolated from dose-response curves derived from in vitro or animal model test systems.

Efficacy testing can be performed during the course of treatment using the methods described herein. Measurements of the degree of severity of a number of symptoms associated with a particular ailment are noted prior to the start of a treatment and then at later specific time period after the start of the treatment. For example, when treating.

The skilled artisan will appreciate that certain factors may influence the dosage and timing required to effectively treat a subject, including but not limited to the severity of the disease or disorder, previous treatments, the general health and/or age of the subject, and other diseases present. The dose levels can also depend on the degree of nephropathy, the severity of the symptoms and the susceptibility of the subject to side effects. Treatment of a subject with a therapeutically effective dose can include a single treatment or a series of treatments. Estimates of effective dosages and in vivo half-lives for IL8 inhibitors can be made using conventional methodologies or on the basis of in vivo testing using an appropriate animal model, as known in the art, or as described herein. Preferred dosages are readily determinable by those of skill in the art by a variety of means.

Some embodiments of the technology described herein can be defined according to any of the following numbered paragraphs:

[1] A method of preventing the onset of diabetic nephropathy or the progression of diabetic nephropathy (DN) in a subject in need comprising administering an IL8 inhibitor, preferably a CXCR1 and/or CXCR2 inhibitor, more preferably Reparixin and/or Ladarixin, to the subject who has been diagnosed with diabetes.

[2] A method of preventing the onset of diabetic nephropathy (DN) or the progression of diabetic nephropathy in a subject in need comprising administering Reparixin and/or Ladarixin to the subject who has been diagnosed with diabetes and having an elevated level of IL8.

[3] The method of paragraph for 2, wherein the diabetes is Type 1 diabetes (T1D).

[4] The method of paragraph 1 or 2, wherein the diabetes is Type 2 diabetes (T2D).

[5] The method of any one of paragraphs 1-4, wherein the subject has normal proteinuria.

[6] The method of any one of paragraphs 1-4, wherein the subject has increased proteinuria.

[7] The method of any one of paragraphs 1-6, wherein the subject has at least one of the following single nucleotide polymorphisms at the CXCR1 locus: s13006838, rs4674308; rs4674309; rs3755042; rs7601872; and rs664514.

[8] The method of any one of paragraphs 1-7, further comprising measuring the protein level in a sample of urine from the subject.

[9] The method of any one of paragraphs 1-8, further comprising selecting subject having proteinuria.

[10] The method of any one of paragraphs 1-9, further comprising obtaining a sample of urine from the subject for urine protein level analysis.

[11] The method of any one of paragraphs 8-10, further comprising comparing the measured urine protein level with a urine protein reference.

[12] The method of paragraph 11, wherein the urine protein reference is the level of protein in urine samples obtained in normal healthy subjects that do not have any nephropathy.

[13] The method of any one of paragraphs 1-12, further comprising measuring the IL8 level in a sample obtained from the subject.

[14] The method of paragraph 13, wherein in the sample is a urine sample.

[15] The method of paragraph 13, wherein in the sample is a serum, blood or plasma sample.

[16] The method of any one of paragraphs 13-15, further comprising comparing the measured IL8 level with an IL8 reference.

[17] The method of paragraph 16, wherein the IL8 reference is the IL8 level in the respective samples obtained in normal healthy subjects that do not have any nephropathy.

[18] The method of any one of paragraphs 1-17, further comprising determining whether the subject has at least one of the following single nucleotide polymorphisms at the CXCR1 locus: s13006838, rs4674308; rs4674309; rs3755042; rs7601872; and rs664514.

[19] A method of preventing the onset of diabetic nephropathy (DN) or the progression of diabetic nephropathy (DN) in a subject who has been diagnosed with diabetes and microalbuminuria, the method comprising: (a) measuring the level of IL8 in a sample obtained from the subject; and (b) administering Reparixin and/or Ladarixin to the subject when the measured IL8 level is at least above 2.41 pg/ml.

[20] The method of paragraph 19, wherein the diabetes is Type 1 diabetes (T1D).

[21] The method of paragraph 19, wherein the diabetes is Type 2 diabetes (T2D).

[22] The method of any one of paragraphs 19-21, wherein in the sample is a urine sample.

[23] The method of any one of paragraphs 19-21, wherein in the sample is a serum, blood or plasma sample.

[24] The method of any one of paragraphs 19-23, wherein the subject has normal proteinuria.

[25] The method of any one of paragraphs 19-23, wherein the subject has increased proteinuria.

[26] The method of any one of paragraphs 19-25, wherein the subject has at least one of the following single nucleotide polymorphisms at the CXCR1 locus: s13006838, rs4674308; rs4674309; rs3755042; rs7601872; and rs664514.

[27] The method of any one of paragraphs 19-26, further comprising measuring the protein level in a sample of urine from the subject.

[28] The method of any one of paragraphs 19-27, further comprising obtaining a sample of urine from the subject for protein level analysis.

[29] The method of any one of paragraphs 19-28, further comprising comparing the urine protein level with a urine protein reference.

[30] The method of any one of paragraphs 19-29, wherein the urine protein reference is the level of protein in urine samples obtained in normal healthy subjects that do not have any nephropathy.

[31] The method of any one of paragraphs 19-30, wherein the IL8 reference is the IL8 level in the respective samples obtained in normal healthy subjects that do not have any nephropathy.

[32] The method of any one of paragraphs 19-31, further comprising determining whether the subject has at least one of the following single nucleotide polymorphisms at the CXCR1 locus: s13006838, rs4674308; rs4674309; rs3755042; rs7601872; and rs664514.

[33] A method of preventing the onset of diabetic nephropathy (DN) or the progression of diabetic nephropathy (DN) in a subject who has been diagnosed with diabetes, the method comprising: (a) measuring the level of protein in a urine sample obtained from the subject; (b) comparing the measured urine protein level with a urine protein reference; and (c) administering Reparixin and/or Ladarixin to the subject when the measured urine protein level is above the urine protein reference.

[34] The method of paragraph 33, wherein the diabetes has Type 1 diabetes (T1D).

[35] The method of paragraph 33, wherein the diabetes has Type 2 diabetes (T2D).

[36] The method of any one of paragraphs 33-35, wherein the urine protein reference is the level of protein in urine samples obtained in normal healthy subjects that do not have any nephropathy.

[37] The method of any one of paragraphs 33-35, further comprising measuring the IL8 level in a sample obtained from the subject.

[38] The method of paragraph 37, wherein in the sample is a urine sample.

[39] The method of paragraph 37, wherein in the sample is a serum, blood or plasma sample.

[40] The method any one of paragraphs 33-39, further comprising comparing the measured IL8 level with an IL8 reference.

[41] The method of paragraph 40, wherein the IL8 reference is the IL8 level in the respective samples obtained in normal healthy subjects that do not have any nephropathy.

[42] The method of any one of paragraphs 33-41, further comprising determining whether the subject has at least one of the following single nucleotide polymorphisms at the CXCR1 locus: s13006838, rs4674308; rs4674309; rs3755042; rs7601872; and rs664514.

[43] A method of preventing the onset of diabetic nephropathy (DN) or the progression of diabetic nephropathy (DN) in a subject who has been diagnosed with diabetes, the method comprising: (a) determining whether the subject has at least one of the following single nucleotide polymorphisms (SNPs) at the CXCR1 locus: s13006838, rs4674308; rs4674309; rs3755042; rs7601872; and rs664514; and (b) administering Reparixin and/or Ladarixin to the subject when the subject has at least one of the said SNPs.

[44] The method of paragraph 43, wherein the diabetes is Type 1 diabetes (T1D).

[45] The method of paragraph 43, wherein the diabetes is Type 2 diabetes (T2D).

[46] The method of any one of paragraphs 43-45, wherein the subject has normal proteinuria.

[47] The method of any one of paragraphs 43-45, wherein the subject has increased proteinuria.

[48] The method of any one of paragraphs 43-47, further comprising measuring the protein level in a sample of urine from the subject.

[49] The method of any one paragraphs 43-48, further comprising obtaining a sample of urine from the subject for urine protein level analysis.

[50] The method of paragraph 49, further comprising comparing the measured urine protein level with a urine protein reference.

[51] The method of paragraph 50, wherein the urine protein reference is the level of protein in urine samples obtained in normal healthy subjects that do not have any nephropathy.

[52] The method of any one paragraphs 43-51, further comprising measuring the IL8 level in a sample obtained from the subject.

[53] The method of paragraph 52, wherein in the sample is a urine sample.

[54] The method of paragraph 52, wherein in the sample is a serum, blood or plasma sample.

[55] The method of any one paragraphs 52-54, further comprising comparing the measured IL8 level with an IL8 reference.

[56] The method of paragraph 55, wherein the IL8 reference is the IL8 level in the respective samples obtained in normal healthy subjects that do not have any nephropathy.

[57] A method of treatment of diabetic nephropathy (DN) in a subject in need of treatment, the method comprising administering Reparixin and/or Ladarixin to the subject.

[58] The method of paragraph 57, wherein the subject has Type 1 diabetes (T1D).

[59] The method of paragraph 57, wherein the subject has Type 2 diabetes (T2D).

[60] The method of any one of paragraphs 57-59, wherein the subject has an elevated level of IL8.

[61] The method of any one paragraphs 57-60 wherein the subject has normal proteinuria.

[62] The method of any one paragraphs 57-61, wherein the subject has increased proteinuria.

[63] The method of paragraphs 57-62, further comprising measuring the IL8 level in a sample obtained from the subject.

[64] The method of paragraph 63, wherein in the sample is a urine sample.

[65] The method of paragraph 63, wherein in the sample is a serum, blood or plasma sample.

[66] The method of any one of paragraphs 63-65, further comprising comparing the measured IL8 level with an IL8 reference.

[67] The method of paragraph 66, wherein the IL8 reference is the IL8 level in the respective samples obtained in normal healthy subjects that do not have any nephropathy.

[68] The method of any one of paragraphs 57-67, wherein the subject has at least one of the following single nucleotide polymorphisms at the CXCR1 locus: s13006838, rs4674308; rs4674309; rs3755042; rs7601872; and rs664514.

[69] The method of paragraphs 57-68, further comprising determining whether the subject has at least one of the following single nucleotide polymorphisms at the CXCR1 locus: s13006838, rs4674308; rs4674309; rs3755042; rs7601872; and rs664514.

[70] The method of any one of paragraphs 1-69, wherein the subject has a value of glomerular filtration rate (GFR) above 60 ml/min/1.73 m².

[71] The method of paragraph 70, wherein the subject has a value of glomerular filtration rate above 90 ml/min/1.73 m².

[72] The method any one of paragraphs 1-71, wherein the subject has urinary level of IL8 higher than 2.41 pg/ml.

[73] The method of any one of paragraphs 1-71, wherein the subject has a measured rate of excretion of albumin between 30 and 300 mg per day.

[74] A method of treatment, the method comprising: (a) determining the level of IL8 in a urine sample for a subject; and (b) administering to said subject an effective amount of Reparixin and/or Ladarixin when the IL8 levels are at least 3-fold greater than the reference level.

[75] The method of paragraph 74, further comprising diagnosing the subject with diabetes.

[76] The method of paragraph 74, wherein the sample is a urine sample.

[77] The method of paragraph 63, wherein in the sample is a serum, blood or plasma sample.

[78] The method of paragraph 74, wherein the reference level is a IL8 level in the respective samples obtained in normal healthy subject that does not have any nephropathy.

[79] A method of treating hyperglycemia, the method comprising: (a) diagnosing a patient with hyperglycemia; and (b) administering to said patient an effective amount of Reparixin and/or Ladarixin.

[80] A method of treating hyperglycemia, the method comprising; administering to a patient in need thereof an effective amount of Reparixin and/or Ladarixin.

[81] A composition comprising, or consisting, or consisting essentially of Reparixin and/or Ladarixin for treating diabetic nephropathy, or for preventing, or reducing the risk, or delaying the onset or progression of diabetic nephropathy in a subject.

[82] A composition comprising, or consisting, or consisting essentially of Reparixin and/or Ladarixin for the manufacturing of a medicament for treating diabetic nephropathy, or preventing, or reducing the risk, or delaying the onset or progression of diabetic nephropathy in a subject.

[83] Use of a composition comprising, or consisting, or consisting essentially of Reparixin and/or Ladarixin for treating diabetic nephropathy, or preventing, or reducing the risk, or delaying the onset of progression of diabetic nephropathy in a subject.

[84] Use of a composition comprising, or consisting, or consisting essentially of Reparixin and/or Ladarixin for the manufacturing of a medicament for treating diabetic nephropathy, or preventing, or reducing the risk, or delaying the onset or progression of diabetic nephropathy in a subject.

Embodiments of this disclosure are further illustrated by the following example which should not be construed as limiting. The contents of all references cited throughout this application, as well as the figures and table are incorporated herein by reference.

Those skilled in the art will recognize, or be able to ascertain using not more than routine experimentation, many equivalents to the specific embodiments of the invention described herein. Such equivalents are intended to be encompassed by the following claims.

The references cited herein and throughout the specification are incorporated herein by reference.

EXAMPLES

Introduction

From the multiple complications carried by Diabetes Mellitus, Chronic Kidney Disease (CKD) has been established as the complication with the highest load on daily life and financial costs. CKD increases the risk of premature mortality and End Stage Renal Disease (ESRD) 1. The incidence of End Stage Renal Disease (ESRD) due to Diabetes has been increasing over the last two decades. Diabetes is the primary cause of ESRD on more than one third of patients on the western world 2. Over 5% of newly diagnosed patients with Type 2 Diabetes (T2D) will already have diabetic kidney disease, and an additional 30 to 40% will develop Diabetic Nephropathy (DN), usually within 10 years of diagnosis[3,4,5].

Patients with T2D present with modifications in the immunological system. Elevated levels of cytokines, chemokines and acute-phase proteins have been described in these patients 6,7; modification in immunological profile have been shown to increase apoptosis and tissue fibrosis 8. Patients with Type 1 Diabetes (T1D) have 6 to 7-fold higher urinary IL8 levels as compared to controls 9. Moreover, among patients with T1D with albuminuria, those with highest urinary IL8 levels at baseline, presented a faster decline of renal function.

IL8 is a chemokine that can be produced by leukocytes as monocytes 10, T lymphocytes, macrophages 11, or by non-leukocyte population like endothelial cells 12, podocytes 13, proximal tubular epithelial cells 14. This chemokine has two receptors CXCR-1 and CXCR-2, which are expressed by leukocytes cells as neutrophils, monocytes, CD8 T-cells, mast cells, natural killer cells, and are also expressed by non-leukocyte cells as endothelial cells 12, podocytes 13, fibroblasts 11.

In patients with Diabetes, hyperglycemia may trigger the production of IL8, thus, stimulating the expression of CXCR1/2 in auto and paracrine way. Activation of CXCR1/2 spreads within the podocytes and endothelial cells via CXCR1/2 cytoplasmic tail, which determines deactivation of the α3β1-integrin by competing with binding of talin to the cytoplasmic tail of α3β1-integrin (which is essential for α3β1-integrin activity; FIG. 6). This competitive binding causes paxillin deactivation with loss of podocyte physiologic structure and adhesion to the glomerular basal membrane. CXCR1/2 activation also leads to activation of the mTor pathway, causing metabolic alterations and oxidative damage. Taken together, these pathologic alterations ultimately cause podocyte structural and functional abnormalities and development of proteinuria (FIGS. 7A-6E and 8A-7F). The invention described herein shows that counteracting IL8 signaling with a clinically available CXCR1/2 antagonist will reduce the extent of podocytopathy in vitro and the progression of kidney injury in vivo, and provides a new therapeutic tool for DN.

Example 1

CXCR2 and KC expression is progressively increased in the glomeruli of STZ-induced C57BL/6 diabetic mice in vivo and localized in endothelial cells and podocytes.

In one model of DN db/db diabetic mice, the STZ-induced C57BL/6 diabetic mouse, the in vivo expression of KC (murine homologue of human IL8) and its receptor CXCR2

(murine homologue of human CXCR2) were evaluated. Diabetes is defined herein as blood glucose levels >250 mg/dl for 3 consecutive days. BD Logic Glucose Meter (Becton Dickinson, Franklin Lakes, N.J.) was used to measured glucose level in serum. At 7 weeks, the db/db mice presented with hyperglycemia but not DN. C57BL/6 mice and C57BL/6J Lepdb/db were obtained from Jackson Laboratory (Bar Harbor, Me.). Mice were housed in a pathogen-free environment; water and chow diet were provided ad libitum. All mice were male and were cared for and used following the guidelines for animal care and housing of Boston Children's Hospital and Harvard Medical School. Institutional Animal Care and Use Committee approved the protocol.

Kidneys from db/db mice at 8, 12 and 25 weeks of age were surgically removed using standard techniques. To perform standard light microscopy, kidneys were fixed in 4% buffered paraformaldehyde (PFA), dehydrated, and paraffin-embedded. AxioVision software 4.3 was used to record the images from Periodic Acid Schiff (PAS) and Trichrome staining. The evaluation of mesangial matrix was electronically performed using a macro built on the AxioVision analysis module (Carl Zeiss Spa, Thornwood, N.Y.). Glomeruli were identified as a region of interest (ROI) and mesangium was highlighted by a color threshold protocol. Binary images were then produced and mesangium was automatically calculated as percentage of the glomerular area. Image acquisition was performed with a Zeiss Axioscope 40FL microscope and AxioCam MRc5 digital video camera (Carl Zeiss SpA). AxioVision software 4.3 was used to record images and AxioVision analysis module to analyze the results (Carl Zeiss SpA).

KC and CXCR2 expression increased at the glomerular level in diabetic mice at 12 weeks of age, and the expression reach a peak at 28 week of age (data not shown). In addition at 28 weeks, the expression of CXCR2 and KC co-localize at glomerular level with CD 31 (endothelial cell marker) and synaptopodin (podocyte specific marker) in db/db C57BL/6 diabetic mice in vivo (data not shown). In contrast, kidneys obtained from non-diabetic C57BL/6 control mice at 7 weeks (baseline) of age did not express CXCR2 and KC.

Example 2

KC/CXCR2 axis blockade with Reparixin prevents urinary albumin excretion (UAE) increase in db/db mice and mitigates mesangial expansion.

In order to assess the potential role of IL8 blockade in DN progression, 7 weeks old db/db mice were treated with Reparixin 15 mg/kg (ip) twice a day for 18 weeks (up to 25 weeks of age). Briefly, animals were housed in metabolic cages (Nalgene) to separate feces and urine within a light-controlled environment and provided with water ad-libitum. Sample collection tubes passed below the cages and through small holes in the bottom of the light controlled environment.

Urine samples from db/db mice were collected through a metabolic cage at week 8, 12, and 25. The BeadLyte Mouse Multi-cytokine Beadmaster Kit (Millipore, Billerica, Mass.) was used according to the manufacturer's protocol to determine cytokine levels of IL8. Briefly, the supernatant was incubated with beads conjugated to the IL8 alone for a specified amount of time, and then with biotinylated reporters and streptavidin-phycoerythrin solution for 30 min. A Luminex100 reader (Luminex Corporation, Austin, Tex.) was used to measure the sample cytokine level.

Figure 11A:
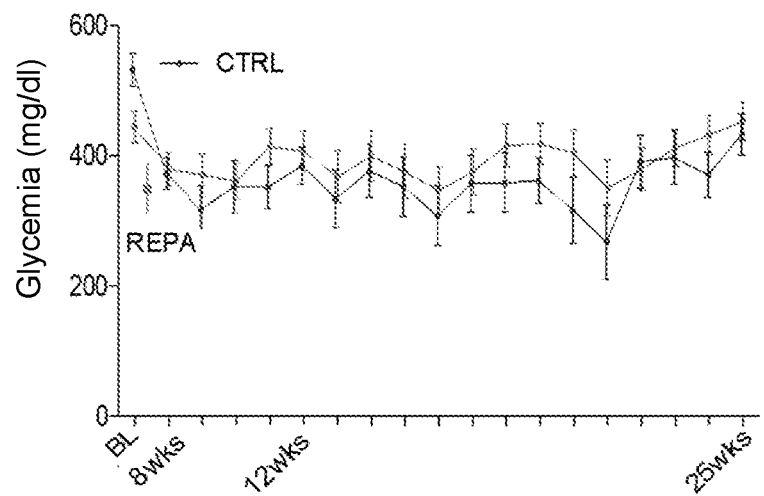
FIG. 11A presents experimental data showing the glycemia levels in vivo at the indicated time points in control or REPA treated DN db/db diabetic mice.
Figure 11B:
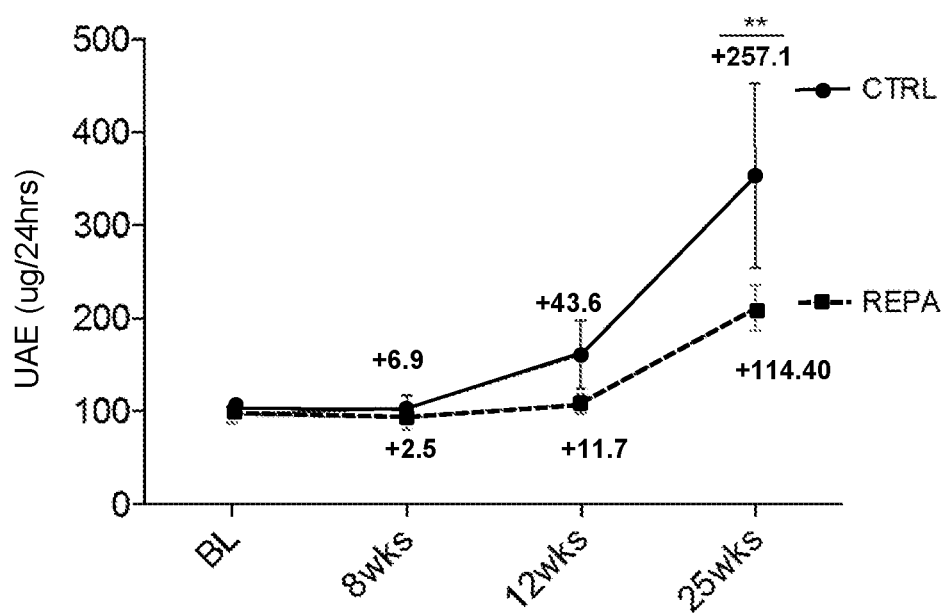
FIG. 11B presents experimental data showing the UAE levels in vivo at the indicated time points in control or REPA treated DN db/db diabetic mice.

While urinary albumin excretion increased in untreated control mice, in reparixin-treated mice, urinary albumin levels remained stable over time (FIGS. 1 and 11B) and were significantly lower than in control diabetic db/db mice at 25 weeks of age, showing a significant time-treatment interaction at the latest time point (Reparixin-treated-25 wks=211.1±24.4 vs. Ctrl-25 wks=353.8±99.4 ug/ml, $p<0.01$; FIG. 1). No effect on the glycemic control were observed in the treatment group (FIG. 11A). Histopathological examination of biopsies kidney from the above animals was carried out and Reparixin treatment showed a protective effect on kidneys of db/db mice at 25 weeks of age, where reduced mesangial expansion was evident in treated animals compared to control mice (data not shown).

Example 3

IL8 challenge causes loss of stress fibers, dose dependent increase in cortical actin and cell blebbing in podocytes in vitro.

Figure 10A:
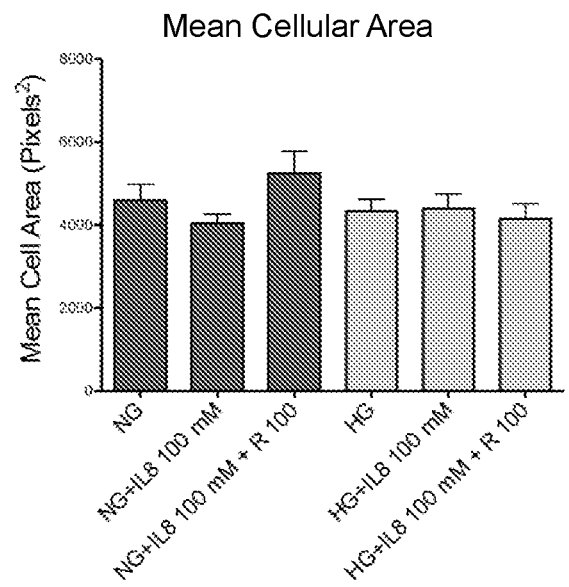
FIG. 10A presents experimental data showing mean cellular area of podocytes in the indicated condition, with or without Reparixin treatment.
Figure 10B:
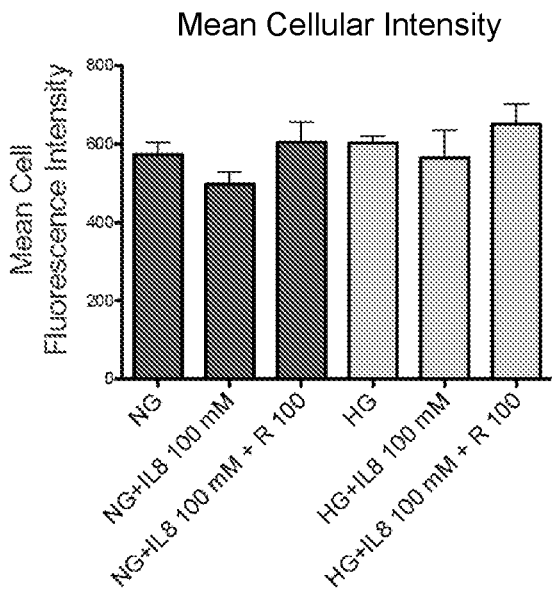
FIG. 10B presents experimental data showing mean cellular fluorescence intensity of podocytes in the indicated condition, with or without Reparixin treatment.

Human podocyte cells bearing a transgene for the thermosensitive (ts58A) variant of the SV40 T antigen, which make them responsive to interferon-γ for proliferation, were cultured and allowed to grow to 80% confluence at 33° C. (designated as day 0). Cells were then thermoshifted to 37° C., causing inactivation of the SV40 T antigen and cessation of cell replication. Podocytes were cultured at different glucose concentrations (normal glucose: 5 mM [NG]; high glucose: 30 mM [HG]) for 5 days Mannitol was used as an osmotic control for high glucose (mannitol 20 mM+glucose 10 mM) (FIGS. 10A and 10B).

Podocytes were grown on round glass coverslips (VWR, Radnor, Pa.) were fixed with paraformaldehyde and then permeabilized with 0.3% Triton X-100 (Fisher Scientific, Waltham, Mass.). Cells were incubated with rhodamine phalloidin (Invitrogen, Carlsbad, Calif.) to label F-actin networks and visualize stress fibers. Standard fluorescent microscopy was used to assess stress fiber formation. The percentage of cells containing intact actin filaments was assessed by manual cell counting.

Treatment with IL8 at the dosage of 100 nM caused loss of stress fibers (measured by phalloidin staining; Ctrl vs. IL8, $p<0.05$; FIG. 2A), dose dependent increase in cortical actin, cell blebbing and synaptopodin c expression (Ctrl vs. IL8, $p<0.05$; FIG. 2B) in human podocytes in vitro, both in NG and HG (data not shown) conditions; with the latter synergizing with the effect of IL8. These data support the hypothesis that IL8 induces a direct injury to podocytes.

Interestingly, reparixin treatment at the dose of 100 μM was able to rescue podocytes from IL8 induced damage (loss of stress fibers; increase cortical actin; cell blebbing and loss of synaptopodin expression) both in NG (data not shown) and HG (data not shown; and FIGS. 2A, 2B, 10A, and 10B).

Example 4

IL8 is expressed at glomerular level in a subset patients with T2D and DN and co-localizes with both CD-31 and Synaptopodin.

The expression of IL8 in kidney biopsies of 30 patients with Type-2 diabetes (T2D) and DKD at different stages of severity (from less severe to more severe: mesangial expansion; nodular transformation; and glomerulosclerosis) and from control individuals (with surgically removed cancer-affected kidneys) (data not shown) was measured by immunohistochemistry analysis, as described above. Histology data from this cohort were previously published by Fiorina et al. in 2013. The informed consent was approved by institutional review board of Hospital San Carlo (Milan, Italy) and/or Institutional Review Board approval at Azienda Ospedaliera di Parma, Parma, Italy prior to being signed by patients. A record of medical history was obtained from every patient, as was serum and urine sample to obtain kidney functional data. As a control, histologic samples from the unaltered kidney pole of patients who underwent unilateral nephrectomy for renal cancer (n=10) was used.

Material for routine light microscopy staining was fixed in 4% buffered paraformaldehyde (PFA), dehydrated, and paraffin-embedded. Images from PAS and Trichrome stainings were recorded using AxioVision software 4.3, and evaluation of mesangial matrix was performed electronically by a macro built on the AxioVision analysis module (Carl Zeiss SpA, Thornwood, N.Y.). Briefly, glomeruli were identified as region of interest (ROI) and mesangium highlighted by a colour threshold procedure. Binary images were then produced and mesangium automatically calculated as percentage of the glomerular area. Images acquisition was performed with a Zeiss Axioscope 40FL microscope and AxioCam MRc5 digital video camera (Carl Zeiss SpA). AxioVision software 4.3 was used to record images and AxioVision analysis module to analyze the results (Carl Zeiss SpA). Anti-human IL8 antibody was obtained from Abcam (Cambridge, Mass.). The staining was evaluated in 40 glomeruli per sample as number of positive hits per glomerulus.

As shown in FIGS. 3A and 3B, a correlation between stage of kidney damage and IL8 expression was found. IL8 expression was found to peak in early injury phases and progressively decrease following the loss of cellularity of the kidney parenchyma and the onset of fibrosis (data not shown; FIGS. 7A and 7B). The expression of IL8 in the glomerulus was highest during mesangial expression (data not shown; FIG. 3A; and Table 2): mean GFR=91.43±7.74 ml/min/1.73m2; IL8 histopathology score: 3±0.0 arbitrary units (AU)). A consistent reduction of IL8 staining was observed in the progression of glomeruli injury to nodular transformation (data not shown; FIG. 3A; and Table 2): mean GFR=62.29±6.75 ml/min/1.73m2; IL8 histopathology score: 1.5±0.41 arbitrary units (AU)) and glomerulo-sclerosis (data not shown; FIG. 3A; and Table 2: mean GFR=48.25±8.52 ml/min/1.73m2; IL8 histopathology score: 0.0±0.0 arbitrary units (AU)). Control subjects had fully conserved glomeruli and absent IL8 staining (data not shown; and FIG. 3A).

In addition, rt-PCR performed on above biopsies revealed an upregulation of IL8 mRNA levels in T2D patients compared to control individuals (IL8 mRNA: Diabetics vs. Ctrl: 3-fold-increase, p<0.05; FIG. 3B). Briefly, RNA from purified glomeruli was extracted using Trizol Reagent (Invitrogen), and qRTPCR analysis was performed using TaqMan assays (Life Technologies, Grand Island, N.Y.) according to the manufacturer's instructions. The normalized expression values were determined using the ΔΔCt method. Quantitative reverse transcriptase polymerase chain reaction (qRT-PCR) data were normalized for the expression of ACTB, and ΔΔCt values were calculated. Statistical analysis compared gene expression across all cell populations for each patient via one-way ANOVA followed by Bonferroni post-test for multiple comparisons between the population of interest and all other populations. Statistical analysis was performed also by using the software available RT2 profiler PCR Array Data Analysis (Qiagen). No significant difference was observed for CXCR1 and CXCR2 levels, detectable amount of transcript (IL8 mRNA: Diabetics vs. Ctrl, p<0.05; FIG. 7C) was identified. Moreover, IL8 was expressed at glomerular level and co-localized with synaptopodin (podocyte marker) and CD-31 (endothelial marker) (data not shown).

The data obtained reveal selective glomerular localization and co-expression with synaptopodin at the podocyte level and CD31 at the endothelial level (data not shown). Confirming the evidences presented in FIGS. 3A and 3B, IL8 expression progressively decreases following the loss of cellularity of the kidney parenchyma and the onset of fibrosis (data not shown).

Example 5

Urinary IL8 levels are higher in T2D patients with worse kidney function.

In order to confirm if IL8 is relevant for DKD in type 2 diabetic patients (T2D), and particularly if urinary IL8 levels are modified according to albuminuria status, we took advantage of the Joslin cohort of individuals with T2D. This cohort comprises individuals with T2D followed for 8-12 years of follow up and censored for decline in renal function, onset of proteinuria and end stage renal disease (ESRD). The levels at baseline of urinary IL8 was measured by Luminex in 1246 T2D patients divided as follows: 702 normo-albuminuric, 390 microalbuminuric, 156 macroalbuminuric and 25 healthy subjects. We evaluated as a first step, the urinary levels of IL8 at baseline and found that microalbuminuric individuals that higher levels of urinary IL8 levels were associated with the highest levels of albuminuria.

Briefly, urine samples from each patient were tested for human IL8 concentration with a magnetic microsphere-based Milliplex MAP® assay (EMD Millipore, Billerica Mass.) for Luminex® xMAP® technologies, used according to the manufacturer's protocol (4). Briefly, urine samples were allowed to gradually thaw at +4C and then spun at 10,000 g for 10 minutes. Urine samples were then infused with magnetic beads and incubated overnight at +4° C. under gentle shaking movement. Then biotinylated reporters were added, and streptavidin-phycoerythrin solution was incubated with samples for 30 min at room temperature. Samples were read with a Luminex200® reader (Luminex Corp, Austin, Tex.) and results analyzed with xPONENT® software package (Luminex Corp). Data are expressed as mean±standard error. When 2 groups were compared cross-sectionally, two-sided unpaired Student t-test (for parametric data) or Mann-Whitney tests (for non-parametric data) were used according to distribution. When more than 2 groups were compared, ANOVA (for parametric data) and Kruskal-Wallis tests (for non-parametric data) were used. A P value of less than 0.05 (by two-tailed testing) was considered an indicator of statistical significance. Data were analyzed and graphs created using GraphPad Prism software (GraphPad Software, Inc., San Diego, Calif.).

Figure 8A:
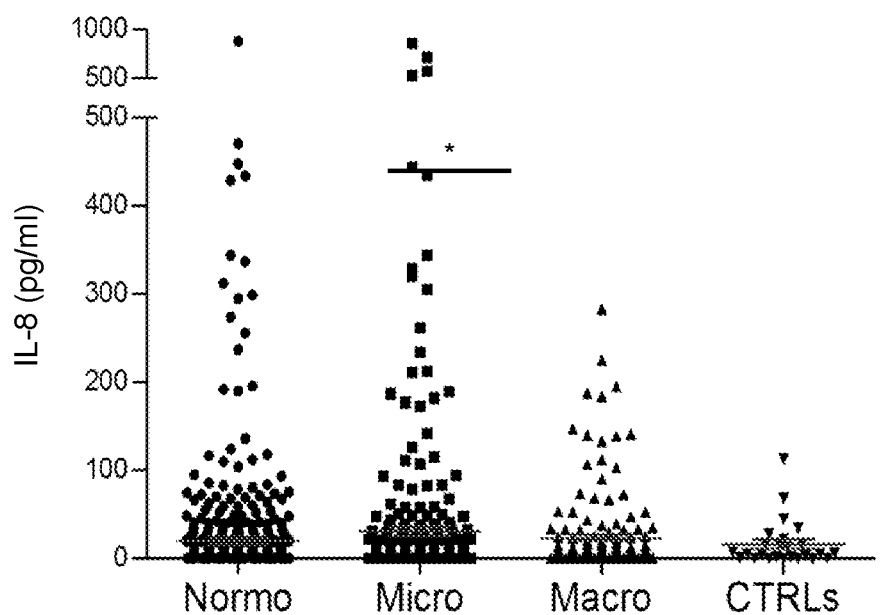
FIG. 8A presents experimental data showing patients with micro-albuminuria displayed higher levels of urinary IL8 as compared to norm-albuminuric patients.
Figures 8B, 8C:
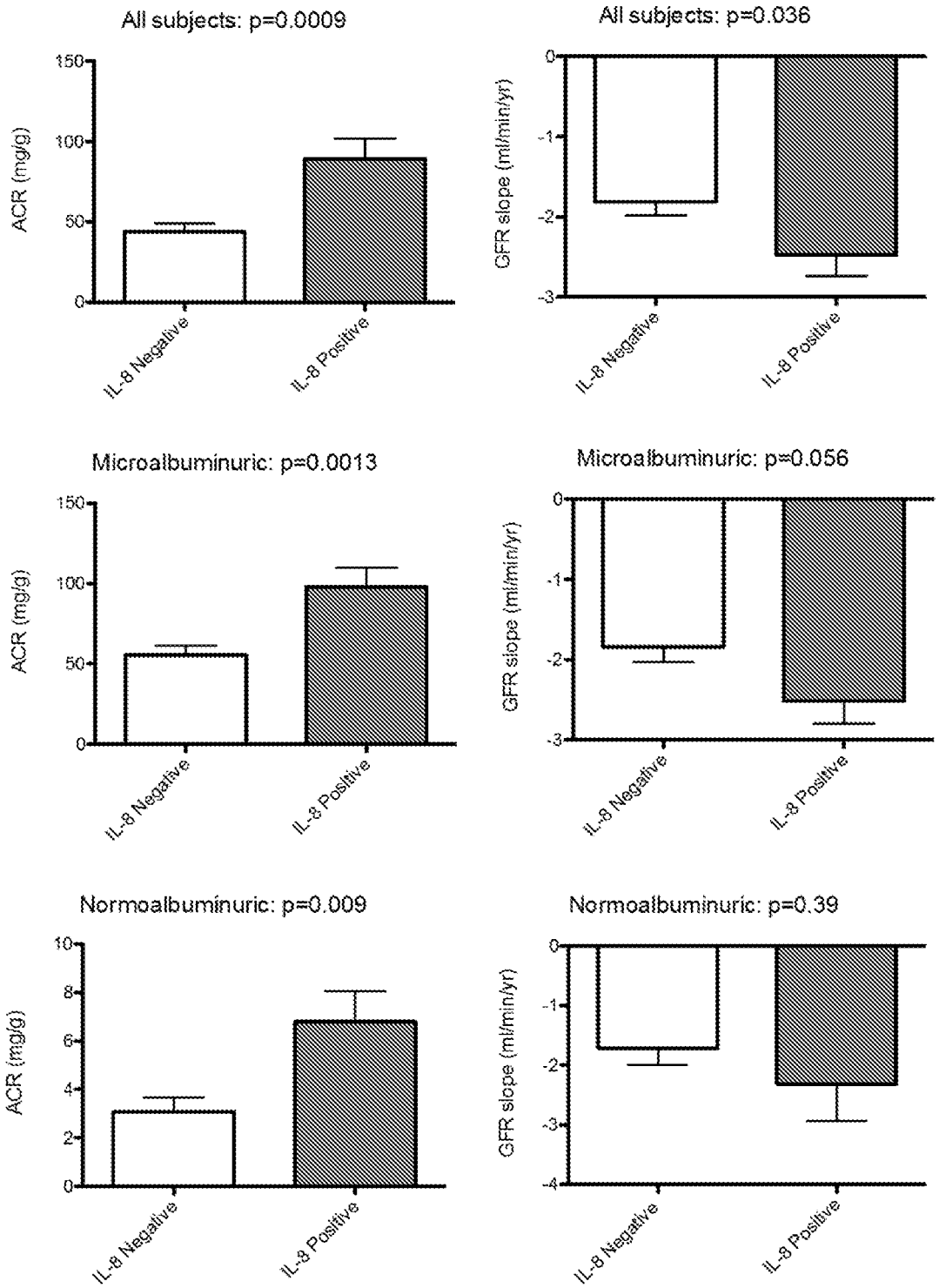
FIG. 8B presents experimental data showing of all the 389 patients and its subsets of normoalbumminuric and microalbuminuric, those patients who presented a positive test of IL8 in urine, also presented a significantly higher value of ACR.
FIG. 8C presents experimental data showing of all the 389 patients and its subsets of normoalbuminuric and microalbuminuric, those patients having a positive urinary IL8 test, within the microalbuminuric and normoalbuminuric groups had a significantly steeper GFR slope.

The data obtained show that patients with micro-albuminuria displayed higher levels of urinary IL8 as compared to normo-albuminuric individuals [IL8: normo-albuminurics=19.69±3.70 vs. micro-albuminurics=30.28±5.42 pg/ml, p<0.001; FIGS. 6A, 6B, and 8A). Next, patients with micro-albuminuria (that are more prone to progress to impaired renal function) were assessed and the correlation between urinary IL8 concentration and loss of renal function as measured by urinary albumin:creatinine ratio (ACR; mg/g) was determined. Patients with high urinary IL8 at baseline (defined as superior to the median distribution of IL8 in the micro-albuminuric patients cohort), showed significantly worse renal function [ACR: Q3-Q4 (High IL8)=101.7±13.0 vs. Q1-Q2 (Low IL8)=58.5±6.5 mg/g, p=0.003, FIG. 5B). The median threshold for IL8 was 2.41 pg/ml. Additionally, data from the Joslin cohort was analyzed; 389 patients with normal renal function (GFR≥60 ml/min) and albuminuria in the normo/micro range that were followed for 5 years. The albumin:creatinine ratio (ACR: mg/g) and the slope of GFR was calculated for all patients. Those patients who were above the median distribution of IL8 in the normo and microalbuminuric cohort showed an ACR significantly higher than those from below the median (FIG. 8D). Among all the 389 patients and its subsets of normoalbuminuric and microalbuminuric, those patients who presented a positive test of IL8 in urine, also presented a significantly higher value of ACR (FIG. 8B). GFR slope was 1.6 ml/year in the 5-year follow-up period (IQR 0.5-3.3) and 55 patients had a "hard renal outcome" according to the FDA definition (ESRD, death for any cause, or 30% of kidney function loss). IL8 values did not quantitatively correlate with any of the considered follow-up variables (GFR slope, risk of renal outcome, baseline proteinuria levels). Subsequently, the patients having a positive urinary IL8 test were compared to patients with negative ones. Positive patients had a significantly steeper GFR slope (2.47±0.26 vs. 1.81±0.16 ml/min/yr p=0.036, FIG. 8C); this trend was observed also within the microalbuminuric group (2.5±0.29 vs. 1.84±0.19 ml/min/yr p=0.056, FIG. 8C) and the normoalbuminuric group (2.3±0.7 vs. 1.71±0.28 ml/min/yr p=0.39, FIG. 8C).

Regarding the composite renal outcome, 368 on 389 patients had valid data; 41/55 events (74.5%) had a positive urinary IL8 value. Event risk was 19% in IL8 positive vs. 9% in IL8 negative patients with an absolute risk increase of 10% and a relative increase of 111% ($\chi$2 test, p=0.0096, data not shown). Among all the subjects, those with an IL8 positive urine had 1.33 (95% C.I. 1.11 to 1.60) the risk of suffer an event (ESRD, death for any cause, or 30% of kidney function loss). Similarly, the risk in early stages of micro and normo-albuminuria, had a risk of 1.29 and 1.76, respectively (95% C.I. 1.05 to 1.58 and 95% C.I. 1.41 to 2.20; FIG. 8E).

Example 6

Identification of Single Nucleotide Polymorphism at CXCR1 Gene be Associated with DKD To assess the importance of IL8-CXR1/2 axis on DN in humans, samples from individuals with T2D from the Joslin Study of Genetics of Nephropathy were evaluated. Data from this cohort has been published (available in dbGaP, found on the world wide web page of the National Institute of Health, gap, accession number phs000302.v1.p1). Patients included in this cohort were monitored for 8 to 12 years of follow-up and censored for proteinuria, decline on renal function, and ESRD. Experimental investigation to determine if there is an association with an accelerated progression of DN and any spontaneous genetic variants of IL8, CXCR1 or CXCR2 loci was performed. 326 patients with T2D, with and without DN, were screened and genotyped to evaluate whether any single nucleotide polymorphism (SNP) at those loci could influence on DN acceleration.

In details, diabetic kidney disease cases from this collection were randomly selected for whole genome genotyping on Illumina's Human CNV370v1 genotyping array (data available in dbGaP at the World Wide Web page of the National Institute of Health, accession numberphs000302.v1.p1) (Illumina, San Diego, Calif.). The application of quality control metrics for minor allele frequency (MAF) <0.01, rejection of Hardy-Weinberg assumptions (P≤10-5) and differential rates of missing data (by case/control status) resulted in high-quality genotypic data for 324,382 autosomal single nucleotide polymorphisms (SNPs). ACR and eGFR data from all individuals of European ancestry were available for quantitative trait analysis. P-values were calculated using the standard case/control allelic tests. P-values, from quantitative trait analysis for estimated glomerular filtration rate are presented. All association tests were performed using PLINK. SNPs positions are in reference to NCBI Build 36.1 (3).

326 T2D individuals were screened and genotyped with and without DKD to evaluate whether any single nucleotide polymorphism (SNP) at the IL8, CXCR1 or CXCR2 gene could impact DKD onset. The strongest association with DKD in this population occurred at rs13006838 (log 10-p value=1.35), a SNP located at chromosome 2 in position 218461578 of the CXCR1 gene.

Similarly, in order to confirm if the IL8-CXCR1/2 axis is relevant for diabetic kidney disease (DKD) in T1D patients, we took advantage of the Genetics of Kidney disease (GoKind) population (n=829 cases; 904 control patients (2). In this population, the strongest association with the decline in estimated glomerular filtration rate (eGFR) occurred at the CXCR1 gene: (i) rs4674308 (chromosome 2, position 219018727), log 10-p value=1.36; (ii) rs4674309 (chromosome 2, position 219022817), log 10-p value=1.47; (iii) rs3755042 (chromosome 2, position 219025492), log 10-p value=1.36; (iv) rs7601872 (chromosome 2, position 219028129), log 10-p value=1.36; (v) rs664514 (chromosome 2, position 219038063), log 10-p value=1.31 (see Table 1 below).

A genotypic association for SNP on IL8 and CXCR1/2 locus with DN, ACR and eGFR was observed. The strongest association with the progression to ESRD or worsening of GFR on DN population occurred at rs13006838 (log 10-p value=1.35; p=0.045); this SNP is located at chromosome 2 in position 218461578 of the CXCR1 gene (Table 4). This finding indicates the importance of IL8-CXCR1/2 axis on the evolution of DN to ESRD. This association stop being significant when the GFR was adjusted to sex, age, Body Mass Index, glycosylated hemoglobin A1C. Regarding CXCR2 and IL8, no locus associated with the progression to ESRD, ACR or GFR was observed.

Example 7

IL8 and CXCR-1/2 are Expressed by Human Podocytes

Figure 9A:
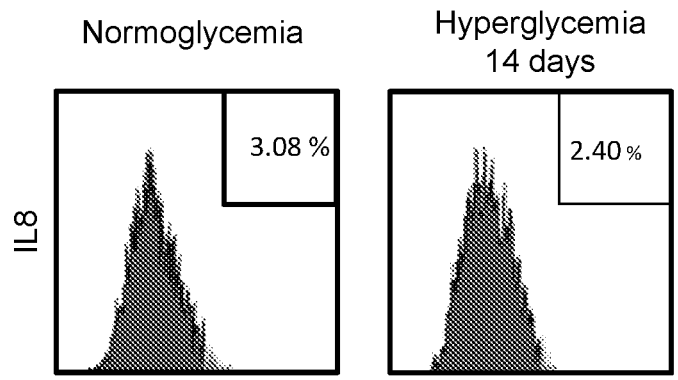
FIG. 9A presents experimental data plotting cells expressing IL8 in normoglycemia and hyperglycemia for 14 days.
Figure 9B:
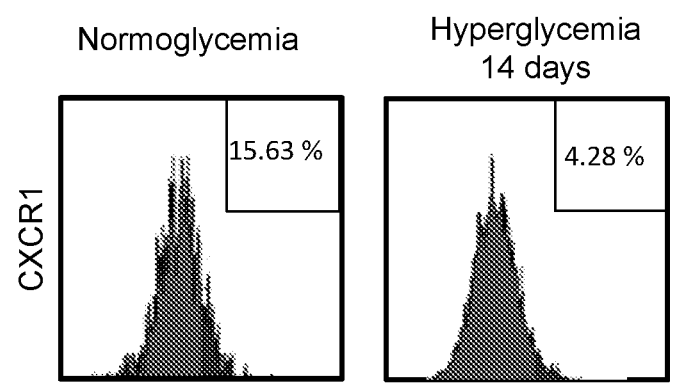
FIG. 9B presents experimental data plotting cells expressing CXCR-1 in normoglycemia and hyperglycemia for 14 days.
Figure 9C:
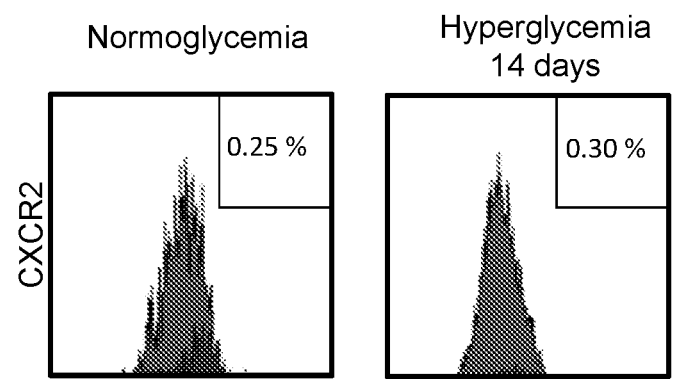
FIG. 9C presents experimental data plotting cells expressing CXCR-2 in normoglycemia and hyperglycemia for 14 days.

Human podocytes were investigated for IL8, CXCR1, and CXCR2 expression in vitro (FIGS. 9A-9C). Podocytes were cultured for 5 days after complete cell differentiation in either normal glucose (10 mM [NG]) or high glucose (30 mM [HG]) Mannitol (mannitol 20 mM+glucose 10 mM) was used as an osmotic control for high glucose. Immortalized podocyte cell lines were cultured using standard techniques known in the art. A weak expression of IL8 was detected in basal conditions and it was not affected by glucose levels in culture medium. By converse, CXCR-1 dropped from 15% to less than 5% from normo- to hyperglycemic medium. No significant change in CXCR-2 expression was detected (FIGS. 9B and 9C).

All in vitro and in vivo experimental data presented herein in the examples were performed in triplicate, unless indicated otherwise. Proteinuria in db/db mice was performed in 10 untreated and 30 treated animals. Prism statistical software (La Jolla, Calif.—USA) was used for data analysis. Data were classified by D'Agostino-Pearsons test (continuous non-normal distributed variables were displayed by median with interquartile range (IQR)), and analyzed with Mann-Whitney test (normal distributed variables were displayed by mean and standard deviation), and analyzed with two-tails paired t-test or one-way ANOVA. For discrete variables, χ2 test was used. For all tests, p<0.05 was considered significant.

REFERENCES

1. Orchard, T. J., Secrest, A. M., Miller, R. G. & Costacou, T. In the absence of renal disease, 20 year mortality risk in type 1 diabetes is comparable to that of the general population: a report from the Pittsburgh Epidemiology of Diabetes Complications Study. Diabetologia 53, 2312-2319 (2010).
2. National Institutes of Health, National Institute of Diabetes and Digestive and Kidney Diseases. United States Renal Data System. 2015 USRDS annual data report: Epidemiology of Kidney Disease in the United States. (2015).
3. Adler, A. I. et al. Development and progression of nephropathy in type 2 diabetes: The United Kingdom Prospective Diabetes Study (UKPDS 64). Kidney Int. 63, 225-232 (2003).
4. Tuttle, K. R. et al. Diabetic Kidney Disease: A Report From an ADA Consensus Conference. Am. J. Kidney Dis. 64, 510-533 (2014).
5. Fiorina, P. et al. Role of Podocyte B7-1 in Diabetic Nephropathy. J. Am. Soc. Nephrol. 25, 1415-1429 (2014).
6. Spranger, J. et al. Inflammatory cytokines and the risk to develop type 2 diabetes: results of the prospective population-based European Prospective Investigation into Cancer and Nutrition (EPIC)-Potsdam Study. Diabetes 52, 812-817 (2003).
7. Herder, C. et al. Inflammation and Type 2 Diabetes: Results from KORA Augsburg. Gesundheitswesen 67, 115-121 (2005).
8. Schumann, D. M. et al. The Fas pathway is involved in pancreatic beta cell secretory function. Proc. Natl. Acad. Sci. 104, 2861-2866 (2007).
9. Wolkow, P. P. et al. Association of Urinary Inflammatory Markers and Renal Decline in Microalbuminuric Type 1 Diabetics. J. Am. Soc. Nephrol. 19, 789-797 (2008).
10. Walz, A., Peveri, P., Aschauer, H. & Baggiolini, M. Purification and amino acid sequencing of NAF, a novel neutrophil-activating factor produced by monocytes. Biochem. Biophys. Res. Commun. 149, 755-761 (1987).
11. Russo, R. C., Garcia, C. C., Teixeira, M. M. & Amaral, F. A. The CXCL8/IL8 chemokine family and its receptors in inflammatory diseases. Expert Rev. Clin. Immunol. 10, 593-619 (2014).
12. Demetz, G. et al. Tissue Factor-Factor VIIa complex induces cytokine expression in coronary artery smooth muscle cells. Atherosclerosis 212, 466-471 (2010).
13. Huber, T. B. et al. Expression of Functional CCR and CXCR Chemokine Receptors in Podocytes. J. Immunol. 168, 6244-6252 (2002).
14. Tang, L.-M. et al. Activation of Adenosine A2A Receptor Attenuates Inflammatory Response in a Rat Model of Small-for-Size Liver Transplantation. Transplant. Proc. 42, 1915-1920 (2010).

TABLE 1

CXCR1 SNPs associated with DN

| | Chr | SNP | BP | Fct | Fc | P | G | gene |
|---|---|---|---|---|---|---|---|---|
| T1D | 2 | rs4674308 | 219018727 | 0.37 | 0.42 | 1.36 | | CXCR1 |
| | 2 | rs4674309 | 219022817 | 0.23 | 0.27 | 1.47 | | CXCR1 |
| | 2 | rs3755042 | 219025492 | 0.37 | 0.42 | 1.36 | | CXCR1 |
| | 2 | rs7601872 | 219028129 | 0.37 | 0.42 | 1.36 | * | CXCR1 |
| | 2 | rs664514 | 219038063 | 0.37 | 0.41 | 1.31 | | CXCR1 |
| T2D | 2 | Rs13006838 | 219034545 | 0.05 | 0.03 | 1.35 | | CXCR1 |

TABLE 2

GFR levels in patients with progressively reduced glomerular expression of IL8 and progressive kidney injury.

| Histopathology grading | IL8 Expression (AU) | GFR (ml/min/1.73 $m^2$) |
|---|---|---|
| Mesangial expansion | 3.0 ± 0.0 | 91.43 ± 7.74 |
| Nodular Transformation | 1.5 ± 0.41 | 62.29 ± 6.75 |
| Glomerulo-sclerosis | 0.0 ± 0.0 | 48.25 ± 8.52 |

TABLE 3

Table listing exemplary identified conditions. A subject identified to be suffering from one or a combination of the listed conditions can be treated with the methods disclosed herein.

| Identified conditions in a subject | Treatment with IL8 inhibitor; preferably a CXCR1/2inhibitor e.g., reparixin and/or ladarixin |
|---|---|
| Elevated urinary IL8 levels. | ✓ |
| At least one of the following single nucleotide polymorphisms at the CXCR1 locus: s13006838, rs4674308; rs4674309; rs3755042; rs7601872; and rs664514. | ✓ |
| Microalbuminuria. The measured rate of excretion of albumin can be e.g., between 30 and 300 mg per day. | ✓ |

TABLE 3-continued

Table listing exemplary identified conditions. A subject identified to be suffering from one or a combination of the listed conditions can be treated with the methods disclosed herein.

| Identified conditions in a subject | Treatment with IL8 inhibitor; preferably a CXCR1/2 inhibitor e.g., reparixin and/or ladarixin |
|---|---|
| Glomerular filtration rate which is above 60 ml/min/1.73 m$^2$, preferably above 90 ml/min/1.73 m$^2$. | ✓ |
| Diabetes | ✓ |
| Diabetes and elevated urinary IL8 levels | ✓ |
| Diabetes and at least one of the following single nucleotide polymorphisms at the CXCR1 locus: s13006838, rs4674308; rs4674309; rs3755042; rs7601872; and rs664514. | ✓ |
| Diabetes and increased urinary IL8 levels and at least one of the following single nucleotide polymorphisms at the CXCR1 locus: s13006838, rs4674308; rs4674309; rs3755042; rs7601872; and rs664514. | ✓ |
| Diabetes and microalbuminuria; the measured rate of excretion of albumin can be e.g., between 30 and 300 mg per day. | ✓ |
| Diabetes and glomerular filtration rate which is above 60 ml/min/1.73 m$^2$, preferably above 90 ml/min/1.73 m$^2$. | ✓ |
| Elevated urinary IL8 levels and at least one of the following single nucleotide polymorphisms at the CXCR1 locus: s13006838, rs4674308; rs4674309; rs3755042; rs7601872; and rs664514. | ✓ |
| Elevated urinary IL8 levels and microalbuminuria; the measured rate of excretion of albumin can be e.g., between 30 and 300 mg per day. | ✓ |
| Elevated urinary IL8 levels and Glomerular filtration rate which is above 60 ml/min/1.73 m$^2$, preferably above 90 ml/min/1.73 m$^2$. | ✓ |
| Microalbuminuria. The measured rate of excretion of albumin can be e.g., between 30 and 300 mg per day and At least one of the following single nucleotide polymorphisms at the CXCR1 locus: s13006838, rs4674308; rs4674309; rs3755042; rs7601872; and rs664514. | ✓ |
| Microalbuminuria. The measured rate of excretion of albumin can be e.g., between 30 and 300 mg per day and Glomerular filtration rate which is above 60 ml/min/1.73 m$^2$, preferably above 90 ml/min/1.73 m$^2$. | ✓ |
| At least one of the following single nucleotide polymorphisms at the CXCR1 locus: s13006838, rs4674308; rs4674309; rs3755042; rs7601872; and rs664514 and Glomerular filtration rate which is above 60 ml/min/1.73 m$^2$, preferably above 90 ml/min/1.73 m$^2$. | ✓ |

TABLE 4

Identified SNPs in the CXCR-2, CXCR-1, and CXCL-8 gene loci using genome-wide association study.

| n | CHR | SNP | BP | Fcs | Fct | Fcs2 | Fct2 | Pcs | Pcs2 | Qnra | QLnra | Qla | QLla | Qg | QLg | G | R2 | Gene |
|---|---|---|---|---|---|---|---|---|---|---|---|---|---|---|---|---|---|---|
| 1 | 2 | rs921968 | 218980538 | 0.44 | 0.4 | 0.44 | 0.4 | 0.51 | 0.48 | 0.44 | 0.68 | 0.71 | 1.04 | 0.82 | 1.03 | * | 1 | CXCR2 |
| 2 | 2 | rs7607369 | 218987341 | 0.43 | 0.42 | 0.44 | 0.41 | 0.15 | 0.33 | 0.36 | 0.68 | 0.53 | 0.93 | 0.75 | 0.83 | * | 1 | CXCR2 |
| 3 | 2 | rs13391398 | 218990673 | 0.33 | 0.33 | 0.34 | 0.32 | 0.01 | 0.18 | 0.33 | 0.92 | 0.35 | 1.07 | 0.14 | 0.49 |  | 0.97 | CXCR2 |
| 4 | 2 | rs17462630 | 218994785 | 0.33 | 0.33 | 0.34 | 0.32 | 0.18 | 0.33 | 0.92 | 0.35 | 1.07 | 0.14 | 0.49 |  |  | 0.97 | CXCR2 |
| 5 | 2 | rs10189479 | 218995520 | 0.43 | 0.42 | 0.44 | 0.41 | 0.15 | 0.33 | 0.36 | 0.68 | 0.53 | 0.93 | 0.75 | 0.83 |  | 0.97 | CXCR2 |
| 6 | 2 | rs10165754 | 218995614 | 0.33 | 0.33 | 0.33 | 0.32 | 0.01 | 0.18 | 0.33 | 0.97 | 0.38 | 1.18 | 0.2 | 0.62 |  | 0.95 | CXCR2 |
| 7 | 2 | rs3731866 | 218997143 | 0.32 | 0.32 | 0.32 | 0.31 | 0.03 | 0.13 | 0.29 | 0.88 | 0.31 | 1.03 | 0.05 | 0.43 | * | 1 | CXCR2 |
| 8 | 2 | rs4674305 | 219001570 | 0.43 | 0.42 | 0.44 | 0.4 | 0.19 | 0.37 | 0.39 | 0.75 | 0.6 | 1.07 | 0.85 | 0.99 |  | 0.98 | CXCR2 |
| 9 | 2 | rs6720403 | 219002502 | 0.41 | 0.39 | 0.41 | 0.37 | 0.26 | 0.4 | 0.58 | 1.04 | 0.7 | 1.25 | 0.63 | 0.93 |  | 0.95 | CXCR2 |
| 10 | 2 | rs3821031 | 219003493 | 0.41 | 0.39 | 0.41 | 0.37 | 0.26 | 0.4 | 0.58 | 1.04 | 0.7 | 1.25 | 0.63 | 0.93 |  | 0.95 | CXCR2 |
| 11 | 2 | rs17572485 | 219004789 | 0.41 | 0.38 | 0.41 | 0.37 | 0.3 | 0.45 | 0.61 | 1.06 | 0.75 | 1.29 | 0.61 | 0.89 |  | 0.93 | CXCR2 |
| 12 | 2 | rs4674308 | 219018727 | 0.39 | 0.39 | 0.39 | 0.37 | 0.03 | 0.21 | 0.43 | 1.13 | 0.46 | 1.25 | 0.44 | 0.94 |  | 0.97 | CXCR1 |
| 13 | 2 | rs4674309 | 219022817 | 0.25 | 0.25 | 0.25 | 0.25 | 0.03 | 0.02 | 0.29 | 0.89 | 0.19 | 0.78 | 0.04 | 0.2 |  | 0.88 | CXCR1 |
| 14 | 2 | rs3755042 | 219025492 | 0.39 | 0.39 | 0.39 | 0.37 | 0.03 | 0.21 | 0.43 | 1.13 | 0.46 | 1.25 | 0.44 | 0.94 |  | 0.97 | CXCR1 |
| 15 | 2 | rs7601872 | 219028129 | 0.39 | 0.39 | 0.39 | 0.37 | 0.03 | 0.21 | 0.43 | 1.13 | 0.46 | 1.25 | 0.44 | 0.94 |  | 0.97 | CXCR1 |
| 16 | 2 | rs3932856 | 219028451 | 0.44 | 0.42 | 0.44 | 0.41 | 0.23 | 0.43 | 0.42 | 0.85 | 0.63 | 1.17 | 0.91 | 1.14 |  | 0.96 | CXCR1 |
| 17 | 2 | rs832810 | 219030674 | 0.44 | 0.42 | 0.44 | 0.41 | 0.23 | 0.43 | 0.42 | 0.85 | 0.63 | 1.17 | 0.91 | 1.14 |  | 0.96 | CXCR1 |
| 18 | 2 | rs13006838 | 219034545 | 0.05 | 0.03 | 0.05 | 0.03 | 0.74 | 0.65 | 0.13 | 0.15 | 0.51 | 0.1 | 1.35 | 0.59 |  | 0.87 | CXCR1 |
| 19 | 2 | rs10189064 | 219035744 | 0.04 | 0.03 | 0.04 | 0.03 | 0.13 | 0.05 | 0.04 | 0.2 | 0.23 | 0.5 | 0.5 | 0.87 | * | 0.99 | CXCR1 |
| 20 | 2 | rs520095 | 219037729 | 0.44 | 0.42 | 0.44 | 0.4 | 0.27 | 0.48 | 0.46 | 0.87 | 0.68 | 1.21 | 1.02 | 1.25 |  | 0.96 | CXCR1 |
| 21 | 2 | rs664514 | 219038063 | 0.39 | 0.39 | 0.39 | 0.37 | 0.03 | 0.21 | 0.43 | 1.13 | 0.46 | 1.25 | 0.44 | 0.94 |  | 0.95 | CXCR1 |
| 22 | 4 | rs1919480 | 74596603 | 0.04 | 0.06 | 0.05 | 0.06 | 0.44 | 0.23 | 0.27 | 0.32 | 0.06 | 0.06 | 0.84 | 0.76 |  | 0.96 | CXCL8 |
| 23 | 4 | rs12510629 | 74599194 | 0.3 | 0.31 | 0.31 | 0.3 | 0.1 | 0.12 | 0.45 | 0.46 | 0.2 | 0.19 | 0.51 | 0.39 |  | 0.99 | CXCL8 |
| 24 | 4 | rs2141470 | 74603954 | 0.32 | 0.34 | 0.33 | 0.33 | 0.28 | 0.03 | 0.48 | 0.44 | 0.14 | 0.09 | 0.41 | 0.37 |  | 1 | CXCL8 |

TABLE 4-continued

Identified SNPs in the CXCR-2, CXCR-1, and CXCL-8 gene loci using genome-wide association study.

| n | CHR | SNP | BP | Fcs | Fct | Fcs2 | Fct2 | Pcs | Pcs2 | Qnra | QLnra | Qla | QLla | Qg | QLg | G | R2 | Gene |
|---|---|---|---|---|---|---|---|---|---|---|---|---|---|---|---|---|---|---|
| 25 | 4 | rs1528924 | 74609840 | 0.3 | 0.31 | 0.31 | 0.3 | 0.1 | 0.12 | 0.45 | 0.46 | 0.2 | 0.19 | 0.51 | 0.39 | | 0.99 | CXCL8 |
| 26 | 4 | rs6815239 | 74610497 | 0.03 | 0.04 | 0.03 | 0.03 | 0.22 | 0.04 | 0.28 | 0.14 | 0.09 | 0.03 | 0.12 | 0.1 | | 0.75 | CXCL8 |
| 27 | 4 | rs4453908 | 74612963 | 0.02 | 0.04 | 0.02 | 0.03 | 0.54 | 0.3 | 0.07 | 0 | 0.16 | 0.28 | 0.16 | 0.01 | | 0.97 | CXCL8 |
| 28 | 4 | rs6856952 | 74613267 | 0.02 | 0.04 | 0.02 | 0.03 | 0.54 | 0.3 | 0.07 | 0 | 0.16 | 0.28 | 0.16 | 0.01 | | 0.97 | CXCL8 |
| 29 | 4 | rs10938085 | 74615443 | 0.3 | 0.31 | 0.31 | 0.3 | 0.1 | 0.12 | 0.45 | 0.46 | 0.2 | 0.19 | 0.51 | 0.39 | | 0.99 | CXCL8 |
| 30 | 4 | rs10938086 | 74615570 | 0.3 | 0.31 | 0.31 | 0.3 | 0.1 | 0.12 | 0.45 | 0.46 | 0.2 | 0.19 | 0.51 | 0.39 | | 0.99 | CXCL8 |
| 31 | 4 | rs6852024 | 74616002 | 0.02 | 0.04 | 0.02 | 0.03 | 0.54 | 0.3 | 0.07 | 0 | 0.16 | 0.28 | 0.16 | 0.01 | | 0.97 | CXCL8 |
| 32 | 4 | rs13353732 | 74616018 | 0.32 | 0.34 | 0.33 | 0.33 | 0.28 | 0.03 | 0.48 | 0.44 | 0.14 | 0.09 | 0.41 | 0.37 | | 1 | CXCL8 |
| 33 | 4 | rs10016403 | 74618271 | 0.32 | 0.34 | 0.33 | 0.33 | 0.28 | 0.03 | 0.48 | 0.44 | 0.14 | 0.09 | 0.41 | 0.37 | | 1 | CXCL8 |
| 34 | 4 | rs7690011 | 74618288 | 0.05 | 0.05 | 0.05 | 0.04 | 0.08 | 0.14 | 0.59 | 0.58 | 0.24 | 0.22 | 0.26 | 0.22 | | 0.75 | CXCL8 |

We claim:

1. A method of preventing the onset of diabetic nephropathy or the progression of diabetic nephropathy (DN) in a subject in need thereof comprising administering an IL-8 inhibitor to the subject who has been diagnosed with diabetes and microalbuminuria, wherein the IL-8 inhibitor is a CXCR1 and/or CXCR2-inhibitor, and wherein the IL-8 inhibitor is a compound selected from the group consisting of R(−)-2-[(4-isobutylphenyl)propionyl]-methanesulfonamide, R(−)-2[(4'-trifluoromethane sulfonyloxy)phenyl]-N-methanesulfonyl propionamide and (2S)-2-(4-{[4-(trifluoromethyl)-1,3-thiazol-2-yl] amino}phenyl) propionic acid and salts thereof.

2. The method of claim 1, wherein the IL-8 inhibitor is a compound selected from the group consisting of the lysine salt of R(−)-2[(4-isobutylphenyl)propionyl]-methanesulfonamide, the sodium salt of R(−)-2[(4'-trifluoromethane sulfonyloxy)phenyl]-N-methanesulfonyl propionamide, and the sodium salt of 2-(4-{[4-(trifluoromethyl)-1,3-thiazol-2-yl]amino}phenyl) propionic acid.

3. The method of claim 1, wherein the diabetes is Type 1 diabetes (T1D) or Type 2 diabetes (T2D).

4. The method of claim 1, wherein the subject has at least one of the following single nucleotide polymorphisms at the CXCR1 locus: s13006838, rs4674308; rs4674309; rs3755042; rs7601872; and rs664514.

5. The method of claim 1, further comprising measuring the protein level in a sample of urine from the subject.

6. The method of claim 5, further comprising comparing the measured urine protein level with a urine protein reference, wherein the urine protein reference is the level of protein in urine samples obtained in normal healthy subjects that do not have any nephropathy.

7. The method of claim 1, further comprising measuring the IL8 level in a sample obtained from the subject.

8. The method of claim 7, wherein in the sample is a urine sample, kidney biopsy, a serum sample, a blood sample, or a plasma sample.

9. The method of claim 7, further comprising comparing the measured IL8 level with an IL8 reference, wherein the IL8 reference is the IL8 level in the respective samples obtained in normal healthy subjects that do not have any nephropathy.

10. The method of claim 1, wherein the IL8 inhibitor is administered to the subject prior to, simultaneously or sequentially with the administration of at least one other therapy for diabetes, metabolic syndrome, cardiovascular disease or high blood pressure.

11. The method of claim 1, wherein the IL8 inhibitor is administered with at least one active molecule used to treat diabetes.

12. The method of claim 1, wherein the IL8 inhibitor is in a composition formulated for delivery to the kidney.

13. The method of claim 1, wherein the IL8 inhibitor is administered by a systemic route, an enteral route, or a parenteral route.

14. The method of claim 1, wherein the daily dosage of the IL8 inhibitor is between 1 mg and 100 mg.

15. The method of claim 1, wherein the subject has been determined to have a value of glomerular filtration rate (GFR) above 60 ml/min/1.73m$^2$.

16. The method of claim 7, wherein the subject has been determined to have a urinary level of IL8 higher than 2.41 pg/ml.

17. The method of claim 5, wherein the subject has been determined to have rate of excretion of albumin between 30 mg and 300 mg per day.

18. A method of preventing the onset of diabetic nephropathy or the progression of diabetic nephropathy (DN) in a subject in need thereof comprising:
measuring the IL-8 level in a sample from the subject who has been diagnosed with diabetes, and
administering an IL-8 inhibitor to the subject, and
wherein the IL-8 inhibitor is a CXCR1 and/or CXCR2-inhibitor, and wherein the IL-8 inhibitor is a compound selected from the group consisting of R(−)-2[(4-isobutylphenyl)propionyl]-methanesulfonamide, R(−)-2[(4'-trifluoromethane sulfonyloxy)phenyl]-N-methanesulfonyl propionamide and (2S)-2-(4-{[4-(trifluoromethyl)-1,3-thiazol-2-yl] amino}phenyl) propionic acid and salts thereof.

19. The method of claim 18, wherein the subject has been determined to have a urinary level of IL-8 higher than 2.41 pg/ml.

20. A method of preventing the onset of diabetic nephropathy or the progression of diabetic nephropathy (DN) in a subject in need thereof comprising: administering an IL-8 inhibitor to the subject who has been diagnosed with diabetes, and wherein the IL-8 inhibitor is a CXCR1 and/or CXCR2-inhibitor, and wherein the IL-8 inhibitor is a compound selected from the group consisting of R(−)-2[(4-isobutylphenyl)propionyl]-methanesulfonamide, R(−)-2[(4'-trifluoromethane sulfonyloxy)phenyl]-N-methanesulfonyl propionamide and (2S)-2-(4-{[4-(trifluoromethyl)-1,3-thiazol-2-yl] amino}phenyl) propionic acid and salts thereof, and wherein the IL8 inhibitor is in a composition formulated for delivery to the kidney.

* * * * *